United States Patent
Dang et al.

(10) Patent No.: US 7,264,964 B2
(45) Date of Patent: Sep. 4, 2007

(54) CHIMERIC HISTONE ACETYLTRANSFERASE POLYPEPTIDES

(75) Inventors: Van-Dinh Dang, Oak Park, CA (US); Jack Okamuro, Oak Park, CA (US)

(73) Assignee: Ceres, Inc., Thousand Oaks, CA (US)

(*) Notice: Subject to any disclaimer, the term of this patent is extended or adjusted under 35 U.S.C. 154(b) by 180 days.

(21) Appl. No.: 10/177,478

(22) Filed: Jun. 21, 2002

(65) Prior Publication Data

US 2003/0165903 A1 Sep. 4, 2003

Related U.S. Application Data

(60) Provisional application No. 60/300,135, filed on Jun. 22, 2001.

(51) Int. Cl.
C07H 21/02 (2006.01)
C12N 15/00 (2006.01)

(52) U.S. Cl. .................. 435/320.1; 536/23.4; 536/23.6; 536/23.74

(58) Field of Classification Search ............... 536/23.4, 536/23.1, 23.5; 435/320.1
See application file for complete search history.

(56) References Cited

U.S. PATENT DOCUMENTS

| | | | |
|---|---|---|---|
| 4,851,341 A | 7/1989 | Hopp et al. | |
| 4,873,191 A | 10/1989 | Wagner et al. | |
| 5,001,912 A | 3/1991 | DeWalch | |
| 5,070,020 A | 12/1991 | Ingolia et al. | |
| 5,204,253 A | 4/1993 | Sanford et al. | |
| 5,252,726 A | 10/1993 | Wöldike | |
| 5,424,186 A | 6/1995 | Fodor et al. | |
| 5,491,084 A | 2/1996 | Chalfie et al. | |
| 5,801,027 A | 9/1998 | Bennett et al. | |
| 5,907,082 A | 5/1999 | O'Neill et al. | |
| 5,968,793 A | 10/1999 | Liu et al. | |
| 5,972,608 A | 10/1999 | Peterson et al. | |
| 5,989,897 A * | 11/1999 | Pillus et al. ............ 435/254.2 | |
| 6,011,200 A | 1/2000 | Dellaporta et al. | |
| 6,013,863 A | 1/2000 | Lundquist et al. | |
| 6,127,606 A | 10/2000 | Bennett et al. | |
| 6,153,741 A | 11/2000 | Richards et al. | |
| 6,156,501 A | 12/2000 | McGall et al. | |
| 6,166,192 A | 12/2000 | Spiegelman et al. | |
| 6,222,097 B1 | 4/2001 | McBride et al. | |
| 6,229,064 B1 | 5/2001 | Fischer et al. | |
| 6,235,975 B1 | 5/2001 | Harada et al. | |
| 6,239,327 B1 | 5/2001 | Grossniklaus et al. | |
| 6,248,520 B1 | 6/2001 | Roeder et al. | |
| 6,255,558 B1 | 7/2001 | Haseloff et al. | |
| 6,320,102 B1 | 11/2001 | Harada et al. | |
| 6,545,201 B1 | 4/2003 | Harada et al. | |
| 6,559,357 B1 | 5/2003 | Fischer et al. | |
| 6,781,035 B1 | 8/2004 | Harada et al. | |
| 6,906,244 B2 | 6/2005 | Fischer et al. | |
| 2002/0004940 A1 | 1/2002 | Simmons | |
| 2002/0022256 A1 | 2/2002 | Baldwin et al. | |
| 2002/0115215 A1* | 8/2002 | Wolffe et al. ............... 435/455 | |
| 2003/0126642 A1 | 7/2003 | Fischer et al. | |

FOREIGN PATENT DOCUMENTS

| | | |
|---|---|---|
| CA | 2316036 | 2/2001 |
| EP | 1 094 112 A2 | 4/2001 |
| WO | WO96/04393 | 2/1996 |
| WO | WO96/35784 | 11/1996 |
| WO | WO97/10704 | 3/1997 |
| WO | WO97/31064 | 8/1997 |
| WO | WO97/43427 | 11/1997 |
| WO | WO98/08961 | 3/1998 |
| WO | WO98/28431 | 7/1998 |
| WO | WO98/33374 | 8/1998 |
| WO | WO98/36090 | 8/1998 |
| WO | WO98/56934 | 12/1998 |
| WO | WO9856934 A1 * | 12/1998 |
| WO | WO99/53050 | 10/1999 |
| WO | WO99/53083 | 10/1999 |
| WO | WO99/57247 | 11/1999 |
| WO | WO99/67405 | 12/1999 |
| WO | WO 00/24914 | 5/2000 |
| WO | WO 00/28058 | 5/2000 |
| WO | WO 00/40694 | 7/2000 |
| WO | WO 00/75330 | 12/2000 |
| WO | WO 01/09299 | 2/2001 |
| WO | WO 01/16325 | 3/2001 |

(Continued)

OTHER PUBLICATIONS

Preuss. Chromatin silencing and *Arabidopsis* development: A role for polycomb proteins.☐☐Plant Cell. vol. 11, No. 5, pp. 765-767, May 1999.*
Ohad et al. Mutations in FIE, and WD polycomb group gene, allow endosperm development without fertilization. Plant Cell. vol. 11, No. 3, pp. 407-416, Mar. 1999.*
Yadegari et al. Mutations in the FIE and MEA genes that encode interacting polycomb proteins cause parent-of-origin effects on seed development by distinct mechanisms. Plant Cell. vol. 12, No. 12, pp. 2367-2382, Dec. 2000.*
Sobulo et al. MLL is fused to CBP, a histone acetyltransferase, in therapy-related acute myeloid leukemia with a t(11;16)(q23;p13.3). Proc Natl Acad Sci U S A. vol. 94, No. 16, pp. 8732-8737, Aug. 1997.*
GenBank Accession No. Q08649, GI: 3023717, Feb. 1, 1998.*
Danilevskaya et al. Duplicated fie genes in maize: Expression pattern and imprinting suggest distinct functions. The Plant Cell, vol. 15, pp. 425-438, Feb. 2003.*

(Continued)

*Primary Examiner*—Celine Qian
*Assistant Examiner*—Jennifer Dunston
(74) *Attorney, Agent, or Firm*—Fish & Richardson P.C.

(57) ABSTRACT

Chimeric polypeptides are disclosed that comprise a first polypeptide segment having histone acetyltransferase enzymatic activity and a second polypeptide segment that is similar to a subunit of a chromatin-associated histone deacetyltransferase protein complex. Also disclosed are nucleic acids encoding such chimeric polypeptides and eukaryotic organisms expressing such chimeric polypeptides.

4 Claims, No Drawings

FOREIGN PATENT DOCUMENTS

WO   WO 03/000038 A2   1/2003

OTHER PUBLICATIONS

Martinez-Balbás et al., "*Drosophila* NURF-55, a WD repeat protein involved in histone metabolism," *Proc. Natl. Acad. Sci. USA*, 1998, 95:132-137.
GenBank A43, Mar. 23, 2002.
GenBank Accession No. J02798, Oct. 11, 2001.
GenBank Accession No. J05212, Jun. 1, 1995.
GenBank Accession No. K00821, Apr. 27, 1993.
GenBank Accession No. L05934, Oct. 22, 1993.
GenBank Accession No. M28156, Oct. 6, 1994.
GenBank Accession No. M63985, Apr. 27, 1993.
GenBank Accession No. S44893, May 8, 1993.
GenBank Accession No. U09118, Jan. 19, 2000.
GenBank Accession No. U09119, Jul. 24, 2001.
GenBank Accession No. U39944, Jul. 31, 1996.
GenBank Accession No. U76670, Jan. 23, 1997.
GenBank Accession No. U93215, Feb. 27, 2002.
GenBank Accession No. X15121, Feb. 10, 1999.
GenBank Accession No. Z17657, Nov. 10, 1992.
GenBank Accession No. AF096096, Jan. 25, 1999.
GenBank Accession No. AF129516, Apr. 6, 1999.
GenBank Accession No. AF233296, Apr. 24, 2000.
GenBank Accession No. AL161566, Mar. 16, 2000.
http://www.plantsci.cam.ac.uk/Haseloff/Index/Catalogue. html—Database Index, 1 pg., No. 15, 2002.
http://www.sanger.ac.uk/Software/Pfam—Pfam—"Protein families database of alignments and HMMs," 1 pg. Jan. 13, 2003.
Aalfs and Kingston, "What does 'chromatin remodeling' mean?" *TIBS*, 2000, 25:548-555.
Abler and Scandalios, "Isolation and characterization of a genomic sequence encoding the maize *Cat3* catalase gene," *Plant Mol. Biol.*, 1993, 22:1031-1038.
Altschul et al., "Gapped BLAST and PSI-BLAST: a new generation of protein database search programs," *Nucl. Acids Res.*, 1997, 25(17):3389-3402.
Amedeo et al., "Disruption of the plant gene *MOM* releases transcriptional silencing of methylated genes," *Nature*, 2000, 405:203-206.
Archer and Lee, "Visualization of Multicomponent Transcription Factor Complexes on Chromatin and Nonnucleosomal Templates in Vivo," *Methods: A Companion to Methods in Enzymology*, 1997, 11:235-245.
Bai et al., "Isolation and Characterization of SYNI, a RAD21-like Gene Essential for Meiosis in *Arabidopsis*," *Plant Cell*, 1999, 11:417-430.
Bateman et al., "Pfam 3.1: 1313 multiple alignments and profile HMMs match the majority of proteins," *Nucl. Acids Res.*, 1999, 27(1):260-262.
Bazett-Jones et al., "The SWI/SNF Complex Creates Loop Domains in DNA and Polynucleosome Arrays and Can Disrupt DNA-Histone Contact within These Domains," *Mol. Cell. Biol.*, 1999, 19(2):1470-1478.
Bezerra et al., "a corn-specific gene encodes tarin, a major globulin of taro (*Colocasia esculenta* L. Schott)," *Plant Mol. Biol.*, 1995, 28:137-144.
Blume and Grierson, "Expression of ACC oxidase promoter-GUS fusions in tomato and *Nicotiana plumbaginifolia* regulated by developmental and environmental stimuli," *Plant J.*, 1997, 12(4):731-746.
Bossinger and Smyth, "Initiation patterns of flower and floral organ development in *Arabidopsis thaliana*," *Development*, 1996, 122(4):1093-1102.
Bowman et al., "Expression of the *Arabidopsis* Floral Homeotic Gene *AGAMOUS* Is Restricted to Specific Cell Types Late in Flower Development," *Plant Cell*, 1991, 3:749-758.
Breiling et al., "General transcription factors bind promoters repressed by Polycomb group proteins," *Nature*, 2001, 412:651-655.

Brownell and Allis, "An activity gel assay detects a single, catalytically active histone acetyltransferase subunit in *Tetrahymena* macronuclei," *Proc. Natl. Acad. Sci. USA*, 1995, 92:6364-6368.
Brownell et al., "Tetrahymena Histone Acetyltransferase A: A Homolog to Yeast Gen5p Linking Histone Acetylation to Gene Activation," *Cell*, 1996, 84:843-851.
Busk et al., "Regulatory elements in vivo in the promoter of the abscisic acid responsive gene *rab17* from maize," *Plant J.*, 1997, 11(6):1285-1295.
Bustos et al., "Regulation of β-Glucuronidase Expression in Transgenic Tobacco Plants by an A/T-Rich, cis-Acting Sequence Found Upstream of a French Bean β-Phaseolin Gene," *Plant Cell*, 1989, 1:839-853.
Cao et al., "Conserved plant genes with similarity to mammalian *de novo* DNA methyltransferases," *Proc. Natl. Acad. Sci. USA*, 2000, 97(9):4979-4984.
Casal et al., "Different Phototransduction Kinetics of Phytochrome A and Phytochrome B in *Arabidopsis thaliana*," *Plant Physiol.*, 1998, 116:1533-1538.
Chaudhury et al., "Fertilization-independent seed development in *Arabidopsis thaliana*," *Proc. Natl. Acad. Sci. USA*, 1997, 94:4223-4228.
Chen and Foolad, "Molecular organization of a gene in barley which encodes a protein similar to aspartic protease and its specific expression in nucellar cells during degeneration," *Plant Mol. Biol.*, 1997, 35:821-831.
Choi et al., "Tissue-specific and developmental regulation of a gene encoding a low molecular weight sulfur-rich protein in soybean seeds," *Mol. Gen. Genet.*, 1995, 246:266-268.
Colombo et al., "Downregulation of Ovule-Specific MADS Box Genes from Petunia Results in Maternally Controlled Defects in Seed Development," *Plant Cell*, 1997, 9:703-715.
Conceicao and Krebbers, "A cotyledon regulatory region is responsible for the different spatial expression patterns of *Arabidopsis* 2S albumin genes," *Plant J.*, 1994, 5(4):493-505.
Cress and Seto, "histone Deacetylases, Transcriptional Control, and Cancer," *J. Cell. Physiol.*, 2000, 184:1-16.
Dasgupta et al., "Cloning and sequencing of 5' flanking sequence from the gene encoding 2S storage protein from two *Brassica* species," *Gene*, 1993, 133:301-302.
Davie and Moniwa, "Control of Chromatin Remodeling,"*Critical Reviews in Eukaryotic Gene Expression*, 2000, 10(3 & 4):303-325.
De Castro et al., "Spatial and Temporal Gene Expression Patterns Occur during Corm Development," *Plant Cell*, 1992, 4:1549-1559.
Di Laurenzio et al., "The SCARECROW Gene Regulates an Asymmetric Cell Division That Is Essential for Generating the Radial Organization of the Arabidopsis Root," *Cell*, 1996, 86:423-433.
Dieffenbach and Dveksler, *PCR Primer—A Laboratory Manual*, 1995 Cold Spring Harbor Laboratory Press, (Table of Contents only).
Drews et al., "Negative Regulation of the *Arabidopsis* Homeotic Gene *AGAMOUS* by the *APETALA2* Product, " *Cell*, 65:991-1002.
Elias et al., "Transcription rate modulation through the *Trypanosoma cruzi* life cycle occurs in parallel with changes in nuclear organisation," *Mol. Biochem. Parasitol.*, 2001, 112:79-90.
Enjuto et al., "Expression of the Arabidopsis *HMG2* Gene, Encoding 3-Hydroxyl-3-Methylglutaryl Coenzyme A Reductase, Is Restricted to Meristematic and Floral Tissues," *Plant Cell*, 1995, 7:517-527.
Farkas et al., "Chromatin organization and transcriptional control of gene expression in *Drosophila*," *Gene*, 2000, 253:117-136.
Ficker et al., "A promoter directing high level expression in pistils of transgenic plants," *Plant Mol. Biol.*, 1997, 35:425-431.
Ficker et al., "Multiple elements of the $S_2$-Rnase promoter from potato (*Solanum tuberosum* L.) are required for cell type-specific expression in transgenic potato and tobacco," *Mol. Gen. Genet.*, 1998, 257:132-142.
Flaus and Owen-Hughes, "Mechanisms for ATP-dependent chromatin remodeling," *Curr. Opin. Genet. Devel.*, 2001, 11:148-154.
Fry and Peterson, "Chromatin remodeling enzymes: who's on first?" *Current Biology*, 2001, 11:R185-R197.

Gao and Benyajati, "Specific local histone-DNA sequence contacts facilitate high-affinity, non-cooperative nucleosome binding of both Adf-1 and GAGA factor," *Nucl. Acids Res.*, 1998, 26(23):5394-5401.

Gebuhr et al., "Pc-G/trx-G and the SWI/SNF Connection: Developmental Gene Regulation Through Chromatin Remodeling," *Genesis*, 2000, 26:189-197.

Gong et al., "Essential Role of NF-E2 in Remodeling of Chromatin Structure and Transcriptional Activation of the ε-Globin Gene In Vivo by 5' Hypersensitive Site 2 of the β-Globin Locus Control Region," *Mol. Cell. Biol.*, 1996, 16(11):6055-6064.

Goodrich et al., "A Polycomb-group gene regulates homeotic gene expression in *Arabidopsis*," *Nature*, 1997, 386:44-51.

Goodrich, "Plant development: Medea's maternal instinct," *Current Biology*, 1998, 8:R480-R484.

Granger et al. "Isolation of an *Arabidopsis* homologuge of the maize homeobox *Knotted-l* gene," *Plant Mol. Biol.*, 1996, 31:373-378.

Green et al., "Binding site requirements for pea nuclear protein factor GT-1 correlate with sequences required for light-dependent transcriptional activation fo the *rbcS-3A* gene," *EMBO J.*, 1988, 7(13):4035-4044.

Gregory et al., "Histone Acetylation and Chromatin Remodeling," *Experimental Cell Res.*, 2001, 265:195-202.

Grossniklaus et al., "Maternal Control of Embryogenesis to MEDEA, a *Polycomb* Group Gene in *Arabidopsis*," *Science*, 1998, 280:446-450.

Grossniklaus et al., "Genomic imprinting and seed development: endosperm formation with and without sex," *Curr. Opin. Plant Biol.*, 2001, 4:21-27.

Guerrero et al., "Promoter sequences from a maize pollen-specific gene direct tissue-specific transcription in tobacco," *Mol. Gen. Genet.*, 1990, 224:161-168.

Gustafson-Brown et al., "Regulation of the *Arabidopsis* Floral Homeotic Gene APETALA I," *Cell*, 1994, 76:131-143.

Guyon et al., "Stability of a Human SWI-SNF Remodeled Nucleosomal Array," *Mol. Cell. Biol.*, 2001, 21(4):1132-1144.

Hager et al., "Dynamics of gene targeting and chromatin remodelling by nulcear receptors," *Biochem. Soc. Trans.*, 2000, 28(4):405-410.

Hake et al., "Homeobox genes in the functioning of plant meristems," *Phil. Trans. R. Soc. Lond.*, 1995, 350:45-51.

Hansen et al., "Wound-inducible and organ-specific expression of ORF13 from *Agrobacterium rhizogenes* 8196 T-DNA in transgenic tobacco plants," *Mol. Gen. Genet.*, 1997, 254:337-343.

Haseloff et al., "Removal of a cryptic intron and subcellular localization of green fluorescent protein are required to mark transgenic *Arabidopsis* plants brightly," *Proc. Natl. Acad. Sci. USA*, 1997, 94:2122-2127.

Hassan et al., "Histone Acetyltransferase Complexes Stabilize SWI/SNF Binding to Promoter Nucleosomes," *Cell*, 2001, 104:817-827.

Ikeda et al., "Activation Domain-Specific and General Transcription Stimulation by Native Histone Acetyltransferase Complexes," *Mol. Cell. Biol.*, 1999, 19:855-863.

Ingram et al., "Transgenic Tobacco Plants Expressing the Drosophila Polycomb (Pc) Chromodormain Show Developmental Alterations: Possible Role of Pc Chromodomain Proteins in Chromatin-Mediated Gene Regulation in Plants," *Plant Cell*, 1999, 11:1047-1060.

Jackson et al., "Control of CpNpG DNA methylation by the KRYPTONITE histone H3 methyltransferase," *Nature*, 2002, 416:556-560.

Jaskelioff et al., "SWI-SNF Mediated Nucleosome Remodeling: Role of Histone Octamer Mobility in the Persistence of the Remodeled State," *Mol. Cell. Biol.*, 2000, 20(9):3058-3068.

Jeddeloh et al,. "Maintenance of genomic methylation requires a SWI2/SNF2-like protein," *Nature Genetics*, 1999, 22:94-97.

Ji and Langridge, "An early meiosis cDNA clone from wheat," *Mol. Gen. Genet.*, 1994, 243:17-23.

Jofuku et al., "Control of *Arabidopsis* Flower and Seed Development by the Homeotic Gene *APETALA2*," *Plant Cell*, 1994, 6:1211-1225.

Jones et al., "Methylated DNA and MeCP2 recruit histone deacetylase to repress transcription," *Nature Genetics*, 1998, 19:187-191.

Jordano et al., "A Sunflower Helianthinin Gene Upstream Sequence Ensemble Contains an Enhancer and Sites of Nuclear Protein Interaction," *Plant Cell*, 1989, 1:855-866.

Josefsson et al., "Structure of a Gene Encoding the 1.7 S Storage Protein, Napin, from *Brassice napus*," *J. Biol. Chem.*, 1987, 262(25):12196-12201.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Kent et al., "In vivo chromatin remodeling by yeast ISWI homologs Isw1p and Isw1p," *Genes & Development*, 2001, 15:619-626.

Kerstetter et al., "Sequence Analysis and Expression Patterns Divide the Maize *knotttedl*-like Homebox Genes into Two Classes," *Plant Cell*, 1994, 6:1877-1887.

Kim et al., "Nuclear protein factors binding to a class I patatin promoter region are tuber-specific and sucrose-inducible," *Plant Mol. Biol.*, 1994, 26:603-615.

Kiyosue et al., "Control of fertilization-independent endosperm development by the *MEDEA* polycomb gene *Arabidopsis*," *Proc. Natl. Acad. Sci. USA*, 1999, 96:4186-4191.

Klimyuk and Jones, "*AtDMCI*, the *Arabidopsis* homologue of the yeast *DMCI* gene: characterization, transposon-induced allelic variation and meiosis-associated expression," *Plant J.*, 1997, 11(1):1-14.

Kobayashi et al., "Characterization of cDNAs Induced in Meiotic Prophase in Lily Microsporocytes," *DNA Research*, 1994, 1:15-26.

Krebs and Peterson, "Understanding Active Chromatin: A Historical Perspective of Chromatin Remodeling," *Critical Reviews in Eukaryotic Gene Expression*, 2000, 10(1):1-12.

Kulikauskas and McCormick, "Identification of the tobacco and *Arabidopsis* homologues of the pollen-expressed LAT59 gene to tomato," *Plant Mol. Biol.*, 1997, 34:809-814.

Kumagai et al., "Cytoplasmic inhibition of carotenid biosynthesis with virus-derived RNA," *Proc. Natl. Acad. Sci. USA*, 1995, 92:1679-1683.

Kundu et al., "Activator-Dependent Transcription from Chromatin In Vitro Involving Targeted Histone Acetylation by p300," *Mol. Cell*, 2000, 6:551-561.

Lee and Huang, "Genes encoding oleosins in maize kernel of inbreds Mo17 and B73," *Plant Mol. Biol.*, 1994, 26:1981-1987.

Levin, "A Novel Mechanism of Self-Primed Reverse Transcription Defines a New Family of Retroelements," *Mol. Cell. Biol.*, 1995, 15(6):3310-3317.

Li et al., "A novel *myb*-related gene from *Arabidopsis thaliana*," *FEBS Lett.*, 1996, 379:117-121.

Lincoln et al., "A *knottedl*-like Homeobox Gene in *Arabidopsis* Is Expressed in the Vegetative Meristem and Dramatically Alters Leaf Morphology When Overexpressed in Transgenic Plants," 1994, 6:1859-1876.

Lindroth et al., "Requirement of *CHROMOMETHYLASE3* for Maintenance of CpXpG Methylation," *Science*, 2001, 292:2077-2080.

Lo, "Transformation by Iontophoretic Microinjection of DNA: Multiple Integrations Without Tandem Insertions," *Mol. Cell. Biol.*, 1983, 3(10):1803-1814.

Logie and Peterson, "Catalytic activity of the yeast SWI/SNF complex on reconstituted nucleosome arrays," *EMBO J.*, 1997, 16(22):6772-6782.

Logie et al., "The Core Histone N-Terminal Domains Are Required for Multiple Rounds of Catalytic Chromatin Remodeling by the SWI/SNF and RSC Complexes," *Biochemistry*, 1999, 38:2514-2522.

Long et al., "A member of the KNOTTED class of homeodomain proteins encoded by the *STM* gene of *Arabidopsis*," *Nature*, 1996, 379:66-69.

Lotan et al., "*Arabidopsis* LEAFY COTYLEDON1 Is Sufficient to Induce Embryo Development in Vegetative Cells," *Cell*, 1998, 93:1195-1205.

Luo et al., "Genes controlling fertilization-independent seed development in *Arabidopsis thaliana*," *Proc. Natl. Acad. Sci. USA*, 1999, 96:296-301.

Luo et al., "Expression and parent-of-origin effects for *FIS2*, *MEA*, and *FIE* in the endosperm and embryo of developing *Arabidopsis* seeds," *Proc. Natl. Acad. Sci. USA*, 2000, 97(19):10637-10642.

Mandel et al., "Molecular characterization of the *Arabidopsis* floral homeotic gene *APETALA1*," *Nature*, 1992, 360:273-277.

Martin et al., "Identification of mutants in metabolically regulated gene expression," *Plant J.*, 1997, 11(1):53-62.

Matsuoka et al., "The promoters of two-carboxylases in a $C_4$ plant (maize) direct cell-specific, light-regulated expression in a $C_3$ plant (rice)," *Plant J.*, 1994, 6(3):311-319.

McNabb et al., "Cloning of yeast *HAP5*: a novel subunit of a heterotrimeric complex required for CCAAT binding," *Genes & Development*, 1995, 9:47-58.

Meier et al., "Elicitor-Inducible and Constitutive in Vivo Footprints Indicate Novel *cis*-Acting Elements in the Promoter of a Parsley Gene Encoding Pathogenesis-Related Protein 1," *Plant Cell*, 1991, 3:309-315.

Meier et al., "The tomato *RBCS3A* promoter requires integration into the chromatin for correct organ-specific regulation," *FEBS Lett.*, 1997, 415:91-95.

Mizuguchi et al., "ATP-dependent Nucleosome Remodeling and Histone Hyperacetylation Syndergistically Facilitate Transcription of Chromatin," *J. Biol. Chem.*, 2001, 276(18):14773-14783.

Müller and Leutz, "Chromatin remodeling in development and differentiation," *Curr. Opin. Genet. Devel.*, 2001, 11:167-174.

Ng et al. "MBD2 is a transcriptional repressor belonging to the MeCP1 histone deacetylase complex," *Nature Genetics*, 1999, 23:58-61.

Ohad et al., "Mutations in *FIE*, a WD Polycomb Group Gene, Allow Endosperm Development without Fertilization," *Plant Cell*, 1999, 11:407-415.

Olesen and Guarente, "The HAP2 subunit of yeast CCAAT transcriptional activator contains adjacent domains for subunit association and DNA recognition: model for the HAP2/3/4 complex," *Genes & Development*, 1990, 4(9):1714-1729.

Preuss, "Chromatin Silencing and *Arabidopsis* Development: A Role for Polycomb Proteins," *Plant Cell*, 1999, 11:765-767.

Ray et al., "*Arabidopsis* floral homeotic gene BELL (*BEL1*) controls ovule development through negative regulation of AGAMOUS gene (*AG*)," *Proc. Natl. Acad. Sci, USA*, 1994:91:5761-5765.

Reiser et al., "The *BELL1* Gene Encodes a Homeodomain Protein Involved in Pattern Formation in the *Arabidopsis* Ovule Primordium," *Cell*, 1995, 83:735-742.

Roseman et al., "Long-Range Repression by Multiple Polycomb Group (PcG) Proteins Targeted by Fusion to a Defined DNA-Binding Domain in Drosophila," *Genetics*, 2001, 158:291-307.

Rotino et al., "Genetic engineering of parthenocarpic plants," *Nature Biotechnol.*, 1997, 15:1398-1401.

Sambrook et al., *Molecular Cloning —A Laboratory Manual*, Second Edition, 1989, Cold Spring Harbor Laboratory Press, New York, pp. 9.37-9.52.

Saurin et al., "A Drosophila Polycomb group complex includes Zeste and dTAFII proteins," *Nature*, 2001, 412:655-660.

Savidan et al., *The Flowering of Apomixis: From Mechanisms to Genetic Engineering*, 2001, Mexico, D.F.: CIMMYT, IRD, European Commission DG VI (FAIR), (Table of Contents only).

Sewack et al., "Binding of TATA Binding Protein to a Naturally Positioned Nucleosome Is Facilitated by Histone Acetylation," *Mol. Cell. Biol.*, 2001, 21(4):1404-1415.

Sheridan et al., "The *mac1* Gene: Controlling the Commitment to the Meiotic Pathway in Maize," *Genetics*, 1996, 142:1009-1020.

Shiina et al., "Identification of Promoter Elements Involved in the Cytosolic Ca2+ -Mediated Photoregulation of Maize *cab*-mI Expression," *Plant Physiol.*, 1997, 115:477-483.

Sif et al., "Purification and characterization of mSin3A-containing Brg1 and hBrm chromatin remodeling complexes," *Genes & Development*, 2001, 15:603-618.

Sjödahl et al., "Deletion analysis of the *Brassica napus* cruciferin gene *cru I* promoter in transformed tobacco: promoter during early and late stages of embryogenesis is influenced by *cis*-acting elements in partially separate regions," *Planta*, 1995, 197:264-271.

Smyth et al., "Early Flower Development in *Arabidopsis*," *Plant Cell*, 1990, 2:755-767.

Sonnhammer et al., "Pfam: A Comprehensive Database of Protein Domain Families Based on Seed Alignments," *Proteins: Structure, Function, and Genetics*, 1997, 28:405-420.

Sonnhammer et al., "Pfam: multiple sequence alignments and HMM-profiles of protein domains," *Nucl. Acids Res.*, 1998; 26(1):320-322.

Spillane et al., "Interaction of the *Arabidopsis* Polycomb group proteins FIE and MEA mediates their common phenotypes," *Current Biology*, 2000, 10:1535-1538.

Springer et al., "Sequence Relationships, Conserved Domains, and Expression Patterns for Maize Homologs of the Polycomb Group Genes $E(z)$, *esc*, and $E(Pc)^1$," *Plant Physiol.*, 2002, 128:1332-1345.

Thompson et al., "Germ Line Transmission and Expression of a Corrected HPRT Gene produced by Gene Targeting in Embryonic Stem Cells," *Cell*, 1989, 56:313-321.

Tie et al., "The *Drosophila* Polycomb Group proteins ESC and E(Z) bind directly to each other and co-localize at multiple chromosomal sites," *Development*, 1998, 56:313-321.

Treacy et al., "*Bnm*1, a *Brassica* pollen-specific gene," *Plant Mol. Biol.*, 1997, 34:603-611.

Tse et al., "Disruption of Higher-Order Folding by Core Histone Acerylation Dramatically Enhances Transcription of Nucleosomal Arrays by RNA Polymerase III," *Mol. Cell. Biol.*, 1998, 18(8):4629-4638.

Urao et al., "Molecular cloning and characterization of a gene that encodes a MYC-related protein in *Arabidopsis*," *Plant Mol. Biol.*, 1996, 32:571-576.

Van der Putten et al., "Efficient insertion of genes into the mouse germ line via retroviral vectors," *Proc. Natl. Acad. Sci. USA*, 1985, 82:6148-6152.

van der Vlag and Otte, "Transcriptional repression mediated by the human polycomb-group protein EED involves histone deacetylation," *Nature Genetics*, 1999, 23:474-478.

van der Vlag et al., "Transcriptional Repression Mediated by Polycomb Group Proteins and Other Chromatin-associated Repressors Is Selectively Blocked by Insulators," *J. Biol. Chem.*, 2000, 275(1):697-704.

Varga-Weisz et al., "Chromatin-remodelling factor CHRAC contains the ATPases ISWI and topoisomerase II," *Nature*, 1997, 388:598-602.

Verdaguer et al.,"Isolation and expression in transgenic tobacco and rice plants, of the cassava vein mosaic virus(CVMV) promoter," *Plant Mol. Biol.*, 1996, 31:1129-1139.

Vermaak et al., "Functional Analysis of the SIN3-Histone Deacetylase RPD3-RbAp48-Histone H4 Connection in the *Xenopus* Oocyte," *Mol. Cell. Biol.*, 1999, 19(9):5847-5860.

Vielle-Calzada et al., "Maintenance of genomic imprinting at the *Arabidopsis medea* locus requires zygotic *DDM1* activity," *Genes & Development*, 1999, 13:2971-2982.

Vignalia et al., "Distribution of acetylated histones resulting from Gal4-VP16 recruitment of SAGA and NuA4 complexes," *EMBO J.*, 2000, 19(11):2629-2640.

Vinkenoog et al., "Hypomethylation Promotes Autonomous Endosperm Development and Rescues Postfertilization Lethality in *fie* Mutants," *Plant Cell*, 2000, 12:2271-2282.

Wade et al. "Mi-2 complex couples DNA methylation to chromatin remodelling and histone deacetylation," *Nature Genetics*, 1999, 23:62-66.

Wade and Wolffe, "ReCoGnizing methylated DNA," *Nature Structural Biology*, 2001, 8(7):575-577.

Wakayama et al., "Full-term development of mice from enucleated oocytes injected with cumulus cell nuclei," *Nature*, 1998, 394-369-374.

Wakeley et al., "A maize pectin methylesterase-like gene, ZmC5, specifically expressed in pollen," *Plant Mol. Biol.*, 1998, 37:187-192.

Wang et al., "Histone Acetyltransferase Activity Is Conserved between Yeast and human GCN5 and is Required for Complementation of Growth and Transcriptional Activation," *Mol. Cell. Biol.*, 1997, 17(1):519-527.

Watson et al., "Ssn6-Tup1 interacts with class 1 histone deacetylases required for repression," *Genes & Development*, 2000, 14(21):2737-2744.

Weterings et al., "Regional Locailzation of Suspensor mRNAs during Early Embryo Development," *Plant Cell*, 2001, 13:2409-2425.

Willmut et al., "Viable offspring derived from fetal and adult mammalian cells," *Nature*, 1997, 385:810-813.

Wu et al., "Functional analysis of HD2 histone deacetylase homologues in *Arabidopsis thaliana*," *Plant J.*, 2000, 22(1):19-27.

Yadegari et al., "Mutations in the *FIE* and *MEA* Genes That Encode Interacting Polycomb Proteins Cause Parent-of-Origin Effects on Seed Development by Distinct Mechanisms," *Plant Cell*, 2000, 12:2367-2381.

Yamamoto et al., "Characterization of *cis*-Acting Sequences Regulating Root-Specific Gene Expression in Tobacco," *Plant Cell*, 1991, 3:371-382.

Zhang et al., "DNA Sequences That Activate Isocitrate Lyase Gene Expression during Late Embryogenesis and during Postgerminative Growth," *Plant Physiol.*, 1996, 110:1069-1079.

Riechmann et al., "A genomic perspective on plant transcription factors," *Current Opinion in Plant Biology*, (2000), 3:423-434.

Schwechheimer et al., "Transactivation of a target gene through feedforward loop activation in plants," *Funt Integr Genomics* (2000), 1:35-43.

Yang et al., "Expression of the REB transcriptional activator in rice grains improves the yield of recombinant proteins whose genes are controlled by a *Reb*-responsive promoter," *PNAS*, (Sep. 25, 2001), 98(20):11438-11443.

GenBank Accession No. D50643, dated Mar. 23, 2002.
GenBank Accession No. J02798, dated Oct. 11, 2001.
GenBank Accession No. J05212, dated Jun. 1, 1995.
GenBank Accession No. K00821, dated Apr. 27, 1993.
GenBank Accession No. L05934, dated Oct. 22, 1993.
GenBank Accession No. M28156, dated Oct. 18, 2005.
GenBank Accession No. M63985, dated Apr. 27, 1993.
GenBank Accession No. S44893, dated May 8, 1993.
GenBank Accession No. U09118, dated Jan. 19, 2000.
GenBank Accession No. U09119, dated Jul. 24, 2001.
GenBank Accession No. U39944, dated Feb. 4, 2003.
GenBank Accession No. U76670, dated Jan. 23, 1997.
GenBank Accession No. U93215, dated Feb. 27, 2002.
GenBank Accession No. X15121, dated Feb. 10, 1999.
GenBank Accession No. Z17657, dated Nov. 10, 1992.
GenBank Accession No. AF096096, dated Jan. 25, 1999.
GenBank Accession No. AF129516, dated Apr. 6, 1999.
GenBank Accession No. AF233296, dated Apr. 24, 2000.
GenBank Accession No. AL161566, dated Apr. 16, 2005.

Kwaks TH et al., "Targeting of a histone acetyltransferase domain to a promoter enhances protein expression levels in mammalian cells." *J Biotechnol.* Jan. 12, 2005; 115(1): 35-46.

Verschure PJ et al., "In Vivo HP1 Targeting Causes Large-Scale Chromatin Condensation and Enhanced Histone Lysine Methylation." *Mol Cell Biol.* Jun. 2005; 25(11): 4552-64.

Chiu YH et al., "A targeted histone acetyltransferase can create a sizable region of hyperacetylated chromatin and counteract the propagation of transcrptionally silent chromatin." *Genetics*, Sep. 2003; 165(1): 115-25.

de Pater et al., "Characterization of a zinc-dependent transcriptional activator from *Arabidopsis*," *Nucleic Acids Research*, 1996, 24(23):4624-4631.

Krumm et al., "Long distance transcriptional enhancement by the histone acetyltransferase PCAF," *Proc. Natl. Acad. Sci. USA*, 1998, 95:13501-13506.

Kwaks TH et al., "Targeting of a histone acetyltransferase domain to a promoter enhances protein expression levels in mammalian cells." *J Biotechnol.* Jan. 12, 2005; 115(1): 35-46.

Liu et al., "Transcription Factors and their genes in higher plants" *Eur. J. Biochem.*, 1999, 262:247-257.

Meshi et al., "Plant Transcription Factors," *Plant Cell Physiol.*, 1995, 36(8):1405-1420.

Ptashne et al., "Transcriptional activation by recruitment," *Nature*, 1997, 386:569-577.

Remacle et al., "Three class of mammalian transcription activation domain stimulate transcription in *Schizosaccharamyces pombe*," *EMBO J.*, 1997, 16(18):5722-4729.

Sauer et al., "Mechanism of transcriptional activation: differences and similarities between yeast, Drosophila, and man," *Curr. Op. Genet. Dev.*, 1997, 7:176-181.

Triezenberg et al., "Structure and function of transcriptional activation domains," *Curr. Op. Genet. Dev.*, 1995, 5:190-196.

* cited by examiner

CHIMERIC HISTONE ACETYLTRANSFERASE POLYPEPTIDES

CROSS-REFERENCE TO RELATED APPLICATIONS

This application claims priority to U.S. application Ser. No. 60/300,135, filed on Jun. 22, 2001.

TECHNICAL FIELD

This invention relates to methods and materials for analyzing and modulating gene expression. In particular, the invention features chimeric histone acetyltransferase polypeptides that can be used to determine gene expression profiles in specific cells, and to modulate gene expression in specific cells.

BACKGROUND

Genes often are differentially expressed during the development of an organism, and in particular cells in an organism. Understanding and manipulating an organism's temporal and spatial gene expression profile can be useful for developing new and improved biological products and therapies. Among the array of regulatory mechanisms that affect the gene expression profile of an organism, chromatin remodeling has an important role.

Eukaryotic DNA is tightly packaged into chromatin. The most basic element of DNA packaging is the nucleosome, which consists of an octamer of histone proteins wrapped by about 146 nucleotide base pairs. The compaction of eukaryotic DNA into nucleosomes and the formation of nucleosome arrays present natural barriers to genetic regulatory proteins, and to enzymes that interact with DNA. Chromatin-associated protein complexes reportedly can, among other things, stabilize and destabilize nucleosomal DNA and thereby affect nuclear processes that use DNA as a substrate (e.g., transcription, replication, DNA repair, and DNA organization) as well as regulators of these processes.

Some chromatin-associated protein complexes are reported to use the energy of ATP hydrolysis to increase histone mobility, and to thereby change the accessibility of certain nucleosomal DNA to enzymes that process genetic information and to genetic regulatory proteins. It is thought that ATP-dependent chromatin-remodeling protein complexes can have a role in both gene activation and repression. Researchers have reported the existence of ATP-dependent chromatin-remodeling protein complexes in organisms including yeast (e.g., SWI/SNF, RSC, ISW1, ISW2, and Ino 80), Drosophila (e.g., dSWI/SNF, ACF, CHRAC, and NURF), and human (e.g., hSWI/SNF, NuRD, RSF, and ACF).

Other chromatin-associated protein complexes are reported to change chromatin structure by covalently modifying histones (e.g., by adding or removing acetyl, methyl, phosphate or ubiquitin). It is thought that by covalently modifying histones, these protein complexes can affect chromatin structure and thereby change the accessibility of nucleosomal DNA to enzymes that process genetic information and to genetic regulatory proteins. Some of these histone-modifying protein complexes also are thought to affect the activity of ATP-dependent chromatin-remodeling complexes.

For example, some histone-modifying chromatin-associated protein complexes reportedly contain a polypeptide subunit having histone acetyltransferase ("HAT") enzymatic activity. Such protein complexes are, in general, thought to have a role in activating transcription. Researchers have reported the existence of polypeptides having HAT enzymatic activity in organisms including yeast, Tetrahymena, and humans.

As another example, some histone-modifying chromatin-associated protein complexes reportedly contain a polypeptide subunit having histone deacetylase ("HDAC") enzymatic activity. Such protein complexes are, in general, thought to have a role in repressing transcription. Researchers have reported the existence of polypeptides having HDAC enzymatic activity in organisms including yeast, C. elegans, Drosophila, Xenopus, chicken, mouse, human and maize.

SUMMARY

The present invention relates to chimeric histone acetyltransferase ("HAT") polypeptides useful for determining gene expression profiles in specific cell types, or for modulating gene expression in specific cell types. For example, chimeric HAT polypeptides can be used to affect gene expression to achieve desirable results, such as enhancing expression of specific genes in a eukaryotic organism. Chimeric HAT polypeptides contain a polypeptide segment that has HAT enzymatic activity and a polypeptide segment that is similar or identical to a subunit a of chromatin-associated protein complex having histone deacetylase ("HDAC") enzymatic activity.

Thus, the invention features chimeric polypeptides that contain: 1) a first polypeptide segment that exhibits histone acetyltransferase activity, and 2) a second polypeptide segment having 40% or greater (e.g., at least 40%, at least 60%, at least 80% and at least 90%) sequence identity to a subunit of a histone deacetylase chromatin-associated protein complex (e.g., a subunit that exhibits scaffold activity, a subunit that exhibits DNA binding activity, a subunit that exhibits ATPase-dependent helicase activity, and a subunit that exhibits histone deacetylase activity). The first and second polypeptide segments are arranged such that a terminus of the second polypeptide segment is linked to a terminus of the first polypeptide segment via at least one covalent bond.

In some embodiments, the first and second polypeptide segments can be directly linked via a peptide bond. In such embodiments the C-terminal amino acid of the first polypeptide segment can be linked to the N-terminal amino acid of the second polypeptide segment. Alternatively, the N-terminal amino acid of the first polypeptide segment can be linked to the C-terminal amino acid of the second polypeptide segment. In some embodiments, the first and second polypeptide segments can be indirectly linked via one or more (e.g., 1 to 50, and 10 to 50) intervening amino acids that are situated between the first and second polypeptides. In such embodiments, the C-terminal amino acid of the first polypeptide segment can be linked to an intervening amino acid, and the N-terminal amino acid of the second polypeptide segment can be linked to an intervening amino acid. Alternatively, the N-terminal amino acid of the first polypeptide segment can be linked to an intervening amino acid, and the C-terminal amino acid of the second polypeptide segment can be linked to an intervening amino acid. In some embodiments, the intervening amino acids include at least one alanine residue and/or at least one glycine residue.

The invention also features nucleic acid constructs that encode such chimeric polypeptides, and eukaryotic organisms that include such chimeric polypeptides.

The invention also features eukaryotic organisms that contain a nucleic acid that encodes a chimeric polypeptide having: 1) a first polypeptide segment that exhibits histone acetyltransferase activity; and 2) a second polypeptide segment that has 40% or greater sequence identity to a subunit of a histone deacetylase chromatin-associated protein complex. The first and second polypeptide segments of the encoded chimeric polypeptide are arranged such that a terminus of the second polypeptide segment is covalently linked to a terminus of the first polypeptide segment. The nucleic acid can be operably linked to a promoter.

The invention also features eukaryotic organisms that contain: 1) a first nucleic acid construct having a first promoter and a transcription activator element operably linked to a coding sequence that encodes a chimeric polypeptide, and 2) a second nucleic acid construct having a second promoter conferring cell type-specific transcription operably linked to a coding sequence for a polypeptide that binds the transcription activator element. The encoded chimeric polypeptide has: 1) a first polypeptide segment that exhibits histone acetyltransferase activity, and 2) a second polypeptide segment that has 40% or greater sequence identity to a subunit of a histone deacetylase chromatin-associated protein complex. The first and second polypeptide segments of an encoded chimeric polypeptide are arranged such that a terminus of the second polypeptide segment is covalently linked to a terminus of the first polypeptide segment. In some embodiments, the organism is an animal. In other embodiments the organism is a plant (e.g., a monocot such as corn and rice, or a dicot such as soybean and rape). In some embodiments, the plant contains a mutation or agent that alters (i.e., increases or decreases) the DNA methylation state in the plant relative to a corresponding plant that lacks said agent or mutation. In some embodiments, the mutation is in a C5 DNA methyltransferase (a.k.a. cytosine C5 DNA methyltransferase) gene. In some embodiments, the agent is an antisense nucleic acid. In some embodiments, the agent affects expression of a C5 DNA methyltransferase gene.

The invention also features methods for detecting the expression of one or more genes in a eukaryote. The methods involve isolating macromolecules from one or more specific cells in a eukaryote (e.g., a plant or an animal) that contains a nucleic acid construct in which a promoter is operably linked to a coding sequence that encodes a chimeric polypeptide, and then determining the presence or amount of at least one of the macromolecules in at least one of the specific cells. The encoded chimeric polypeptide has: 1) a first polypeptide segment that exhibits histone acetyltransferase activity, and 2) a second polypeptide segment that has 40% or greater sequence identity to a subunit of a histone deacetylase chromatin-associated protein complex. The first and second polypeptide segments of the encoded chimeric polypeptide are arranged such that a terminus of the second polypeptide segment is covalently linked to a terminus of the first polypeptide segment. In some embodiments, the macromolecules are polypeptides. In some embodiments, the macromolecules are nucleic acids. In some embodiments, the promoter confers cell-type specific transcription in a plant reproductive tissue (e.g., ovule, central cell, endosperm, embryo, and zygote). In some embodiments, the promoter confers cell-type specific transcription in a plant vegetative tissue.

In some embodiments, the eukaryote also contains a second nucleic acid construct. In such embodiments, the first nucleic acid construct has a recognition site for a transcriptional activator operably linked to the promoter and the coding sequence. The second nucleic acid construct has a second promoter conferring cell-type specific transcription that is operably linked to a coding sequence for a polypeptide that binds the recognition site for the transcriptional activator.

The invention also features methods for modulating gene expression in a eukaryote. The methods involve making a eukaryote (e.g., a plant or an animal) having a nucleic acid construct in which a cell-type specific promoter is operably linked to a coding sequence that encodes a chimeric polypeptide. The encoded chimeric polypeptide has: 1) a first polypeptide segment that exhibits histone acetyltransferase activity, and 2) a second polypeptide segment that has 40% or greater sequence identity to a subunit of a histone deacetylase chromatin-associated protein complex. The first and second polypeptide segments of the encoded chimeric polypeptide are arranged such that a terminus of the second polypeptide segment is covalently linked to a terminus of the first polypeptide segment. The eukaryote exhibits modulated gene expression in cells in which the promoter confers cell-type specific transcription. In some embodiments, the eukaryote has compositional alterations relative to a corresponding organism that lacks said nucleic acid construct. In some embodiments, the eukaryote has developmental alterations relative to a corresponding organism that lacks said nucleic acid construct. In some embodiments, the eukaryote has phenotypic alterations relative to a corresponding organism that lacks said nucleic acid construct.

In some embodiments, the organism is a plant. In some embodiments, the promoter confers cell-type specific transcription in a plant reproductive tissue (e.g., ovule, central cell, endosperm, embryo, and zygote). In some embodiments, the promoter confers cell-type specific transcription in a plant vegetative tissue. In some embodiments, the plant contains a mutation or agent that alters (e.g., increases or decreases) the DNA methylation state in the plant relative to a corresponding plant that lacks said agent or mutation. In some embodiments, the mutation is in a C5 DNA methyltransferase gene. In some embodiments, the agent is an antisense nucleic acid. In some embodiments, the agent affects expression of a C5 DNA methyltransferase gene. In some embodiments, modulated gene expression alters seed development. In some embodiments modulated gene expression alters embryo development. In some embodiments, modulated gene expression alters endosperm development. In some embodiments, modulated gene expression alters seed yield by mass.

The invention also features methods for modulating gene expression in a eukaryote that involve making a eukaryote (e.g., a plant or an animal) that has 1) a first nucleic acid construct having a first promoter and a transcription activator element operably linked to a coding sequence that encodes a chimeric polypeptide, and 2) a second nucleic acid construct having a second promoter conferring cell type-specific transcription operably linked to a coding sequence for a polypeptide that binds the transcription activator element. The encoded chimeric polypeptide has: 1) a first polypeptide segment that exhibits histone acetyltransferase activity, and 2) a second polypeptide segment that has 40% or greater sequence identity to a subunit of a histone deacetylase chromatin-associated protein complex. The first and second polypeptide segments of the encoded chimeric polypeptide are arranged such that a terminus of the second polypeptide segment is covalently linked to a terminus of the first polypeptide segment. The eukaryote exhibits modulated gene expression in cells in which the second promoter confers cell-type specific transcription. In some embodiments, the eukaryote has compositional alterations relative to a corresponding organism that lacks said nucleic acid construct. In some embodiments, the eukaryote has developmental alterations relative to a corresponding organism that lacks said nucleic acid construct. In some embodiments, the eukaryote has phenotypic alterations relative to a corresponding organism that lacks said nucleic acid construct.

In some embodiments, the organism is a plant. In some embodiments, the second promoter confers cell-type specific transcription in a plant reproductive tissue (e.g., ovule, central cell, endosperm, embryo, and zygote). In some embodiments, the second promoter confers cell-type specific transcription in a plant vegetative tissue. In some embodiments, the plant contains a mutation or agent that alters (e.g., increases or decreases) the DNA methylation state in the plant relative to a corresponding plant that lacks said agent or mutation. In some embodiments, the mutation is in a C5 DNA methyltransferase gene. In some embodiments, the agent is an antisense nucleic acid. In some embodiments, the agent affects expression of a C5 DNA methyltransferase gene. In some embodiments, modulated gene expression alters seed development. In some embodiments modulated gene expression alters embryo development. In some embodiments, modulated gene expression alters endosperm development. In some embodiments, modulated gene expression alters seed yield by mass.

The invention also features methods for making a genetically modified eukaryote. The methods involve making a first eukaryote (e.g., a plant or an animal) that has a first nucleic acid construct having a first promoter and a transcription activator element operably linked to a coding sequence. The coding sequence encodes a first polypeptide segment and a second polypeptide segment. The first polypeptide segment exhibits histone acetyltransferase activity, and the second polypeptide segment has 40% or greater sequence substantially identical to a subunit of a histone deacetylase chromatin-associated protein complex. The first and second polypeptide segments of the encoded chimeric polypeptide are arranged such that a terminus of the second polypeptide segment is covalently linked to a terminus of the first polypeptide segment. The methods also involve making a second eukaryote that has a second nucleic acid construct having a promoter that confers embryo-specific transcription operably linked to a coding sequence encoding a polypeptide that binds the transcription activator element of the first nucleic acid construct. The method also involves crossing the first and second eukaryotes to form genetically modified progeny that are sterile.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description.

DETAILED DESCRIPTION

This invention features chimeric histone acetyltransferase ("HAT") polypeptides. Chimeric HAT polypeptides can be used to determine and modulate gene expression profiles in eukaryotic organisms.

Chimeric Polypeptides

A chimeric HAT polypeptide contains at least two polypeptide segments: a first polypeptide segment that exhibits HAT enzymatic activity, and a second polypeptide segment that is substantially identical to a subunit of those chromatin-associated protein complexes having histone deacetyltransferase ("HDAC") activity. A chimeric HAT polypeptide typically is not found in nature.

First Polypeptide Segment

A polypeptide segment that exhibits HAT enzymatic activity is a suitable first polypeptide segment of a chimeric HAT polypeptide. Whether a first polypeptide segment exhibits HAT enzymatic activity can be determined by testing either the polypeptide segment or the chimeric HAT polypeptide using an assay that measures the transfer of an acetyl functional group from an acetyl donor such as acetyl CoA to a histone polypeptide or polypeptide segment. See e.g., Brownell, J. and Allis, C. D. (1995) *Proc. Natl. Acad. Sci.* 92, 6364-6368. This assay can be used to screen candidate polypeptide segments for HAT enzymatic activity, and to test chimeric polypeptides for HAT enzymatic activity.

In some embodiments, a first polypeptide segment has an amino acid sequence that corresponds to the amino acid sequence of one of the following polypeptides: yeast Esa1, Gcn5, Sas3, yTAFII130, ELP3, HAT1 or Hpa2; *Drosophila* dGcn5, dTAFII230 or MOF; *Tetrahymena* p55; or human hGcn5, p300/CPB, PCAF, Tip60, hTAFII250, TFIII90/110/220, SRC-1 or ACTR. In other embodiments, a first polypeptide segment can have an amino acid sequence with substitutions, insertions or deletions relative to one of the above-mentioned polypeptides. Any polypeptide segment having HAT enzymatic activity is suitable as a first polypeptide segment, irrespective of the number or character of amino acid insertions, deletions, or substitutions. Thus, in some embodiments, the amino acid sequence of a first polypeptide segment corresponds to less than the full-length sequence (e.g., a HAT functional domain) of one of the above-mentioned polypeptides.

One of skill will recognize that individual substitutions, deletions or additions to a polypeptide that alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (O);
4) Arginine (R), Lysine (K);
5) Isoleucine (I), Leucine (L), Methionine (M), Valine (V); and
6) Phenylalanine (F), Tyrosine (Y), Tryptophan (W). (see e.g., Creighton, Proteins (1984)).

Other suitable candidates for first polypeptide segments can be identified by homologous polypeptide sequence analysis. A similar analysis can be applied to identify suitable candidates for second polypeptide segments. HAT amino acid sequence families are known to be conserved. For example, plant histone acetyltransferase genes can be identified by BLAST or PSI-BLAST analysis of nonredundant protein databases using known plant, yeast and/or animal histone acetyltransferase amino acid sequences. Homologous polypeptide sequence analysis involves the identification of conserved regions in a template polypeptide, also referred to herein as a subject polypeptide. Conserved regions can be identified by locating a region within the primary amino acid sequence of a template polypeptide that is a repeated sequence, forms some secondary structure such as helices, beta sheets, etc., establishes positively or negatively charged domains and represents a protein motif or domain. See e.g., Bouckaert et al., U.S. Ser. No. 60/121, 700, filed Feb. 25, 1999, and the Pfam web site describing consensus sequences for a variety of protein motifs and domains at sanger.ac.uk/Pfam/ and genome.wustl.edu/Pfam/. The information included in the Pfam database is described in Sonnhammer et al., *Nucl Acids Res* 26:320-322 (1998), and in Sonnhammer et al., *Proteins* 28:405-420 (1997); Bateman et al., *Nucl Acids Res* 27:260-262 (1999), and Sonnhammer et al., *Proteins* 28:405-20 (1997). From the Pfam database, consensus sequences of protein motifs and domains can be aligned with the template polypeptide sequence to determine conserved region(s).

Conserved regions also can be determined by aligning sequences of the same or related polypeptides from closely related plant species. Closely related plant species preferably are from the same family. Alternatively, alignment are performed using sequences from plant species that are all monocots or are all dicots. In some embodiments, alignment of sequences from two different plant species is adequate. For example, sequences from canola and *Arabidopsis* can be used to identify one or more conserved regions. Such related polypeptides from different plant species need not exhibit an extremely high sequence identity to aid in determining conserved regions. For example, polypeptides that exhibit about 35% sequence identity can be useful to identify a conserved region. Typically, conserved regions of related proteins exhibit at least 40% sequence identity; or at least about 50%; or at least 60%, or at least 70%, at least 80%, or at least 90% sequence identity. In some embodiments, a conserved region of target and template polypeptides exhibit at least 92, 94, 96, 98, or 99% sequence identity. Sequence identity can be either at the amino acid or nucleotide level.

In some embodiments, a first polypeptide segment is the polypeptide encoded by the maize HAC101, HAC104, HAC105, HAC107 or HAC109 gene or a homolog thereof. The maize HAC101 gene belongs to the CREB-Binding Protein family of transcriptional co-activators with histone acetyltransferase activity. Maize HAC104 is most homologous to the GCN5 family of HATs in yeast and animals. Maize HAC105 is most homologous to the ESA1 related family of HATs in yeast and animals. Maize HAC107 is most homologous to the ELP3 related family of HATs in yeast and animals. Maize HAC109 is most homologous to the HAT1 related family of HATs in yeast and animals. In other embodiments, polypeptides having modifications relative to the above polypeptides are suitable first polypeptide segments.

In some embodiments, a first polypeptide segment is the polypeptide encoded by the *Arabidopsis* HAC1, HAC2, HAC3, HAC4, HAC7 or HAC8 gene or a homolog thereof. *Arabidopsis* HAC2 and HAC4 genes encode HATs that are homologous to human CREB-binding proteins. *Arabidopsis* HAC3 is homologous to yeast Gcn5. *Arabidopsis* HAC1 is homologous to yeast HAT1. In other embodiments, polypeptides having modifications relative to the above polypeptides are suitable first polypeptide segments.

Exemplary amino acid sequences of HAT polypeptides are shown in Table 6.

Yet other first polypeptide segments can be synthesized on the basis of consensus HAT functional domains. See e.g., Table 13.

Second Polypeptide Segment

Chimeric polypeptides of the invention have a second polypeptide segment that is covalently linked to the first polypeptide segment. A second polypeptide segment can have substantial identity, or can be identical, to a subunit of certain chromatin-associated protein ("CAP") complexes, i.e., those CAP complexes having a subunit that exhibits histone deacetylase activity ("CAP/HDAC complexes"). CAP/HDAC complexes include, for example, polycomb group (PcG) complexes, SIN3/HDAC-containing complexes, Mad-Max complexes, Tup1-Ssn6 complexes, DNMT1 complexes, MeCP1 and MeCP2 complexes, MBD complexes, and Ikaros-Aiolos-containing complexes. Amino acid sequences of subunits of CAP/HDAC complexes generally are conserved among different species.

CAP/HDAC complexes can be distinguished from other chromatin-associated protein complexes by the presence of a subunit that exhibits histone deacetylase activity. Alternatively, CAP/HDAC complexes can be distinguished from other chromatin-associated protein complexes by the presence of a subunit that exhibits sequence homology to known histone deacetylase proteins. In contrast, other chromatin-associated protein complexes either have histone acetyltransferase activity or have neither HAT nor HDAC activity. CAP/HDAC complexes also can be distinguished from other chromatin-associated protein complexes by their effect, in vitro or in vivo, on gene expression. Transcription from genes in nucleosomes to which CAP/HDAC complexes are bound typically is reduced or even eliminated. In contrast, chromatin-associated protein complexes having a HAT subunit typically facilitate increased transcription from genes in nucleosomes to which such complexes are bound. CAP/HDAC complexes can be distinguished from transcription complexes by the lack of any subunit that interacts directly with RNA polymerase II. CAP/HDAC complexes can be readily distinguished from nucleosomes because CAP/HDAC complexes do not have histones as subunits of the complex.

Whether a particular complex possesses a subunit that exhibits HDAC activity can be determined by testing a putative CAP/HDAC complex or its subunits, for HDAC activity. HDAC activity can be determined by an assay that measures the removal of an acetyl group from a histone polypeptide or histone polypeptide segment. See e.g., van der Vlag, J. and Otte, A. P. *Nature Genetics* 25, 474-478 (1999). This assay can be used to screen subunits of candidate CAP complexes for HDAC activity. Alternatively, a CAP complex can be shown to possess a subunit having HDAC activity by sequence identity to a subunit of a known CAP/HDAC complex, as described herein.

Once a CAP complex has been determined to possess a histone deacetylase as one subunit of the complex, then all subunits of that particular CAP/HDAC complex can be tested for their suitability as a second polypeptide segment. Polypeptides can be identified as subunits of a CAP/HDAC complex by their co-purification with the complex.

In some embodiments, the second polypeptide segment is the subunit that is HDAC itself. Such subunits can be identified using the above-described assay for HDAC enzymatic activity. The following polypeptides having HDAC enzymatic activity have been identified: yeast RPD3, HDA1, HOS1, HOS2, and HOS3; *C. elegans* HDA1, HDA2, HDA3; *Drosophila* dHDAC1, dHDAC2, dHDAC3, and dHDA2; *Xenopus* HDm; chicken HDAC1, HDAC2, and HDAC3; mouse HDAC1, HDAC2, HDAC3, mHDA1, and mHDA2; human HDAC1, HDAC2, HDAC3, HDAC4, HDAC5, HDAC6, HDAC7, and HDAC8; and maize RPD3 and HD2. See e.g., Cress W. D. and Seto, E. (2000) *J. Cell. Physiol.* 184, 1-16. All of the above HDAC polypeptides are suitable for use as the second polypeptide segment, as are homologous polypeptides and recombinant polypeptides (i.e., polypeptides having amino acid insertions, deletions, or substitutions) having greater than 40% sequence identity.

Subunits of CAP/HDAC complexes also can be identified by coimmunoprecipitation using antibodies against known CAP/HDAC subunits. Purification of CAP/HDAC subunits using coimmunoprecipitation has been described, for example, in: Jones P. L. et al. *Nature Genet* 19, 187-191 (1998); van der Vlag, J. and Otte, A. P. *Nature Genetics* 25, 474-478 (1999); Wade, P. A. et al. *Nature Genetics* 23, 62-66 (1999); Ng, H. H. et al. *Nature Genetics* 23, 58-61 (1999); and Spillane C. et al. *Curr Biol.* 10, 1535-1538 (2000).

Subunits of CAP/HDAC complexes also can be identified by yeast two-hybrid analyses using hybrid polypeptides containing known CAP/HDAC subunits. Use of the yeast two-hybrid system to identify CAP/HDAC subunits has been described, for example, in: Yadegari. R. et al. *Plant Cell* 12, 2367-2381 (2000); and Spillane C. et al. *Curr Biol.* 10, 1535-1538 (2000).

In some instances, suitable second polypeptide segments can be synthesized on the basis of consensus functional domains and/or conserved regions in polypeptides that are homologous subunits of a CAP/HDAC complex. Consensus domains and conserved regions can be identified by homologous polypeptide sequence analysis as described herein. The suitability of such synthetic polypeptides for use as a second polypeptide segment can be evaluated by the techniques described herein, or by evaluating the ability of a synthetic polypeptide to effectively substitute for a corresponding subunit when expressed in a eukaryotic organism.

Many CAP/HDAC complexes and CAP/HDAC complex subunits are known to be conserved in plants, fungi and animals. Subunits of a CAP/HDAC complex in one organism can be used to identify homologous subunits in another organism, e.g., homologs of a subunit of a known CAP/HDAC complex can be identified by performing a BLAST query on a database of protein sequences. Those proteins in the database that have greater than 40% sequence identity are candidates for further evaluation for suitability as a second polypeptide segment. For example, the *Arabidopsis* polycomb group proteins FIE and MEA have significant sequence identity to the *Drosophila* proteins extra sex combs and enhancer of zeste. If desired, manual inspection of such candidates can be carried out in order to narrow the number of candidates for further evaluation. Manual inspection is carried out by selecting those candidates that appear to have domains suspected of being present in subunits of CAP/HDAC complexes.

Further evaluation can be carried out by creating a chimeric polypeptide having the candidate as the second segment, inserting the chimeric polypeptide into a eukaryotic organism, and evaluating the phenotypic effect of the chimeric polypeptide in the organism. If the desired phenotypic effect(s) is observed, the candidate is suitable as a second polypeptide segment.

A percent identity for any subject nucleic acid or amino acid sequence (e.g., any of the chimeric polypeptide first polypeptide segments, or second polypeptide segments described herein) relative to another "target" nucleic acid or amino acid sequence can be determined as follows. First, a target nucleic acid or amino acid sequence of the invention can be compared and aligned to a subject nucleic acid or amino acid sequence using the BLAST 2 Sequences (B12seq) program from the stand-alone version of BLASTZ containing BLASTN and BLASTP (e.g., version 2.0.14). The stand-alone version of BLASTZ can be obtained at fr.com or ncbi.nlm.nih.gov. Instructions explaining how to use BLASTZ, and specifically the B12seq program, can be found in the 'readme' file accompanying BLASTZ. The programs also are described in detail by Karlin et al. (*Proc. Natl. Acad. Sci. USA,* 87:2264 (1990) and 90:5873 (1993)) and Altschul et al. (*Nucl. Acids Res.,* 25:3389 (1997)).

B12seq performs a comparison between a subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains.

The percent identity over a particular length is determined by counting the number of matched positions over that particular length, dividing that number by the length and multiplying the resulting value by 100. For example, if (i) a 500 amino acid target sequence is compared to a subject amino acid sequence, (ii) the B12seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180÷200×100=90). In some embodiments, the amino acid sequence of a second polypeptide segment has 40% sequence identity to the amino acid sequence of a subunit of a CAP/HDAC complex. In some embodiments, the amino acid sequence of a second polypeptide segment has greater than 40% sequence identity (e.g., >80%, >70%, >60%, >50% or >40%) to the amino acid sequence of a subunit of a CAP/HDAC complex.

It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

A partial list of nucleic acids encoding proteins that are subunits of CAP/HDAC complexes is shown in Table 1. The nucleic acids shown in Table 1 encode proteins that are subunits of CAP/HDAC complexes often referred to as polycomb group (PcG) complexes. Such proteins are candidates to be the second polypeptide segment.

TABLE 1

Polycomb Group Subunits

| Genes | GI number-Source |
|---|---|
| Additional sex combs (Asx) | GI:3292939 |
| Cramped | GI:5869804 |
| Enhancer of Zeste (E(z)) | GI:404864 |
| Enhancer of polycomb | GI:3757890 |
| Extra sex combs (Esc) | GI:2133657 or GI:1050997 |
| At Epl1 | GI:9989052 |
| At Epl2 | GI:3152596 |
| ZmEpl01 | GI:20152912 |
| Multi sex combs (mxc) | GI:6746602 |
| Pleiohomeotic (pho) | GI:3258627 |
| Polycomb (Pc) | GI:129718 |
| Polycomb-like (Pcl) | GI:521181 |
| Polyhomeotic distal (mouse) | GI:1490546 |
| Polyhomeotic proximal (php) | GI:730323 |
| Posterior sexcombs (Psc) | GI:548613 or GI:103177 |
| Sexcomb extra (Sce) | sequence unknown |
| Sex comb on midleg (Scm) | GI:1293574 |
| Suppressor-2 of zeste | GI:236137 (partial) |
| Supressor of zeste 12 Su(z)12 | GI:8131946 |
| Su(z)2(D) | sequence unknown |
| Super sex combs (sxc) | sequence unknown |
| At Fis2 | GI:4185501 |
| At Emf2 | GI:14276050 |
| At Vrn2 | GI:16945788 |
| At MEA; At CLF; At E(Z)-likeA1; Mez1; Mez2; Mez3 | GI:3089625 |
| At Fie | GI:4567095 |
| Zm Fie1 | GI:18032004 |
| Zm Fie2 | GI:18032006 |

In some embodiments, a second polypeptide segment is the polypeptide encoded by the *Arabidopsis Mea, FIS2, FIE, At E(Z)-like A1, curly-leaf*, or *TSO1-like* genes or homologs thereof. Polypeptides having modifications relative to these polypeptides also can be suitable second polypeptide segments.

Also useful are proteins that are subunits of SIN3/HDAC complexes, including, for example, Sin3, Rpd3 RbAp48, RbAp46, NcoR and SMRT. See e.g., Wolffe, A. P. et al., *Mol. Cell Biol.*, 19:5847-5860 (1999). A partial list of nucleic acids encoding proteins that are subunits of SIN3/HDAC complexes is shown in Table 2. Polypeptides having modifications relative to these polypeptides also are suitable second polypeptide segments.

TABLE 2

Subunits of Sin3/HDAC Complexes

| Genes | GI number |
|---|---|
| Sin3 | GI:9624449 |
| STB1 (Sin3 binding protein) | GI:988311 |
| STB2 (Sin3 binding protein) | GI:988309 |
| Rpd3 | GI:417699 |
| SDS3 (suppressor of defective silencing 3) | GI:1480732 |
| HD2A | GI:7489751 |
| HD2B | GI:7716948 |
| HDAC1 | GI:2498443 |
| HDAC2 | GI:3023939 |
| RbAp48 | GI:3309245 |
| RbAp46 | GI:4506439 |
| SMRT | GI:2136312 |
| Tup1 | GI:83454 |
| Ume6 | GI:6320413 |
| N-CoR1 and 2 (nuclear receptor corepressor) | GI:5454138; GI:12643957 |
| Ssn6 | GI:117936 |
| Mad1 | GI:1708908 |
| Mnt | GI:6754718 |
| Mxi1 | GI:1709194 |
| Rox | GI:3914034 |
| PSF (polypyrimidine tract-binding protein-associated splicing factor) | GI:10442545 |
| NonO/p54(nrb) | GI:13124797 |
| Ikaros | GI:3915731 |
| Aiolos | GI:2150044 |
| MBD1 | GI:7305259 |
| MBD2 | GI:5929756 |
| MBD3 | GI:4505119 |
| MBD4 | GI:6754652 |
| MeCP1 (PCM1) | GI:7710141 |
| MeCP2 | GI:1708973 |
| Mi-2 | GI:4557451 |
| SAP18 | GI:11433775; 5032067 |
| SAP30 | GI:11436724; 4506783 |
| MTA-like | GI:6754644 |
| KRAB-ZFP (Kruppel associated box) | GI:9625008 |

Also useful are proteins that are subunits of Mad-Max complexes, another group of CAP/HDAC complexes. Examples of Mad-Max complex subunits include Max-Mad-Mxi-Myc (basic HLH), mSin3a/B, HDAC1/2, N—CoR (nuclear receptor corepressor), and SMRT (silencing mediator of retinoic acid and thyroid hormone receptor). Also useful are proteins that are subunits of Tup1-Ssn6 complexes. Examples of Tup1-Ssn6 complex subunits include Ume6, Tup1, Ssn6, Mig1, E2 or Crt1, and HDAC class I complexes (Rpd3, Hos1, Hos2). See e.g., Watson A. D. *Genes & Dev.*, 14:2737-2744, (2000). Other suitable subunits can include Sin4, Srb8, Srb10, Srb11, and Med3. In other embodiments, polypeptides having modifications relative to the above polypeptides are suitable second polypeptide segments.

Exemplary nucleotide and/or amino acid sequences of CAP/HDAC subunit genes and/or polypeptides are shown in Table 7.

Arrangement of Polypeptide Segments

Segments of a chimeric HAT polypeptide are linked to one another by covalent bonds, typically peptide bonds. The segments can be linked directly, without any intervening amino acids between two segments. Alternatively, one segment can be linked indirectly to an adjacent segment by amino acid residues that are situated between the two adjacent segments and are themselves covalently linked to the adjacent segments. In some embodiments, there are one, two, three, four, five, six, seven, eight, nine or ten intervening amino acid residues. In other embodiments, there are fifteen, twenty, thirty, forty or fifty intervening residues. In some embodiments, an intervening segment can be a hinge domain. Typically, if there is an intervening segment, at least one of the amino acids in the intervening segment is a glycine. At least one glycine is preferred in order to promote structural flexibility of the spacer, and permit free rotation of the first polypeptide segment relative to the second polypeptide segment. An illustrative embodiment of an intervening segment is one having fifteen glycine residues positioned between the first polypeptide segment and the second polypeptide segment and covalently linked to each by a peptide bond.

An intervening peptide segment can be situated between the segments of a chimeric polypeptide of the invention in order to facilitate interaction between the histone in a nucleosome and the HAT of the chimeric polypeptide. Structural modeling can be used to predict whether an intervening peptide segment is useful in a chimeric HAT polypeptide. Structural modeling can be performed using software such as Rasmol 2.6, available from the UC Berkeley website mc2.CChem.Berkeley.EDU/Rasmol/v2.6/. For example, the theoretical distance between the first polypeptide segment of a chimeric polypeptide and the surface of a nucleosome is modeled, based on the crystal structure of a nucleosome (histones H2A, $H_2B$, H3 and H4, and a 147 nucleotide DNA), the crystal structure of the DNA binding domain of a TATA binding protein and the crystal structure of a *Tetrahymena* histone acetyltransferase GCN5 homologue, including the coenzyme Acetyl-CoA and the 11-mer N-terminal tail of histone H3. The TATA binding protein is modeled as it is situated on the DNA of the nucleosome. The HAT is modeled while adjacent to the tail of histone H3. Next, the distance from the closest surface of HAT to the nucleosome surface is calculated. Based on this example, an intervening peptide segment of at least 28 Å in length facilitates interaction between the HAT and histone yet maintains nucleosome interaction and histone modification. Twenty eight Å is approximately the same length as a peptide containing 15 amino acids. Structural flexibility of the intervening peptide segment can be enhanced by using at least one glycine amino acid and/or at least one alanine amino acid.

The first polypeptide segment of a chimeric polypeptide can be the N-terminal segment of a chimeric polypeptide of the invention. In such embodiments, the C-terminus of the first polypeptide segment can be covalently linked to the N-terminus of the second polypeptide segment, or can be covalently linked to the N-terminus of an intervening peptide segment, which can be schematically indicated at $1^{st}$-$2^{nd}$ or $1^{st}$-i-$2^{nd}$, where "$1^{st}$" indicates the first polypeptide segment, "$2^{nd}$" indicates the second polypeptide segment and "i" indicates an optional intervening peptide segment.

In other embodiments, the first polypeptide segment can be the C-terminal segment of a chimeric polypeptide of the invention. In such embodiments, the C-terminus of the second polypeptide segment is covalently linked to the N-terminus of the first polypeptide segment, or can be covalently linked to the N-terminus of an intervening peptide segment, which can be schematically indicated as $2^{nd}$-$1^{st}$ or $2^{nd}$-i-$1^{st}$.

A chimeric polypeptide of the invention optionally can possess additional amino acid residues at the amino-terminus or the carboxy-terminus. For example, 6× His-tag or FLAG® residues can be linked to a polypeptide at the amino-terminus. See e.g., U.S. Pat. Nos. 4,851,341 and 5,001,912. As another example, a reporter polypeptide such as green fluorescent protein (GFP) can be fused to the carboxy-terminus of the chimeric polypeptide. See e.g., U.S. Pat. No. 5,491,084.

With respect to polypeptides, "isolated" refers to a polypeptide that constitutes a major component in a mixture of components, e.g., 30% or more, 40% or more, 50% or more, 60% or more, 70% or more, 80% or more, 90% or more, or 95% or more by weight. Isolated polypeptides typically are obtained by purification from an organism that makes the polypeptide, although chemical synthesis is also feasible. Methods of polypeptide purification include, for example, chromatography or immunoaffinity techniques.

The amino acid sequence of either or both polypeptide segments of a chimeric HAT polypeptide can be a non-naturally occurring amino acid sequence. For example, the amino acid sequence of one polypeptide segment can be a naturally occurring sequence found in a particular species, while the amino acid sequence of the other polypeptide segment is a non-naturally occurring consensus amino acid sequence based on the naturally occurring sequences of homologs from different species.

A polypeptide of the invention can be detected by sodium dodecyl sulphate (SDS)-polyacrylamide gel electrophoresis followed by Coomassie Blue-staining or Western blot analysis using monoclonal or polyclonal antibodies that have binding affinity for the polypeptide to be detected.

Nucleic Acids Encoding a Chimeric Polypeptide

The present invention also includes nucleic acids encoding the above-described chimeric polypeptides. As used herein, nucleic acid refers to RNA or DNA, including cDNA, synthetic DNA or genomic DNA. The nucleic acids can be single- or double-stranded, and if single-stranded, can be either the coding or non-coding strand. As used herein with respect to nucleic acids, "isolated" refers to (i) a naturally-occurring nucleic acid encoding part or all of a polypeptide of the invention, but free of sequences, i.e., coding sequences, that normally flank one or both sides of the nucleic acid encoding polypeptide in a genome; (ii) a nucleic acid incorporated into a vector or into the genomic DNA of an organism such that the resulting molecule is not identical to any naturally-occurring vector or genomic DNA; or (iii) a cDNA, a genomic nucleic acid fragment, a fragment produced by polymerase chain reaction (PCR) or a restriction fragment. Specifically excluded from this definition are nucleic acids present in mixtures of nucleic acid molecules or cells.

It should be appreciated that nucleic acids having a nucleotide sequence other than the specific nucleotide sequences disclosed herein can still encode a polypeptide having the exemplified amino acid sequence. The degeneracy of the genetic code is well known to those of ordinary skill in the art; i.e., for many amino acids, there is more than one nucleotide triplet that serves as the codon for the amino acid.

Nucleic Acid Constructs

Further provided are nucleic acid constructs comprising the above-described nucleic acid coding sequences. Such constructs can comprise a cloning vector. Cloning vectors suitable for use in the present invention are commercially available and are used routinely by those of ordinary skill in the art.

Nucleic acid constructs also can contain sequences encoding other polypeptides. Such polypeptides can, for example, facilitate the introduction or maintenance of the nucleic acid construct into a host organism. Other polypeptides also can affect the expression, activity, or biochemical or physiological effect of the encoded CBF polypeptide. Alternatively, other polypeptide coding sequences can be provided on separate nucleic acid constructs.

Nucleic acid constructs of the invention can comprise one or more regulatory elements operably linked to a nucleic acid coding sequence. Such regulatory elements can include promoter sequences, enhancer sequences, response elements or inducible elements that modulate expression of a nucleic acid sequence. As used herein, "operably linked" refers to positioning of a regulatory element in a construct relative to a nucleic acid coding sequence in such a way as to permit or facilitate expression of the encoded polypeptide. The choice of element(s) that can be included depends upon several factors, including, but not limited to, replication efficiency, selectability, inducibility, desired expression level, and cell or tissue specificity.

Suitable regulatory elements include promoters that initiate transcription only, or predominantly, in certain cell types. For example, promoters specific to vegetative tissues such as ground meristem, vascular bundle, cambium, phloem, cortex, shoot apical meristem, lateral shoot meristem, root apical meristem, lateral root meristem, leaf primordium, leaf mesophyll, or leaf epidermis can be suitable regulatory elements. In other embodiments, a promoter specific to a reproductive tissue (e.g., fruit, ovule, seed, pollen, pistils, female gametophyte, egg cell, central cell, nucellus, suspensor, synergid cell, flowers, embryonic tissue, embryo, zygote, endosperm, integument, seed coat or pollen) is used. A cell type or tissue-specific promoter can drive expression of operably linked sequences in tissues other than the target tissue. Thus, as used herein a cell type or tissue-specific promoter is one that drives expression preferentially in the target tissue, but can also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell*, 1:839-854 (1989); Green, et al., *EMBO J.*, 7:4035-4044 (1988); Meier, et al., *Plant Cell*, 3:309-316 (1991); and Zhang, et al., *Plant Physio.*, 110:1069-1079 (1996).

Exemplary reproductive tissue promoters include those derived from the following seed-genes: zygote and embryo LEC1 (see, Lotan (1998) *Cell* 93:1195-1205); suspensor G564 (see, Weterings. (2001) *Plant Cell* 13:2409-2425); maize MAC1 (see, Sheridan (1996) *Genetics*, 142:1009-1020); maize Cat3 (see, GenBank No. L05934; Abler (1993) *Plant Mol. Biol.*, 22:10131-1038); *Arabidopsis* viviparous-1 (see, Genbank No. U93215); *Arabidopsis* atmycl (see, Urao (1996) *Plant Mol. Biol.*, 32:571-57; Conceicao (1994) *Plant*, 5:493-505); and Brassica napus napin gene family, including napA (see, GenBank No. J02798; Josefsson (1987) JBL 26:12196-1301; Sjodahl (1995) *Planta*, 197:264-271). Other exemplary reproductive tissue-specific promoters include those derived from the pollen genes described in, for example: Guerrero (1990) *Mol. Gen. Genet.*, 224:161-168; Wakeley (1998) *Plant Mol. Biol.*, 37:187-192; Ficker (1998) *Mol. Gen. Genet.*, 257:132-142; Kulikauskas (1997) *Plant Mol. Biol.*, 34:809-814; and Treacy (1997) *Plant Mol. Biol.*, 34:603-611. Yet other suitable reproductive tissue promoters include those derived from the following embryo genes: Brassica napus 2s storage protein (see, Dasgupta (1993) *Gene*, 133:301-302); *Arabidopsis* 2s storage protein (see, GenBank No. AL161566); soybean β-conglycinin (see, GenBank No. S44893); Brassica napus oleosin 20 kD gene (see, GenBank No. M63985); soybean oleosin A (see, Genbank No. U09118); soybean oleosin B (see, GenBank No. U09119); soybean lectin1 (see, GenBank K00821); soybean Kunitz trypsin inhibitor 3 (see, GenBank No. AF233296); soybean glycinin1 (see, GenBank No. X15121); *Arabidopsis* oleosin (see, GenBank No. Z17657); maize oleosin 18 kD (see, GenBank No. J05212; Lee (1994) Plant Mol. Biol. 26:1981-1987); and the gene encoding low molecular weight sulfur rich protein from soybean (see, Choi (1995) *Mol. Gen. Genet.*, 246:266-268). Yet other exemplary reproductive tissue promoters include those derived from the following endosperm genes: *Arabidopsis* Fie (see, GenBank No. AF129516); *Arabidopsis* Mea; *Arabidopsis* Fis2 (see, GenBank No. AF096096); rice Glu1 (see, GenBank No. M28156); and rice 26 kDa globulin (see, GenBank No. D50643). Yet other exemplary reproductive tissue promoters include those derived from the following genes: ovule BEL1 (see, Reiser (1995) *Cell*, 83:735-742; Ray (1994) *Proc. Natl. Acad. Sci. USA*, 91:5761-5765; GenBank No. U39944); central cell FIE (see, GenBank No. AF129516); flower primordia *Arabidopsis* APETALA1 (a.k.a. AP1) (see, Gustafson-Brown (1994) *Cell*, 76:131-143; Mandrel (1992) *Nature*, 360:273-277); flower *Arabidopsis* AP2 (see, Jofuku (1994) *Plant Cell* 6:1211-1225); *Arabidopsis* flower ufo, expressed at the junction between sepal and petal primordia (see, Bossinger (1996) *Development*, 122:1093-1102); fruit-specific tomato E8; a tomato gene expressed during fruit ripening, senescence and abscission of leaves and flowers (see, Blume (1997) *Plant J.*, 12:731-746); pistil-specific potato SK2 (see, Ficker (1997) Plant Mol. Biol., 35:425-431); *Arabidopsis* DMC1 (see, GenBank No. U76670); and *Arabidopsis* DMT1 (see, Choi (2002) *Cell*, 109).

Suitable vegetative tissue promoters include those derived from the following genes: pea Blec4, active in epidermal tissue of vegetative and floral shoot apices of transgenic alfalfa; potato storage protein patatin gene (see, Kim (1994) *Plant Mol. Biol.*, 26:603-615; Martin (1997) *Plant J.*, 11:53-62); root Agrobacterium rhizogenes ORF13 (see, Hansen (1997) *Mol. Gen. Genet.*, 254:337-343); genes active during taro corm development (see, Bezerra (1995) *Plant Mol. Biol.*, 28:137-144); de Castro (1992) *Plant Cell*, 4:1549-1559); root meristem and immature central cylinder tobacco gene TobRB7 (see, Yamamoto (1991) *Plant Cell*, 3:371-382); ribulose biphosphate carboxylase genes RBCS1, RBCS2, and RBCS3A expressed in tomato leaves (see, Meier (1997) *FEBS Lett.*, 415:91-95); ribulose biphosphate carboxylase genes expressed in leaf blade and leaf sheath mesophyll cells (see, Matsuoka (1994) *Plant J.*, 6:311-319); leaf chlorophyll a/b binding protein (see e.g., Shiina (1997) *Plant Physiol.*, 115:477-483; Casal (1998) *Plant Physiol.*, 116:1533-1538); *Arabidopsis* Atmyb5, expressed in developing leaf trichomes, stipules, in epidermal cells on the margins of young rosette and cauline leaves, and in immature seeds between fertilization and the 16 cell stage of embryo development and persists beyond the heart stage (see, Li (1996) *FEBS Lett.*, 379:117-121); a maize leaf-specific gene described by Busk (1997) *Plant J.*, 11: 1285-1295; "SHOOTMERISTEMLESS" and "SCARECROW" genes active in developing shoot or root apical meristems (see e.g., Di Laurenzio (1996) *Cell*, 86:423-433; Long (1996) *Nature*, 379:66-69); 3-hydroxy-3-methylglutaryl coenzyme A reductase HMG2, expressed in meristematic tissue, and floral reductase HMG2, expressed in meristematic and floral (e.g., secretory zone of the stigma, mature pollen grains, gynoecium vascular tissue, and fertilized ovules) tissues (see, Enjuto (1995) *Plant Cell*, 7:517-527); meristem kn1-related genes from maize and other species (see, Granger (1996) *Plant Mol. Biol.*, 31:373-378; Kerstetter (1994) *Plant Cell*, 6:1877-1887; Hake (1995) *Philos. Trans. R. Soc. Lond. B. Biol. Sci.*, 350:45-51; Lincoln (1994) *Plant Cell*, 6:1859-1876); and constitutive Cauliflower mosaic virus 35S.

Cell type or tissue-specific promoters derived from viruses also can be suitable regulatory elements. Exemplary viral promoters include: the tobamovirus subgenomic promoter (Kumagai (1995) *Proc. Natl. Acad. Sci. USA*, 92:1679-1683; the phloem-specific tungro bacilliform virus (RTBV) promoter; the cassaya vein mosaic virus (CVMV)

promoter, expressed most strongly in vascular elements, leaf mesophyll cells, and root tips (Verdaguer (1996) *Plant. Mol. Biol.*, 31:1129-1139).

In some embodiments, a nucleic acid construct of the invention contains a promoter and a recognition site for a transcriptional activator, both of which are operably linked to the coding sequence for a chimeric polypeptide. In these embodiments, transgenic organisms or mixtures of cells that express the chimeric polypeptide contain a second nucleic acid construct that encodes a transcriptional activator. A transcriptional activator is a polypeptide that binds to a recognition site on DNA, resulting in an increase in the level of transcription from a promoter associated in cis with the recognition site.

The recognition site for the transcriptional activator polypeptide is positioned with respect to the promoter so that upon binding of the transcriptional activator to the recognition site, the level of transcription from the promoter is increased. The position of the recognition site relative to the promoter can be varied for different transcriptional activators, in order to achieve the desired increase in the level of transcription.

Many transcriptional activators have discrete DNA binding and transcription activation domains. The DNA binding domain(s) and transcription activation domain(s) of transcriptional activators can be synthetic or can be derived from different sources (e.g., two-component system or chimeric transcriptional activators). In some embodiments, a two-component system transcriptional activator has a DNA binding domain derived from the yeast gal4 gene and a transcription activation domain derived from the VP 16 gene of herpes simplex virus. In other embodiments, a two-component system transcriptional activator has a DNA binding domain derived from a yeast HAP1 gene and the transcription activation domain derived from VP 16. Populations of transgenic organisms or cells having a first nucleic acid construct that encodes a chimeric polypeptide and a second nucleic acid construct that encodes a transcriptional activator polypeptide can be produced by transformation, transfection, or genetic crossing. See e.g., WO 97/31064.

A nucleic acid encoding a novel polypeptide of the invention can be obtained by, for example, DNA synthesis or the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach, C. & Dveksler, G., Eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies are available by which site-specific nucleotide sequence modifications can be introduced into a template nucleic acid.

Nucleic acids of the present invention can be detected by methods such as ethidium bromide staining of agarose gels, Southern or Northern blot hybridization, PCR or in situ hybridizations. Hybridization typically involves Southern or Northern blotting (see, for example, sections 9.37-9.52 of Sambrook et al., 1989, *"Molecular Cloning, A Laboratory Manual"*, 2$^{nd}$ Edition, Cold Spring Harbor Press, Plainview; N.Y.). Probes should hybridize under high stringency conditions to a nucleic acid or the complement thereof. High stringency conditions can include the use of low ionic strength and high temperature washes, for example 0.015 M NaCl/0.0015 M sodium citrate (0.1×SSC), 0.1% sodium dodecyl sulfate (SDS) at 65° C. In addition, denaturing agents, such as formamide, can be employed during high stringency hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Eukaryotic Organisms

The term "host" or "host cell" includes not only prokaryotes, such as *E. coli*, but also eukaryotes, such as fungal, insect, plant and animal cells. Animal cells include, for example, COS cells and HeLa cells. Fungal cells include yeast cells, such as *Saccharomyces cereviseae* cells. A host cell can be transformed or transfected with a DNA molecule (e.g., a vector) using techniques known to those of ordinary skill in this art, such as calcium phosphate or lithium acetate precipitation, electroporation, lipofection and particle bombardment. Host cells containing a vector of the present invention can be used for such purposes as propagating the vector, producing a nucleic acid (e.g., DNA, RNA, antisense RNA) or expressing a polypeptide or fragments thereof.

Plants

Among the eukaryotic organisms featured in the invention are plants containing an exogenous nucleic acid that encodes a polypeptide of the invention, e.g., nucleic acids encoding a polypeptide having an amino acid sequence as shown in Table 9 or in Table 11.

Accordingly, a method according to the invention comprises introducing a nucleic acid construct as described herein into a plant. Techniques for introducing exogenous nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,204,253 and 6,013,863. If a cell or tissue culture is used as the recipient tissue for transformation, plants can be regenerated from transformed cultures by techniques known to those skilled in the art. Transgenic plants can be entered into a breeding program, e.g., to introduce a nucleic acid encoding a polypeptide into other lines, to transfer the nucleic acid to other species or for further selection of other desirable traits. Alternatively, transgenic plants can be propagated vegetatively for those species amenable to such techniques. Progeny includes descendants of a particular plant or plant line. Progeny of an instant plant include seeds formed on $F_1$, $F_2$, $F_3$, and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth or sorghum. Also suitable are vegetable crops or root crops such as potato, broccoli, peas, sweet corn, popcorn, tomato, beans (including kidney beans, lima beans, dry beans, green beans) and the like. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medi-* cago, *Nicotiana, Olea, Oryza, Panicum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* and *Zea.*

Chimeric polypeptides of the invention can be expressed in plants in a cell- or tissue-specific manner according to the regulatory elements chosen to include in a particular nucleic acid construct present in the plant. Suitable cells, tissues and organs in which to express a chimeric polypeptide of the invention include, without limitation, egg cell, central cell, synergid cell, zygote, ovule primordia, nucellus, integuments, endothelium, female gametophyte cells, embryo, axis, cotyledons, suspensor, endosperm, seed coat, ground meristem, vascular bundle, cambium, phloem, cortex, shoot or root apical meristems, lateral shoot or root meristems, floral meristem, leaf primordia, leaf mesophyll cells, and leaf epidermal cells, e.g., epidermal cells involved in forming the cuticular layer.

Fungi

Other eukaryotic organisms featured in the invention are fungi containing an exogenous nucleic acid that encodes a chimeric polypeptide of the invention, e.g., nucleic acids encoding a polypeptide having the amino acid sequence as shown in Table 9 or in Table 11.

Accordingly, a method according to the invention comprises introducing a nucleic acid construct as described herein into a fungus. Techniques for introducing exogenous nucleic acids into many fungi are known in the art, e.g., U.S. Pat. Nos. 5,252,726 and 5,070,020. Transformed fungi can be cultured by techniques known to those skilled in the art. Such fungi can be used to introduce a nucleic acid encoding a polypeptide into other fungal strains, to transfer the nucleic acid to other species or for further selection of other desirable traits.

A suitable group of fungi with which to practice the invention include fission yeast and budding yeast, such as *Saccharomyces cereviseae, S. pombe, S. carlsbergeris* and *Candida albicans.* Filamentous fungi such as *Aspergillus* spp. and *Penicillium* spp. also are useful.

Animals

Other eukaryotic organisms featured in the invention are animals (e.g., insects such mosquitoes and flies; fish; and non-human mammals such as rodents, bovines and porcines) that contain an exogenous nucleic acid that encodes a chimeric polypeptide of the invention, e.g., nucleic acids encoding a polypeptide having the amino acid sequence as shown in Table 9 or in Table 11. A variety of techniques known in the art can be used to generate such transgenic animals. Such techniques typically involve generating a plurality of animals whose genomes can be screened for the presence or absence of the transgene. For example, a transgene can be introduced into a non-human mammal by pronuclear microinjection (U.S. Pat. No. 4,873,191), retrovirus mediated gene transfer into germ lines (Van der Putten et al., *Proc. Natl. Acad. Sci. USA,* 82:6148, 1985), gene targeting into embryonic stem cells (Thompson et al., *Cell,* 56:313, 1989), electroporation of embryos (Lo, *Mol. Cell. Biol.,* 3:1803, 1983), and transformation of somatic cells in vitro followed by nuclear transplantation (Wilmut et al., *Nature,* 385(6619):810-813, 1997; and Wakayama et al., *Nature,* 394:369-374, 1998). When using mice to make a transgenic animal, suitable genetic backgrounds for use in making founder lines include, without limitation, C57B6, SJL/J, FVB/N, 129SV, BALB/C, C3H, and hybrids thereof.

Methods of Gene Profiling

In another aspect, the invention provides a method in which gene function can be determined from changes in an organism's gene expression profile. The method involves expressing a chimeric polypeptide in a specific cell type, tissue or organ in an organism or population of organisms. The organism can be, for example, an animal, plant, or fungus. The term "specific cell type" refers to cells that have one or more characteristics that distinguish them from the other cells in an organism, or from other cells in a mixture of cells. Distinguishing features can include, for example, physical location, cell division rate, developmental stage, differentiation status, macromolecular composition, gene expression profile, protein expression profile, particular cell type, or presence or absence of a particular polypeptide. Specific cell types can be found in an organ, tissue, or tissue or cell culture, e.g., egg cells from embryo sacs, scutellar cells of a mature kernel, cells containing seed storage proteins from cotyledons and rapidly dividing fibroblasts from skin. Specific cell types also can be found in more than one organ, tissue, or tissue or cell culture, e.g., meristematic cells from plant shoot and root apices, and mucosal cells from the large intestine and the nasal cavity.

The method typically involves introducing an exogenous nucleic acid encoding the chimeric polypeptide into an organism. In some embodiments, the exogenous nucleic acid contains a regulatory element that directs expression of the chimeric polypeptide in specific cell types. In other embodiments, the exogenous nucleic acid is situated in the genome of the target organism such that expression of the chimeric polypeptide is governed by native transcriptional regulatory elements (e.g., a native cell type-specific promoter).

In yet other embodiments, the nucleic acid construct encoding a chimeric polypeptide contains a recognition site for a transcriptional activator. In these embodiments, transgenic organisms or mixtures of cells that express the chimeric polypeptide contain a second nucleic acid construct that encodes the transcriptional activator, and one or more regulatory elements that facilitate expression of the transcription activator in a specific cell type. Thus, in these embodiments, the exogenous transcription activator is expressed in specific cells, and in turn activates transcription of the chimeric polypeptide in those cells. Populations of transgenic organisms or cells having a first nucleic acid construct that encodes a chimeric polypeptide and a second nucleic acid construct that encodes a transcriptional activator can be produced by transformation, transfection, or genetic crossing.

Cell type-specific expression of a chimeric polypeptide can alter an organism's gene expression profile (i.e., the cell types in which particular sets of genes are transcribed, and the level at which such genes are transcribed) relative to organisms that do not express the chimeric polypeptide. Alterations in gene expression profile can be manifested in changes in the macromolecular (e.g., RNA, protein, chemical) composition of organisms that express a chimeric polypeptide in a cell-specific manner. The skilled artisan can measure the RNA or protein composition of specific cells using routine techniques such as, for example, thin layer or gas-liquid chromatography, gel electrophoresis of protein extracted from appropriate cells, and gel electrophoresis of RNA extracted from appropriate cells. The skilled artisan can measure the expression of particular genes or proteins using the above-mentioned methods alone or in combination with, for example, protein immunochemistry or nucleic acid hybridization assays using electrophoretically or chromatographically separated macromolecules, microarray analysis, or specific RT-PCR. The above-described techniques can provide quantitative, semi-quantitative or qualitative detection of gene expression. Alterations in gene expression profile can be detected by comparing the gene expression profiles of, for example, a transgenic organism that expresses the chimeric polypeptide in specific cells and an organism that lacks the nucleic acid construct or does not express the chimeric polypeptide.

Once the transcriptional and/or translational activity of a set of genes has been determined in a specific cell type and/or at a desired time, the function of the set of genes can be assigned to particular developmental, physiological and/or biochemical pathways. In addition, a microarray containing the set of genes, or a subset thereof, can be made. See e.g., U.S. Pat. Nos. 5,424,186 and 6,156,501. The microarray can contain a plurality of oligonucleotides, each oligonucleotide representing a portion of the sequence of one gene from the set of genes. Each of the oligonucleotides is coupled to a solid substrate at a known location. The substrate can be silica, polymeric materials, glass, beads, slides or chips. Such microarrays can be used, for example, to determine the level of transcription of the set of genes in other cell types and thereby identify genes whose transcription is repressed solely in the specific cell type. Such genes are suitable targets for further manipulation. For example, genes that are inactivated solely during fruit maturation can be targeted for a modification that results in continued expression of such genes for an additional period of time, in order to delay fruit ripening and/or increase fruit size.

Methods for Modulating Gene Expression

In another aspect, the invention provides methods for modulating gene expression in an organism. Modulating gene expression involves expressing a chimeric polypeptide in specific cells in an organism or population of organisms. The organism can be, for example, yeast or a plant.

An exogenous nucleic acid encoding a chimeric polypeptide is introduced into an organism. In some embodiments, the exogenous nucleic acid contains a regulatory element that directs expression of the chimeric polypeptide in specific cells or tissues. In other embodiments, the exogenous nucleic acid is situated in genome of the target organism such that expression of the chimeric polypeptide is governed by native transcriptional regulatory elements (e.g., a native cell type or tissue-specific promoter).

In yet other embodiments, the nucleic acid construct that encodes a chimeric polypeptide contains a recognition site for a transcriptional activator. In these embodiments, transgenic organisms or mixtures of cells that express the chimeric polypeptide contain a second nucleic acid construct that encodes a transcriptional activator. The second nucleic acid construct contains a regulatory element that directs expression of the transcription activator in specific cells. Thus, in these embodiments, the exogenous transcription activator is expressed in specific cells or tissues, and in turn activates transcription of the chimeric polypeptide in those cells. Populations of transgenic organisms or cells having a nucleic acid construct that encodes a chimeric polypeptide and a nucleic acid construct that encodes a transcriptional activator polypeptide can be produced by transformation, transfection, or genetic crossing.

By expressing a chimeric polypeptide in specific cells, it is possible to modulate gene expression in an organism (e.g., by derepressing genes that normally are transcriptionally inactive). An organism or cell exhibiting modulated gene expression can have compositional (e.g., protein, nucleic acid, lipid, saccharide), developmental and phenotypic alterations relative to organisms or cells that do not express the chimeric polypeptide. For example, modulated gene expression in plants can alter seed development, seed yield, seed composition, endosperm development, embryo development, cotyledon development, seed size, flowering time, plant size, leaf size, leaf shape, plant fertility, apical dominance, floral organ identity, root development, or organ composition. In plants, cell type-specific expression of chimeric polypeptides also can cause fertilization independent endosperm development and fertilization independent seed development.

In some embodiments, seed development can be altered by expressing a chimeric polypeptide in the developing ovule or seed of a plant. In such embodiments, the chimeric polypeptide can modulate endosperm and/or embryo development; developing seed in such plants can exhibit altered endosperm and/or altered embryo development; and plants can exhibit altered seed yield (by number and/or mass). The effects of expressing a chimeric polypeptide on seed development can be enhanced when DNA methylation is reduced. DNA methylation can be reduced, e.g., by mutation of or antisense nucleic acid interference with a gene encoding a DNA methyltransferase. Exemplary plant DNA methyltransferase genes include Met1, Cmt3, Zmet2, Drm1, Drm2 (Vielle-Calzada et al. (1999) *Genes & Dev.* 13:2971-2982; Richards et al. (2000) U.S. Pat. No. 6,153,741; Dellaporta and Chen (2000) U.S. Pat. No. 6,011,200; Vinkenoog et al. (2000) *The Plant Cell* 12:2271-2282; Luo et al. (2000) *Proc. Natl. Acad. Sci. USA* 97:10637-10642; Jackson et al. (2002) *Nature* 416:556-560). DNA methylation also can be reduced by mutation of or antisense nucleic acid interference with certain genes that encode chromatin associated proteins that have a role in DNA methylation. Such genes include Ddm1 (see Jeddeloh et al. (1999) *Nature Genetics* 22:94-97) and Kyp (see Jackson et al. (2002) *Nature* 416:556-560). In these embodiments, plants can have altered seed yield by mass. Mutations of or antisense nucleic acid interference with other genes, such as Mom (see Amedeo et al. (2000) *Nature* 405:203-206), that have a post-DNA methylation role in DNA methylation state also can enhance the effects of expressing a chimeric polypeptide on seed development.

In some embodiments, the exogenous nucleic acid contains a regulatory element that directs expression of the chimeric polypeptide to specific cells or tissues.

In yet other embodiments, the nucleic acid construct that encodes a chimeric polypeptide contains a recognition site for a transcriptional activator. In these embodiments, transgenic organisms or mixtures of cells that express the chimeric polypeptide contain a second nucleic acid construct that encodes a transcriptional activator. The second nucleic acid construct contains a regulatory element that directs expression of the transcription activator in specific cells. Thus, in these embodiments, the exogenous transcription activator is expressed in specific cells or tissues, and in turn activates transcription of the chimeric polypeptide in those cells. Populations of transgenic organisms or cells having a nucleic acid construct that encodes a chimeric polypeptide and a nucleic acid construct that encodes a transcriptional activator polypeptide can be produced by transformation, transfection, or genetic crossing.

Methods of Making Sterile Plants

In another aspect, the invention provides methods for making sterile plants by introducing an exogenous nucleic acid encoding a chimeric polypeptide. In some embodiments, the exogenous nucleic acid contains a regulatory element that directs expression of the chimeric polypeptide in reproductive cells. In other embodiments, the exogenous nucleic acid is situated in genome of the target organism such that expression of the chimeric polypeptide is governed by a native transcriptional regulatory element that facilitates transcription in reproductive cells.

In yet other embodiments, the nucleic acid construct that encodes a chimeric polypeptide contains a recognition site for a transcriptional activator. In these embodiments, transgenic plants that express the chimeric polypeptide contain a second nucleic acid construct that encodes a transcriptional activator and one or more regulatory elements that facilitate expression of the transcription activator in plant reproductive cells. Thus, in these embodiments, the transcription activator is expressed in plant reproductive cells, which in turn activates transcription of the chimeric polypeptide in reproductive cells. Transformation and/or genetic crosses, for example, can produce plants that contain a nucleic acid construct that encodes a chimeric polypeptide and a nucleic acid construct that encodes a transcriptional activator polypeptide. Expressing a chimeric polypeptide in plant reproductive cells can affect the reproductive and/or developmental processes and prevent the production of viable embryos from female reproductive tissues.

The invention is further described in the following examples, which do not limit the scope of the invention described in the claims.

EXAMPLES

Example 1

Polypeptides having Histone Acetyltransferase Activity

Polypeptides are tested for histone acetyltransferase activity using assays previously described (see Brownell, J. and Allis, C. *Proc. Natl. Acad. Sci. USA*, 92:6364-6368 (1995); Brownell, J. E. et al. *Cell*, 84:843-851 (1996)). Coding sequences of candidate polypeptides are cloned into an appropriate expression vector, the expression vector is introduced into a bacterial host strain, expression of the gene is induced and protein extract is prepared. The extracts are incubated with calf thymus histones and [$^3$H]-acetyl-Coenzyme A. Radioactivity transferred to the histone substrate in an extract-dependent manner is quantified by liquid scintillation counting. Candidate polypeptides that transfer radioactivity to the histone substrate compared to positive controls (extracts from hosts expressing known HAT polypeptides) and negative controls (extract alone, histones without extract and comparable vector-only) have HAT activity. Alternatively, plant HAT activity is tested by determining whether expression of the corresponding cDNA is sufficient to rescue a yeast HAT mutant.

Example 2

Polypeptides having Histone Deacetylase Activity

Polypeptides are tested for histone deacetylase activity using assays previously described by van der Vlag, J. and Otte A. P. in *Nature Genetics*, 25:474-478 (1999). Coding sequences of candidate polypeptides are cloned into an appropriate expression vector, the expression vector is introduced into a bacterial host strain, expression of the gene is induced and protein extract is prepared. The extracts are incubated with [$^3$H]-acetylated histones or histone segments for 3-6 hours at 37° C. under shaking conditions in a buffer containing 20 mM Tris.-HCl, pH 7.4, ad 50 mM NaCl. The reaction is stopped by adding 7.7 mM HCl/1.2M acetic acid, and extracted with ethyl acetate. After centrifugation, the ethyl acetate fraction is counted in a liquid scintillation counter. Candidate polypeptides that remove radioactivity from the histone substrate compared to positive controls (extracts from hosts expressing known HDAC polypeptides) and negative controls (extract alone, histones without extract, vector-only, and parallel trichostatin A-containing reactions) have HDAC activity. Alternatively, HDAC activity is tested by determining whether expressing a candidate HDAC polypeptide (e.g., using an nucleic acid construct containing the corresponding cDNA clone) in a yeast HDAC mutant can rescue the mutant phenotype.

Example 3

Chimeric HAT Nucleic Acid Construct pFIE-15G-ESA1

The chimeric HAT gene construct was constructed using standard molecular biology techniques. The construct contains the coding sequence for the *Arabidopsis* FIE polypeptide and the coding sequence for a truncated *Arabidopsis* HAT polypeptide linked in frame by a DNA fragment encoding fifteen glycine residues. The FIE coding sequence was obtained from plasmid pFIE3.6. The *Arabidopsis* FIE polypeptide is a homolog of the Drosophila polycomb protein extra sex combs (esc) (see Ohad et al., *Plant Cell*, 11:407-415 (1999)). The *Arabidopsis* HAT polypeptide AtESA1 is a homolog of the yeast ESA1 polypeptide. pFIE-15G-ESA1 contains 5 binding sites for the DNA binding domain of the Gal4 transcription factor ($UAS_{GAL4}$) located 5' to a CaMV35S minimal promoter. The CaMV35S minimal promoter is located 5' to the FIE coding sequence. A DNA fragment encoding fifteen glycine residues is present, in frame, at the 3' end of the UAS-FIE DNA sequence, followed, in frame, by a DNA fragment encoding an *Arabidopsis* homologue of ESA1.

The coding sequence for a truncated AtESA1 was fused to the 3'-end of the FIE coding sequence by fusion PCR (Levin HL, *Mol. Cell Biol.*, 15:3310-3317 (1995)). Two intermediate PCR products were generated for this purpose. The first intermediate product contained a coding sequence for FIE having a 15-glycine spacer fused to its carboxy-terminus. This product was generated using two synthetic oligonucleotides and a pFIE3.6 DNA template. Similarly, the second intermediate PCR product contained a coding sequence for AtESA1 having a 15 glycine spacer fused to its amino-terminus. This product was generated using two synthetic oligonucleotides and a pAtESA1 cDNA template. The two intermediate products were then fused to each other in a final round of PCR using a set of synthetic primers that introduced a BglII site at the 5' end of the fusion and a XhoI site at the 3' end of the fusion. The resultant PCR product contained a chimeric sequence encoding a fusion peptide in which the amino-terminus of the FIE coding sequence is linked by a 15-glycine spacer to the carboxy-terminus the truncated AtESA1 coding sequence. This final PCR product was digested with BglII and XhoI and cloned into the Ti-plasmid vector pCRS304-5UAS which was previously digested with BamHI and XhoI. The resulting plasmid was named pCRS304-5UAS-FIE-15G-ESA1. The transgene was designated FIE-15G-ESA1. The amino acid sequence of the chimeric polypeptide encoded by the transgene is shown in Table 9 and the nucleotide sequence of the transgene is shown in Table 10.

Thus, pCRS304-5UAS-FIE-15G-ESA1 encodes a chimeric polypeptide having an *Arabidopsis thaliana* FIE polypeptide and a truncated *Arabidopsis thaliana* HAT polypeptide, linked by an intervening peptide spacer of 15 glycine residues. The plasmid contains 5 copies of the Gal4 upstream activator sequence (UAS$_{GAL4}$) located 5' and operably linked to the CaMV35S minimal promoter. This in turn is located 5' and operably linked to the FIE-15G-ESA1 coding sequence. The binding of a transcription factor that possesses a Gal4 DNA binding domain to the Gal4 UAS is necessary for transcriptional activation.

Example 4

Chimeric HAT Nucleic Acid Construct pMEA-15G-ESA1

The chimeric HAT gene construct pMEA-15G-ESA1 was constructed using standard molecular biology techniques. The construct contains the coding sequence for the *Arabidopsis* MEA polypeptide and the coding sequence for an *Arabidopsis* HAT polypeptide joined in frame by a DNA fragment encoding fifteen glycine residues. The MEA coding sequence was obtained from plasmid pCB1(MEA-cDNA) (Kiyosue, T., et al. (1999) *Proc. Natl. Acad. Sci. USA* 96:4186-4191). The *Arabidopsis* MEA polypeptide is a homolog of the Drosophila polycomb protein Enhancer of zeste (E(z)) (see Grossniklaus, U., et al. (1998) *Science* 280: 446-450.; Kiyosue, T., et al. (1999) *Proc. Natl. Acad. Sci. USA* 96:4186-4191). The *Arabidopsis* HAT polypeptide AtESA1 is a homolog of the yeast ESA1 polypeptide. The pMEA-15G-ESA1 plasmid contains 5 binding sites for the DNA binding domain of the Gal4 transcription factor (UAS$_{GAL4}$) located 5' to a CaMV35S minimal promoter. The CaMV35S minimal promoter is located 5' to the MEA coding sequence. A DNA fragment encoding fifteen glycine residues is present, in frame, at the 3' end of the UAS—MEA DNA sequence, followed, in frame, by a DNA fragment encoding an *Arabidopsis* homologue of ESA1.

The AtESA1 coding sequence was fused to the 3'-end of the MEA coding sequence by standard cloning techniques. Two intermediate PCR products were generated for this purpose. The first intermediate product contained the MEA coding sequence, flanked on either side by a BamHI restriction site. The BamHI sites were generated by incorporation into the PCR primer sequences. The first intermediate PCR product was digested with BamHI restriction enzyme and was cloned into the T-DNA expression vector pCRS304-5USAL at its unique BamHI site. The resultant plasmid was named pCRS304-5USAL-MEA-no 3'UTR.

The second intermediate PCR product contained a coding sequence for AtESA1 having a 15-glycine spacer fused to its amino terminus. The second intermediate PCR product was generated using two synthetic oligonucleotides and the pAtESA1-cDNA template. The second PCR product was flanked by a unique SmaI site at its 5' end and by a unique XhoI site at its 3'end. These cloning sites were generated by incorporation into the PCR primer sequences. The second PCR product was digested with SmaI and XhoI, and was cloned into the plasmid pCRS304-5USAL-MEA-no 3'UTR between the unique restriction sites SmaI and XhoI. The resultant plasmid was named pCRS304-5USAL-MEA-ESA1. The transgene was designated MEA-15G-ESA1. The amino acid sequence of the chimeric polypeptide encoded by the transgene is shown in Table 11 and the nucleotide sequence of the transgene is shown in Table 12.

Thus, pCRS304-5UAS-MEA-15G-ESA1 encodes a chimeric polypeptide having an *Arabidopsis thaliana* MEA polypeptide and an *Arabidopsis thaliana* HAT polypeptide, joined by an intervening peptide spacer of 15 glycine residues. The plasmid contains 5 copies of the Gal4 upstream activator sequence (UAS$_{GAL4}$) located 5' and operably linked to the CaMV35S minimal promoter. This in turn is located 5' and operably linked to the MEA-15G-ESA1 coding sequence. The binding of a transcription factor that possesses a Gal4 DNA binding domain to the Gal4 UAS is necessary for transcriptional activation.

Example 5

Transgenic Plants

The pCRS304-5UAS-FIE-15G-ESA1 plasmid and the pCRS304-5UAS-MEA-15G-ESA1 were independently introduced into *Arabidopsis* WS by *Agrobacterium tumefaciens* mediated transformation using the floral infiltration technique essentially as described in Bechtold, N. et al., *C. R. Acad. Sci. Paris,* 316:1194-1199 (1993). Several transformed plants, designated FE #1, FE #2, and ME #1, were selected for further study. The FIE-15G-ESA1 gene and the MEA-15G-ESA1 gene were then transcriptionally activated in specific target cells and tissues by crossing with two-component enhancer trap lines expressing a chimeric Gal4-VP 16 activator protein (Haseloff et al.). In each activator line there is also a UAS$_{GAL4}$-GFP (green fluorescent protein) reporter gene.

Example 6

Two-component Activation Lines

The two-component system for activating target gene expression was first utilized in Drosophila and subsequently adopted for use in plants (see Bennett et al. (1998) U.S. Pat. No. 5,801,027; Liu et al. (1999) U.S. Pat. No. 5,968,793); Bennett et al. (2000) U.S. Pat. No. 6,127,606; Haseloff and Hodge (2001) U.S. Pat. No. 6,255,558). The two-component system typically consists of two independent transcription units: an activator gene and a target gene. The activator gene encodes a transcriptional activator, a DNA binding protein gene such as Gal4-VP16, operably linked to a plant or animal promoter. The target gene has a protein coding sequence, such as a cDNA, operably linked to a promoter that has multiple copies of an upstream activator sequence element (UAS$_{GAL4}$) to which the transcriptional activator protein can bind. A target gene can be activated genetically by crossing a target gene-containing plant with an activator gene-containing plant (i.e., from an "activator line"). Alternatively, a target gene in a cell, tissue, or whole organism can be activated by transforming with an activation gene containing vector.

An extensive collection of *Arabidopsis* two-component activation lines has been produced and described by Dr. Jim Haseloff et al. (see plantsci.cam.ac.uk/Haseloff/IndexCatalogue.html), and individual lines are available from the *Arabidopsis* Biological Resource Center (see *Arabidopsis*.org/abrc/haseloff.htm). The activator lines were produced using a T-DNA based enhancer trap strategy. In this system the Gal4-VP 16 gene containing a CaMV35S minimal promoter can be transcriptionally activated when T-DNA is inserted proximal to an endogenous enhancer element. Enhancer activity is revealed by the trans-activation of a UAS$_{GAL4}$-GFP reporter gene. Each activation line in the Haseloff collection contains one or more random T-DNA insertions in the *Arabidopsis* genome resulting in cell, tissue, or organ specific expression of a UAS$_{GAL4}$-GFP reporter gene. The amino acid sequence of the GAL4$_{UAS}$-VP 16 activator protein is shown in Table 8.

Six publicly available *Arabidopsis* two-component activation lines are described in Table 3 including J2592, J0661, Q2500, M0164, J2301 and J2921.

ductive organs. GFP images are publicly available at plantsci.cam.ac.uk./Haseloff/GAL4 and were independently confirmed. For example, in line J2592 GFP expression was detectable in young seedlings in the shoot and root epidermis, root cortex and root cap but not in the root apical meristem. GFP was also observed in seedling hypocotyl, petiole epidermis, expanded cotyledon and leaf vasculature. Low intensity GFP was detectable in the stem epidermis as

TABLE 3

Activation line GFP expression pattern

| Haseloff activation line reference number and ABRC seed stock number | Ovule and seed development | Root | Other | GFP Intensity |
|---|---|---|---|---|
| J2592 (CS9180) | Prefertilization ovule: ovule, funiculus and placenta. Developing seed: developing embryo and mature embryo. | Root cap, root epidermal cells. | Seedling: shoot and root epidermis, root cortex and root cap; hypocotyl, petiole epidermis, expanded cotyledon and leaf vasculature; stem epidermis and rosette leaf vasculature. Flower: sepal, petal and ovary vasculature; epidermis of mature sepal, petal, filament and ovary; stigma. | Medium |
| M0164 (CS9307) | Mature embryo. | Root: weak patchy expression in vasculature of primary root. | Seedling: strong in shoot apex, rosette leaf and petiole vasculature. Weak in cotyledon vasculature. Silique: older siliques only. | High |
| Q2500 (CS9135) | Ovule: prefertilization ovule. Seed: chalazal end of developing seed, seed coat and young embryo. | Root: vasculature. | Seedling: vasculature of hypocotyl, expanded cotyledons and first leaves. Flower: petal vasculature, placenta. | High |
| J0661 (CS9141) | Developing seed: funiculus, embryo. | Root: root vasculature. | Seedling: vasculature including root, hypocotyl, expanded cotyledons, rosette leaf vasculature, petiole. Cauline leaf vasculature. Flower: floral organ vasculature including pedicel, sepal, petal, filament and pistil. | Medium |
| J2921 (CS9194) | | Root: weak patchy expression in root; weak in root hair; strong in root vasculature and root tip; strong in junctions where lateral roots form. | Flower: broad expression in epidermis of immature buds; GFP decreases and becomes restricted to the ovary as the flower matures; weak expression in sepal and petal vasculature. | Medium |
| J2301 (CS9173) | Seed: seedcoat; GFP increases as silique matures; GFP detectable at suspensor end of embryo. | Root: very strong in root tip; weak in root cortex; root epidermis. | Seedling: weak throughout seedling vasculature; strong in leaf trichomes; also detected in atrichoblasts. Flower: base of sepal and petal, ovary epidermis, style. | Medium |

Each activation line displays a characteristic pattern of GFP accumulation in seedlings, vegetative organs and reprowell as in rosette leaf vasculature. GFP was observed in J2592 flowers including the vasculature of the sepal, petal and ovary and in the epidermis of the mature sepal, petal, filament, ovary and in stigmatic papillae. A low level of GFP was detected in the pedicel. GFP was observed in pre-fertilization ovules and in the funiculus and placenta. In fertilized seed GFP was detectable in developing seeds and in mature embryos. GFP expression patterns were observed to vary in some progeny of J2592.

In line M0164 seedlings, GFP expression was observed in the vasculature of the primary root. No expression was detectable in the root cap. Relatively intense GFP expression was observed in the shoot apex and in leaf and petiole vasculature. Low intensity GFP expression was observed in the cotyledon vasculature. In developing seed GFP was detectable in embryos. GFP expression was not detectable in the seed coat or endosperm.

Example 7

FIE-15G-ESA1 Activated Plants

The FIE-15G-ESA1 transgene was transcriptionally activated by crossing FE #1 and FE #2 plants with the GAL4-VP 16 two-component activation lines described in Table 3. Reciprocal crosses were carried out using FE #1 and FE #2 plants with each 2-component activation line. The seed produced in such a cross are referred to as $F_1$ seed. Thus, a first generation seed or plant produced by crossing FE #1 as the mother with J2592 as the pollen donor is referred to as $F_1$ (FE #1×J2592). A second generation seed or plant produced by self pollination of $F_1$ (FE #1×J2592) is referred to as $F_2$ (FE #1×J2592). $F_1$ seed produced by crossing FE #1 and FE #2 with the activation lines described above were collected from mature siliques or seed pods and dried using standard Arabidopsis procedures. These siliques typically contained mature seed, abnormal seed and aborted ovules.

To analyze the effect of FIE-15G-ESA1 expression on Arabidopsis development $F_1$ seed and seed from control plants were germinated on agar plates containing 1× Murashige and Skoog (MS) salts and 1 percent sucrose using standard Arabidopsis procedures. Germinated seedlings were scored 8 days after plating for germination efficiency, the presence or absence of the activator gene (inferred from GFP reporter gene activity) and seedling phenotypes. After phenotyping, $F_1$ seedlings were transferred to soil at the four rosette leaf stage and then grown under standard Arabidopsis greenhouse conditions. Flowering plants were tested by PCR for the presence of the FIE-15G-ESA1 target gene and scored again for GFP expression.

When line J2592 was used as the activation line, 86 percent of the $F_1$ seeds germinated normally. $F_1$ seedlings and plants exhibited both vegetative and reproductive effects of FIE-15G-ESA1 activity. For example, cotyledons were observed to be incomplete, cupped, or missing in 30 percent of all seedlings analyzed. In some instances, extra cotyledons were observed. Hypocotyl development was perturbed in twelve percent of all $F_1$ seedlings analyzed. Finally, twenty-four percent of $F_1$ seedlings displayed stunted or missing petioles. Developmental abnormalities resulted in the loss of some seedlings from the study. These phenotypes were not observed in seedlings produced by selfing J2592, FE #1, or FE #2. Nor were these phenotypes observed in seedlings produced by crossing these parents with a wild type plant. The results indicate that activation of FIE-15G-ESA1 by J2592 is responsible for these diverse traits.

When activation line M0164 was used to activate FIE-15G-ESA1, ninety-seven percent of the $F_1$ (M0164×FE #1) seed germinated successfully. Forty percent of $F_1$ seedlings analyzed showed vegetative defects including cotyledons that were incomplete, cupped, or missing. In some instances, extra cotyledons were observed. Thus, the $F_1$ seedling phenotypes induced using FIE-15G-ESA1 were not restricted to the J2592 activation line.

Reproductive phenotypes for $F_1$ plants containing activator and FIE-15G-ESA1 target genes were analyzed as described in Ohad, N., et al. (1999) The Plant Cell 11:407-415; and in Fischer, R. L., et al., (2001) U.S. Pat. No. 6,229,064. In brief, developing siliques were sampled along the primary inflorescence proximal to distal relative to the rosette leaves. Within each silique, the seed were classified according to the color and the status of endosperm and embryo development. Since $F_1$ seed are the product of genetic crossing, each silique that is produced by an $F_1$ plant should contain a population of $F_2$ seed that segregate for the activator and target genes and any resulting phenotype. Thus, each silique contains a population of wild type seed that provide a developmental reference for staging seed development and phenotyping. Seed phenotypes were recorded at two stages of seed development: (i) when the majority of seed in a silique were at the mature seed stage of embryo development, and (ii) at the torpedo to walking stick stage of embryo development.

Effect of FIE-15G-ESA1 gene activity on seed development: $F_2$ seeds were produced by $F_1$ plants through self-pollination. $F_2$ (FE #1×J2592) and $F_2$ (FE #2×J2592) seed development was characterized using a Zeiss dissecting microscope and a Zeiss Axioskope microscope as described by Ohad, N., et al., (1999) The Plant Cell 11:407-415 using standard Arabidopsis procedures.

Activation of FIE-15G-ESA1 by J2592 altered embryo and seed development as shown in Table 4. Self-pollinated $F_1$ (FE #1–×J2592) plants produced two classes of seed, (i) those exhibiting normal embryo and seed development, and (ii) those exhibiting abnormal seed and embryo development. Abnormal seed were found to contain an embryo whose development was arrested at the transition between heart and torpedo stages of development. By contrast, endosperm production was not arrested in abnormal seed but was greater than or equal to that observed in normal seed. Thus, FIE-15G-ESA1 was observed to alter the balance between endosperm and embryo development within the seed. Most abnormal seed abort and degenerate into shrunken seed. The percent abnormal to normal seed ranged from 25-62 percent (see Table 4). Similar results also were observed in $F_1$ (FE #2×J2592) plants. Similar results were observed when the reciprocal cross (i.e., J2592×FE #1) was performed. FIE-15G-ESA1 also was observed to alter seed development when J0661 was crossed with FE #1. By contrast, no abnormal seed were detected in $F_1$ plants produced by crossing Q2500, J2301 or J2921 with FE #1. In fact, more than 98 percent of seed from self-pollinated FE #1, FE #2 and J2592 parental lines had no visually observable abnormalities. Thus, the effect of FIE-15G-ESA1 activity on seed development appears to be promoter dependent.

TABLE 4

| | Normal seeds | Shrunken aborted seeds |
|---|---|---|
| Segregation of Seed phenotypes in developing siliques | | |
| F1(FE #1 X J2592) Plant #29 | | |
| Total | 225 | 683 |
| Percent | 25.6 | 74.4 |
| F1(FE #1 X J2592) Plant #31 | | |
| Total | 264 | 760 |
| | 25.8 | 74.2 |
| F1(FE #1 X J2592) Plant #35 | | |
| Total | 264 | 760 |
| Percent | 25.8 | 74.2 |

TABLE 4-continued

|  | Normal seeds | Shrunken aborted seeds |
|---|---|---|
| Segregation of Seed phenotypes in mature siliques | | |
| F1(FE #1 X J2592) Plant #35 | | |
| Total | 361 | 136 |
| Percent | | 37.7 |
| STD* | | 3.8 |
| F1(FE #1 X J2592) Plant #29 | | |
| Total | 355 | 115 |
| Percent | | 32.40 |
| STD | | 3.40 |
| F1(FE #1 X J2592) Plant #31 | | |
| Total | 364 | 111 |
| Percent | | 30.5 |
| STD | | 2.1 |
| F1(FE #1 X J2592) Plant #26 | | |
| Total | 379 | 151 |
| Percent | | 39.8 |
| STD | | 4.1 |
| F1(FE #1 X J2592) Plant #37 | | |
| Total | 369 | 125 |
| Percent | | 33.9 |
| STD | | 2.7 |
| F1(FE #1 X J2592) Plant #32 | | |
| Total | 308 | 192 |
| Percent | | 62.3 |
| STD | | 5.2 |

*STD = standard deviation

Example 8

MEA-15G-ESA1 Activated Plants

The MEA-15G-ESA1 transgene was transcriptionally activated by crossing ME #1 with J2592, J0661 and Q2500 (see Table 5). Reciprocal crosses between ME #1 and each activation line also were made. $F_1$ seeds were collected at maturity and stored under standard conditions. To analyze the effect of MEA-15G-ESA1 expression on *Arabidopsis* development $F_1$ seed and seed from control plants were germinated on agar plates containing 1× MS salts and 1 percent sucrose. Subsequently, plants were phenotyped as described in Example 7. Mature plants were tested for the presence of MEA-15G-ESA1 by PCR.

When J2592 or Q2500 were crossed with ME #1 (pCRS304-5UAS-MEA-15G-ESA1 transformed plant #1) the $F_1$ seedlings exhibited vegetative phenotypes similar to those caused by FIE-15G-ESA1 in $F_1$ (FE #1×J2592) and (FE #1×M0164). For example, the cotyledons of $F_1$ seedlings were observed to be incomplete, cupped, or missing. Hypocotyl development also was perturbed. These phenotypes were not observed in seedlings produced by the self pollination of J2592, Q2500 or ME #1. Thus, activation of MEA-15G-ESA1 by J2592 and Q2500 is responsible for these vegetative developmental effects.

TABLE 5

Segregation of seed phenotypes in developing siliques

| Cross ID | Line ID | # Green seed | # White seed | # Aborted ovules | Total seeds |
|---|---|---|---|---|---|
| F1(ME #1 x J2592) | Plant #1 | | | | |
| | AVG | 17.4 | 6 | 14.4 | 37.8 |
| | % | 46.0 | 15.9 | 38.1 | 100 |
| F1(ME #1 x J2592) | Plant #2 | | | | |
| | AVG | 17.2 | 6.3 | 15.9 | 39.4 |
| | % | 43.7 | 16.0 | 40.4 | 100 |
| F1(ME #1 x J2592) | Plant #3 | | | | |
| | AVG | 23 | 0 | 15 | 38 |
| | % | 60.5 | 0.0 | 39.5 | 100 |
| F1(ME #1 x J2592) | Plant #22 | | | | |
| | AVG | 18.5 | 59 | 14.8 | 39.2 |
| | % | 47.2 | 15.1 | 37.8 | 100 |
| F1(ME #1 x J2592) | Plant #24 | | | | |
| | AVG | 24.6 | 0 | 15.5 | 40.1 |
| | % | 61.3 | 0.0 | 38.7 | 100 |
| Control (GFP negative) | Plant #26 | | | | |
| | AVG | 43.2 | 0 | 0.2 | 43.4 |
| | % | 99.5 | 0.0 | 0.5 | 100 |

| Cross ID | Line ID | # Green seed | # White seed | # Aborted ovules | Total est. |
|---|---|---|---|---|---|
| F1(J2592 X ME #1) | Plant #14 | | | | |
| | AVG | 24.2 | 0.1 | 14.8 | 39.1 |
| | % | 61.9 | 0.3 | 37.9 | 100 |
| F1(J2592 X ME #1) | Plant #26 | | | | |
| | AVG | 15 | 6.2 | 16 | 37.2 |
| | % | 40.3 | 16.7 | 43.0 | 100 |
| F1(J2592 X ME #1) | Plant #34 | | | | |
| | AVG | 15.9 | 6.7 | 15.2 | 37.8 |
| | % | 42.1 | 17.7 | 40.2 | 100 |
| F1(ME #1 x J0661) | Plant #32 | | | | |
| | AVG | 15.9 | 0 | 12.4 | 28.3 |
| | % | 56.2 | 0.0 | 43.8 | |

TABLE 5-continued

| | | | | | |
|---|---|---|---|---|---|
| F1(J0661 x ME #1) | Plant #19 | | | | |
| | AVG | 17.8 | 0 | 17.5 | 35.3 |
| | % | 50.4 | 0.0 | 49.6 | |
| F1(J0661 x ME #1) | Plant #27 | | | | |
| | AVG | 18.6 | 0 | 15.4 | 34 |
| | % | 54.7 | 0.0 | 45.3 | |
| F1(J0661 x ME #1) | Plant #28 | | | | |
| | AVG | 18.2 | 0.1 | 16.8 | 35.1 |
| | % | 51.9 | 0.3 | 47.9 | |

Example 9

Fertilization Independent Seed Development

To determine the frequency of post-fertilization seed abortion, siliques harvested at two weeks and at four weeks after self-pollination were dissected, and wild-type and aborted seeds were counted. To test for fertilization-independent development, flower buds from plants that had not yet begun to shed pollen (i.e., stage 12 plants) (see Smyth, D. R., et al., *Plant Cell*, 2: 755-761 (1990)) were opened, immature anthers were removed, and the flower bud was covered with a plastic bag. In some experiments, the silique was measured, dissected, and the number of seed-like structures and degenerated ovules were counted after seven days. In some experiments, the silique was harvested and ovules and seed-like structures were phenotyped after 15 days.

When immature $F_1$(J2592×FE #1) flowers were emasculated and allowed to develop, seed-like structures were observed that were filled with endosperm but contained no embryo. This occurred in roughly 40 percent of the siliques analyzed. Thus, activation of FIE-15G-ESA1 by J2592 also can induce fertilization independent endosperm and seed development.

Example 10

Profiling Gene Expression

This example demonstrates the use of chimeric polypeptides for RNA expression profiling. Gene expression in developing flowers from $F_1$ (J2592×FE #1) was compared to gene expression in flowers from activation line J2592 (see Table 3) and target line FE #1 using microarray expression analysis. All experiments were done in duplicate.

Sample preparation: Seeds of $F_1$ (J2592×FE #1) plants were sterilized in 95% bleach for 1 minute and with 70% ethanol for 45 seconds and subsequently washed 5 times in sterile distilled deionized water and then plated on MS agar plates and left at 4° C. for 4 days to be vernalized. Plates were placed in growth chamber with 16 hr light/8 hr. dark, 23° C., 14,500-15,900 LUX, and 70% relative humidity for germination and growth. Seedlings were PCR-genotyped for the presence of the transgene and analyzed using dissecting microscopy for GFP expression before they were transplanted individually into soil. Tissues harvested for RNA extraction consisted of compact terminal inflorescences. Each sample contained a population of sequentially produced and continuously developing flowers representing all stages of flower development from early floral primordial, to immature floral buds, to mature flowers up to and including two days after pollination. Samples were flash frozen in liquid nitrogen and stored at −80° C. until use. Total RNA was extracted using Qiagen RNeasy Kit with the protocol recommended by manufacture and the RNA was then dissolved in RNA-free water.

Approximately 10 μg of the each RNA sample was used for amplification using MessageAmp™ aRNA Kit provided by Ambion, Inc. Poly(A+) mRNA was isolated using standard procedures (Poly(A) Quick mRNA Isolation Kit (Stratagene, La Jolla, Calif.), and 2 μg from each sample was used to generate labeled probes for hybridization to microarray slides containing *Arabidopsis* cDNA sequences. The *Arabidopsis* microarray contained nucleic acid features representing 10,000 different *Arabidopsis* genes. Hybridization experiments to detect differentially regulated genes were set up in pairs. For example, RNA from the $F_1$ (J2592×FE #1) plant was compared to RNA from either the *Arabidopsis* activation line J2592 or the *Arabidopsis* transgenic line FE#1. Expression results are analyzed using standard software and procedures.

Slide preparation: Microarray technology provides the ability to monitor mRNA transcript levels of thousands of genes in a single experiment. These experiments simultaneously hybridize two differentially labeled fluorescent cDNA pools to glass slides that have been previously spotted with cDNA clones of the same species. Each arrayed cDNA spot will have a corresponding ratio of fluorescence that represents the level of disparity between the amount of respective mRNA species in the two sample pools. Thousands of polynucleotides can be spotted on one slide, and each experiment analyzes the expression pattern of thousands of mRNA species.

The microarray utilizes a chemically coated microscope slide, referred herein as a "chip" with numerous polynucleotide samples arrayed at a high density. The coating with chemicals such as Poly-L-lysine allows for spotting DNA at high density by providing a hydrophobic surface, reducing the spreading of spots of DNA solution arrayed on the slides. Glass microscope slides (Gold Seal #3010 manufactured by Gold Seal Products, Portsmouth, N.H., USA) were coated with a 0.1% W/V solution of Poly-L-lysine (Sigma, St. Louis, Mo.) using the following protocol:

Slides were placed in slide racks (Shandon Lipshaw #121). The racks were then put in chambers (Shandon Lipshaw #121). Cleaning solution was prepared by dissolving 70 g NaOH in 280 mL ddH2O. 420 mL 95% ethanol was added. The total volume was 700 mL (=2×350 mL) and the solution was stirred until completely mixed. If the solution remained cloudy, ddH$_2$O was added until the solution cleared. The cleaning solution was poured into chambers with slide racks, and the chambers were covered with glass lids. The solution was mixed on an orbital shaker for 2 hr. The racks were quickly transferred to fresh chambers filled with ddH$_2$O and were rinsed vigorously by plunging racks up and down. Rinses were repeated 4 times with fresh ddH$_2$O each time, to remove NaOH-ethanol. Poly-L-lysine solution was prepared by adding 70 mL poly-L-lysine stock solution to 70 mL tissue culture PBS in 560 mL double-distilled deionized water using plastic graduated cylinders and beakers. Slides were transferred to polylysine solution and shaken on an orbital shaker for 1 hr. The rack was transferred to a fresh chamber filled with ddH$_2$O, and was plunged up and down 5 times to rinse. The slides were centrifuged on microtiter plate carriers (paper towels were placed below the rack to absorb liquid) for 5 min.@ 500 rpm. The slide racks were transferred to empty chambers with covers, and were dried in a 45° C. oven for 10 min. The slides were stored in a closed plastic slide box in the dark. Normally, the surface of lysine coated slides was not very hydrophobic immediately after this process, but became increasingly hydrophobic with storage. A hydrophobic surface helped ensure that spots did not run together while printing at high densities. After they aged for 10 days to a month the slides were ready for use. Stored slides that developed opaque patches, visible when held to the light, can result in high background hybridization from the fluorescent probe and were not used.

PCR amplification of cDNA clones: Polynucleotides were amplified from *Arabidopsis* cDNA clones using one insert specific primer and one common primer that hybridized to the cloning site. The resulting 100 µl PCR reactions were purified with Qiaquick 96 PCR purification columns (Qiagen, Valencia, Calif., USA) and eluted in 30 µL of 5 mM Tris. 8.5 µL of the elution were mixed with 1.5 µL of 20×SSC to give a final spotting solution of DNA in 3×SSC. The concentrations of DNA generated from each clone varied between 10-100 ng/µl, but were usually about 50 ng/µl.

Arraying PCR products on slides: Purified PCR products were spotted onto poly-L-Lysine coated glass slides using an arrangement of quill-tip pins (ChipMaker 3 spotting pins; Telechem International, Inc., Sunnyvale, Calif., USA) and a robotic arrayer (PixSys 3500, Cartesian Technologies, Irvine, Calif., USA). Approximately 0.5 nl of a prepared PCR product was spotted at each location to produce spots having a diameter of about 100 µm. Spot were spaced 180 µm to 210 µm center-to-center. Printing was conducted in a chamber with relative humidity set at 50%. Slides containing maize sequences were purchased from Agilent Technology (Palo Alto, Calif. 94304).

Slide processing: After arraying, slides were processed through a series of steps prior to hybridization: rehydration, UV cross-linking, blocking and denaturation. Slides were rehydrated by placing them over a beaker of warm (55° C.) water (DNA face down), for 2-3 sec to distribute the DNA evenly within the spots, and then snap dried on a hot plate (DNA side face up). The DNA was cross-linked to the slides by UV irradiation (60-65 mJ; 2400 Stratalinker, Stratagene, La Jolla, Calif., USA). A blocking step was performed to modify remaining free lysine groups, and hence minimize their ability to bind labeled probe DNA. To achieve this, the arrays were placed in a slide rack. An empty slide chamber was left ready on an orbital shaker. The rack was bent slightly inwards in the middle, to ensure the slides would not run into each other while shaking. The blocking solution was prepared as follows:

Three 350-ml glass chambers (with metal tops) were set to one side, and a large round Pyrex dish with dH$_2$O was placed ready in the microwave. At this time, 15 ml sodium borate was prepared in a 50 ml conical tube. 6 g succinic anhydride was dissolved in about 325-350 mL 1-methyl-2-pyrrolidinone. Rapid addition of reagent was important. Immediately after the last flake of the succinic anhydride dissolved, 15-mL sodium borate was added. Immediately after the sodium borate solution mixed in, the solution was poured into an empty slide chamber. The slide rack was plunged rapidly and evenly in the solution and was vigorously shaken up and down for a few seconds, making sure slides never left the solution. It was mixed on an orbital shaker for 15-20 min. Meanwhile, the water in the Pyrex dish (enough to cover slide rack) was heated to boiling. Following this, the slide rack was gently plunged into 95° C. water for 2 min. The slide rack then was plunged 5times in 95% ethanol. The slides and rack were centrifuged for 5 min. at 500 rpm. Slides were loaded quickly and evenly onto the carriers to avoid streaking, and were used immediately or were stored in a slide box.

Hybridization: The hybridization process began with the isolation of mRNA from the two tissues followed by their conversion to single stranded cDNA (see "Generation of probes for hybridization", below). The cDNA from each tissue was independently labeled with a different fluorescent dye and then both samples were pooled together. This final differentially labeled cDNA pool was then placed on a processed microarray and allowed to hybridize (see "Hybridization and wash conditions", below).

Preparation of Yeast control mRNA: Plasmid DNA was isolated from the following yeast clones using Qiagen filtered maxiprep kits (Qiagen, Valencia, Calif.): YAL022c (Fun26), YAL031c(Fun21), YBR032w, YDL131w, YDL182w, YDL194w, YDL196w, YDR050c and YDR116c. Plasmid DNA was linearized with either BsrBI (YAL022c(Fun26), YAL031c(Fun21), YDL131w, YDL182w, YDL194w, YDL196w, YDR050c) or AflIII (YBR032w, YDR116c).

The following solution was incubated at 37° C. for 2 hours: 17 µl isolated yeast insert DNA (1 µg), 20 µl 5× buffer, 10 µl 100 mM DTT, 2.5 µl (100 U) RNasin, 20 µl mM (ea.) rNTPs, 2.7 µl (40U) SP6 polymerase and 27.8 µl RNase-free deionized water. Two µl (2 U) Ampli DNase I was added and the incubation continued for another 15 min. Ten µl 5M NH$_4$OAC and 100 phenol:chloroform:isoamyl alcohol (25:24:1) were added, and the solution was vortexed and centrifuged to separate the phases. To precipitate the RNA, 250 µl ethanol was added and the solution was incubated at −20° C. for at least one hour. The sample was then centrifuged for 20 min. at 4° C. at 14,000-18,000×g, the pellet was washed with 500 µl of 70% ethanol, air dried at room temperature for 10 min. and resuspended in 100 µl of RNase-free deionized water. The precipitation procedure was repeated one time.

Alternatively, after the two-hour incubation, the solution was extracted with phenol/chloroform once before adding 0.1 volume 3M sodium acetate and 2.5 volumes of 100% ethanol. The solution was centrifuged at 15,000 rpm, 4° C. for 20 min. and the pellet resuspended in RNase-free deionized water. The DNase I treatment was carried out at 37° C. for 30 min. using 2 U of Ampli DNase I in the following reaction condition: 50 mM Tris-HCl (pH 7.5), 10 mM MgCl$_2$. The DNase I reaction was then stopped with the addition of NH$_4$OAC and phenol:chloroform:isoamyl alcohol (25:24:1), and RNA isolated as described above.

0.15-2.5 ng of the in vitro transcript RNA from each yeast clone was added to each plant mRNA sample prior to labeling to serve as positive (internal) probe controls.

Generation of labeled probes for hybridization from first-strand cDNA: Hybridization probes were generated from isolated mRNA using an Atlas™ Glass Fluorescent Labeling Kit (Clontech Laboratories, Inc., Palo Alto, Calif., USA). This entails a two step labeling procedure that first incorporates primary aliphatic amino groups during cDNA synthesis and then couples fluorescent dye to the cDNA by reaction with the amino functional groups. Briefly, 5 µg of oligo(dT)$_{18}$ primer d(TTTTTTTTTTTTTTTTTTV)(oligo dTV; SEQ ID NO:1) was mixed with Poly A+ mRNA (1.5-2 µg mRNA isolated using the Qiagen Oligotex mRNA Spin-Column protocol or the Stratagene Poly(A) Quik mRNA Isolation protocol (Stratagene, La Jolla, Calif., USA) in a total volume of 25 µl. The sample was incubated in a thermocycler at 70° C. for 5 min., cooled to 48° C. and 10 µl of 5×cDNA Synthesis Buffer (kit supplied), 5 µl 10×dNTP mix (dATP, dCTP, dGTP, dTTP and aminoallyl-dUTP; kit supplied), 7.5 µl deionized water and 2.5 µl MMLV Reverse Transcriptase (500 U) added. The reaction was then incubated at 48° C. for 30 min., followed by a 1 hr incubation at 42° C. At the end of the incubation, the reaction was heated to 70° C. for 10 min., cooled to 37° C. and 0.5 µl (5 U) RNase H added, before incubating for 15 min. at 37° C. The solution was vortexed for 1 min. after the addition of 0.5 µl 0.5 M EDTA and 5 µl of QuickClean Resin (kit supplied) then centrifuged at 14,000-18,000×g for 1 min. After removing the supernatant to a 0.45 µm spin filter (kit supplied), the sample was again centrifuged at 14,000-18,000×g for 1 min., and 5.5 µl 3 M sodium acetate and 137.5 µl of 100% ethanol added to the sample before incubating at −20° C. for at least 1 hr. The sample was then centrifuged at 14,000-18,000×g at 4° C. for 20 min., the resulting pellet washed with 500 µl 70% ethanol, air-dried at room temperature for 10 min. and resuspended in 10 µl of 2×fluorescent labeling buffer (kit provided). 10 µl each of the fluorescent dyes Cy3 and Cy5 (Amersham Pharmacia, Piscataway, N.J., USA); prepared according to Atlas™ kit directions of Clontech) were added and the sample incubated in the dark at room temperature for 30 min. to 1 hr.

The fluorescently labeled first strand cDNA was precipitated by adding 2 µl 3M sodium acetate and 50 µl 100% ethanol, incubated at −20° C. for at least 2 hrs, centrifuged at 14,000-18,000×g for 20 min., washed with 70% ethanol, air-dried for 10 min. and dissolved in 100 µl of water. Alternatively, 3-4 µg mRNA, 2.5 (~8.9 ng of in vitro translated mRNA) µl yeast control and 3 µg oligo dTV (TTTTTTTTTTTTTTTTTTV; SEQ ID NO:1) were mixed in a total volume of 24.7 µl. The sample was incubated in a thermocycler at 70° C. for 10 min. before chilling on ice. To this, 8 µl of 5×first strand buffer (SuperScript II RNase H-Reverse Transcriptase kit from Invitrogen, Carlsbad, Calif. 92008; cat no. 18064022), 0.8 µl of aa-dUTP/dNTP mix (50×; 25 mM dATP, 25 mM dGTP, 25 mM dCTP, 15 mM dTTP, 10 mM aminoallyl-dUTP), 4 µl of 0.1 M DTT and 2.5 µl (500 U) of Superscript R.T.II enzyme (Stratagene) were added. The sample was incubated at 42° C. for 2 hours before a 10° C. mixture of 1M NaOH and 0.5 M EDTA was added. After a 15 minute incubation at 65° C., 25 µl of 1 M Tris pH 7.4 was added. This was mixed with 450 µl of water in a Microcon 30 column before centrifugation at 11,000×g for 12 min. The column was washed twice with 450 µl (centrifugation at 11,000 g for 12 min.) before eluting the sample by inverting the Microcon column and centrifuging at 11,000×g for 20 seconds. Sample was dehydrated by centrifugation under vacuum and stored at −20° C.

Each reaction pellet was dissolved in 9 µl of 0.1 M carbonate buffer (0.1 M sodium carbonate and sodium bicarbonate, pH=8.5-9) and 4.5 ill of this was placed in two microfuge tubes. 4.5 µl of each dye (in DMSO) was added, and the mixture was incubated in the dark for 1 hour. 4.5 µl of 4 M hydroxylamine was added and the mixture was again incubated in the dark for 15 min.

Irrespective of the method used for probe generation, the probe was purified using a Qiagen PCR cleanup kit (Qiagen, Valencia, Calif., USA), and eluted with 100 ul EB (kit provided). The sample was loaded on a Microcon YM-30 (Millipore, Bedford, Mass., USA) spin column and concentrated to 4-5 ul in volume. Probes for the maize microarrays were generated using the Fluorescent Linear Amplification Kit (cat. No. G2556A) from Agilent Technologies (Palo Alto, Calif.).

Hybridization Conditions: Labeled probe was heated at 95° C. for 3 min. and was then chilled on ice. Then, 25 µl of the hybridization buffer which was warmed at 42° C. was added to the probe and was mixed by pipetting to give a final concentration of: 50% formamide, 4×SSC, 0.03% SDS, 5×Denhardt's solution, and 0.1 µg/ml single-stranded salmon sperm DNA. The probe was kept at 42° C. Prior to hybridization, the probe was heated for 1 min., added to the array, and then covered with a glass cover slip. Slides were placed in hybridization chambers (Telechem International, Sunnyvale, Calif.) and incubated at 42° C. overnight.

Washing conditions: Slides first were washed in 1×SSC+ 0.03% SDS solution at room temperature for 5 min. Slides then were washed in 0.2×SSC at room temperature for 5 min. Slides finally were washed in 0.05×SSC at room temperature for 5 min. Slides then were spun at 800×g for 2 min. to dry. They were then scanned.

Scanning of slides: Chips were scanned using a ScanArray 3000 or 5000 (General Scanning, Watertown, Mass., USA). The chips were scanned at 543 nm and at 633 nm at a resolution of 10 µm to measure the intensity of the two fluorescent dyes incorporated into the samples hybridized to the chips.

Data extraction and analysis: The images generated by scanning slides consisted of two 16-bit TIFF images representing the fluorescent emissions of the two samples at each arrayed spot. These images were quantified and processed for expression analysis using Imagene™ (Biodiscovery, Los Angeles, Calif., USA) data extraction software. Imagene™ output was using the Genespring™ (Silicon Genetics, San Carlos, Calif., USA) analysis software. In Genespring™, the data was imported using median pixel intensity measurements derived from Imagene™ output. Ratio calculation and normalization were conducted using Genespring™ Normalization was achieved by parsing the data into 32 groups, each of which represented one of the 32 pin printing regions on the microarray. Each group consisted of about 360 to 550 spots, and was independently normalized by setting the median of ratios to one and multiplying ratios by the appropriate factor.

Results: Among the ten thousand genes represented on the DNA chip, the expression ratio of 152 genes (1.52%) was found to be reduced at least 2-fold in $F_1$ (J2592×FE #1) floral tissue when compared to floral tissue from FE #1. Similarly, the expression ratios of 63 genes (0.63%) were found to be down at least 2-fold in $F_1$ (J2592×FE #1) floral tissue when compared to floral tissue from J2592. By contrast, the expression ratio of 227 genes (2.27%) was increased more than 2-fold in $F_1$ (J2592×FE #1) floral tissue when compared to floral tissue from FE #1. Similarly, 39 genes (0.39%) were found to be up at least 2-fold in $F_1$ (J2592×FE #1) compared to J2592 floral tissue.

Example 11

Analysis of FIE-15G-ESA1 Activated Plants

The FIE-15G-ESA1 transgene is transcriptionally activated by crossing female FE plants containing a FIE-15G-ESA1 transgene to enhancer trap HAP1-VP16 lines that display cell and tissue specific GFP accumulation in vegetative and reproductive organs. FE plants are crossed with four different activation lines. A different enhancer is present in each of the lines and confers expression of the HAP 1-VP 16 transcription activator, as well as the GFP, in a different set of tissues. The amino acid sequence of the HAP1 portion of the HAP 1-VP 16 transcription activator is that of the yeast HAP 1 gene. The activity of each enhancer-trap line is inferred from the GFP fluorescence.

At maturity, $F_1$ seeds are collected and stored under standard conditions. A reciprocal cross is also made, in which FE plants are used as males.

$F_1$ seeds are germinated and allowed to self-pollinate. After pollination, some of the embryos and seeds developing on $F_1$ plants are examined under a microscope. Mature seed also are analyzed as described in Example 7. Seedlings are scored for GFP expression and tested for the presence of FIE-15G-ESA1 by PCR. Phenotypic traits are analyzed as described in Example 7.

REFERENCE LIST

Aalfs, J. D. and Kingston, R. E. (2000) *Trends Biochem Sci.* 25:548-55.
Cress W. D. and Seto, E. (2000) *J. Cell Physiol.* 184:1-16.
Amedeo, P., Habu, Y., Afsar, K., Scheid, O. M. and Paszkowski, J. (2000) *Nature* 405:203-206.
Cao, X., Springer, N. M., Muszynski, M. G., Phillips, R. L., Kaeppler, S. and Jacobsen, S. E. (2000) *Proc. Natl. Acad. Sci. USA* 97:4979-4984.
Butler, K. H., Danilevskaya, O., Miao, G-H., Morgante, M., Sakai, H., Simmons, C. R., Weng, Z. (2001) PCT WO 0116325.
Davie, J. R. and Moniwa, M., (2000) *Crit Rev Eukaryot Gene Expr.* 10:303-325.
Dellaporta, S. L. and Chen, J. (2000) U.S. Pat. No. 6,011,200.
Farkas, G. et al. (2000) *Gene.* 253:117-36.
Fischer, R. L., Ohad, N., Kiyosue, T., Yadegari, R., Margossian, L., Harada, J. J., Goldberg, R. B. (2001) U.S. Pat. No. 6,229,064.
Flaus, A. and Owen-Hughes, T. (2001) *Curr Opin Genet Dev.* 11:148-54.
Fry, C. J. and Peterson, C. L. (2001) *Curr Biol.* 11:R185-97.
Gregory, P. D. et al. (2001) *Exp Cell Res.* 265:195-202.
Grossniklaus, U., Vielle-Calzada, J-P., Hoeppner, M. A. and Gagliano, W. B. (1998) *Science* 280:446-450.
Grossniklaus, U. and Vielle-Calzada, J-P. (2001) U.S. Pat. No. 6,239,327
Haseloff, J., Siemering, K. R., Prasher, D. C. and Hodge, S. (1997) *Proc. Natl. Acad. Sci. USA* 94:2122-2127
Jackson, J. P., Lindroth, A. M., Cao, X. and Jacobsen, S. E. (2002) *Nature* 416:556-560.
Jeddeloh, J. A., Stokes, T. L. and Richards, E. J. (1999) *Nature Genetics* 22:94-97.
Kiyosue, T., Ohad, N., Yadegari, R., Hannon, M., Dinneny, J., Wells, D., Katz, A., Margossian, L., Harada, J. J., Goldberg, R. B. and Fischer, R. L. (1999) *Proc. Natl. Acad. Sci. USA* 96:4186-4191.
Krebs, J. E. and Peterson, C. L. (2000) *Crit Rev Eukaryot Gene Expr.* 10:1-12.
Lindroth A M, Cao X, Jackson J P, Zilberman D, McCallum C M, Henikoff S, Jacobsen S E. (2001) *Science* 292:2077-2080.
Liu, Z-B. and Odell, J. T. (1999) U.S. Pat. No. 5,968,793.
Luo, M., Bilodeau, P., Dennis, E. S., Peacock, W. J. and Chaudhury, A. (2000) *Proc. Natl. Acad. Sci. USA* 97:10637-10642.
Muller, C. and Leutz, A. (2001) *Curr Opin Genet Dev.* 11:167-74.
Ohad, N., Yadegari, R., Margossian, L., Hannon, M., Michaeli, D., Harada, J. J., Goldberg, R. B.
and Fischer, R. L. (1999) *The Plant Cell* 11:407-415.
Richards, E. J., Jeddeloh, J. A. U.S. Pat. No. 6,153,741.
Roseman, R.R., Morgan, K., Mallin, D. R., Roberson, R., Parnell, T. J., Bomemann, D. J., Simon, J. A. and Geyer, P. K. (2001) *Genetics* 158:291-307.
Springer, N. M., Danilevskaya, O. N., Hermon, P., Helentjaris, T. G., Phillips, R. L., Kaeppler, H. F., and Kaeppler, S. M. (2002) *Plant Physiology* 128:1332-1345.
Vielle-Calzada, J-P., Thomas, J., Spillane, C., Coluccio, A., Hoeppner, M. A. and Grossniklaus, U. (1999) *Genes & Dev.* 13:2971-2982.
Vinkenoog, R., Spielman, M., Adams, S. Fischer, R. L., Dickinson, H. G. and Scott, R. J. (2000) *The Plant Cell* 12:2271-2282.
Wu, K., Tian, L., Malik, K., Brown, D. and Miki, B. (2000) *The Plant Journal* 22:19-27.
Wu, K., Miki, B. L. A., Tian, L., Brown, D. C. W. (2001) European Patent Application 1094112A2.

TABLE 6

HAT Polypeptide Sequences

Arabidopsis ESA1-like

MGSSANTETNGNAPPPSSNQKPPATNGVDGSHPPPPPLTPDQAIIESDPSKKRKMGMLPLEVGTRVMC

RWRDGKHHPVKVIERRRIHNGGQNDYEYYVHYTEPNRRLDEWTQLDQLDLDSVECAVDEKLEDKVTSL

KMTRHQKRKIDETHIEGHEELDAASLREHEEFTKVKNISTIELGKYEIETWYFSPFPPEYNDCVKLFF

CEFCLNFMKRKEQLQRHMXKCDLKHPPGDEIYRSGTLSMFEVDGKKNKVYAQNLCYLAKLFLDHKTLY

YDVDLFLFYVLCECDDRGCHMVGYFSKEKHSEEAYNLACILTLPSYQRKGYGKFLIAFSYELSKKEGK

VGTPXKTLVGSRLTKLQRLLDSCSIRNLEKT

TABLE 6-continued

HAT Polypeptide Sequences (SEQ ID NO:2)

Maize HAC000003

MDSHSSHLNAANRSRSSQTPSPSHSASASVTSSLHKRKLAATTAANAAASEDHAPPSSSFPPSSFSAD

TRDGALTSNDELESISARGADTDSDPDESEDIVVDDDEDEFAPEQDQDSSIRTFTAARLDSSSGVNGS

SRNTKLKTESSTVKLESSDGGKDGGSSVVGTGVSGTVGGSSISGLVPKDESVKVLAENFQTSGAYIAR

EEALKREEQAGRLKFVCYSNDSIDEHMMCLIGLKNIFARQLPNMPKEYIVRLLMDRKHKSVMVLRGNL

VVGGITYRPYHSQKFGEIAFCAITADEQVKGYGTRLMNHLKQHARDVDGLTHFLTYADNNAVGYFVKQ

EIPQSFTSKSSVSTLSYQGFTKEIYLEKDVWHGFIKDYDGGLLMECKIDPKLPYTDLSSMIRQQRKAI

DERIRELSNCQNVYPKIEFLKNEAGIPRKIIKVEEIRGLREAGWTPDQWGHTRFKLFNGSADMVTNQK

QLNALMRALLKTMQDHADAWPFKEPVDSRDVPDYYDIIKDPIDLKVIAKRVESEQYYVTLDMFVADAR

RMFNNCRTYNSPDTIYYKCATRLETHFHSKVQAGLQSGAKSQ (SEQ ID NO:3)

Arabidopsis HAT1

MSVHVKEEPVLVPNCDVENTELAVFNGNGESELENFGTCVDEITDRVNQLEQKVVEVEHFYSTKDGAA

QTNTSKSNSGGKKIAISQPNNSKGNSAGKEKSKGKHVSSPDLMRQFATMFRQIAQHKWAWPFLEPVDV

KGLGLHDYYKVIEKPMDLGTIKKKMESSEYSNVREIYADVRLVFKNAMRYNEEKEDVYVMAESLLEKF

EEKWLLIMPKLVEEEKKQVDEEAEKHANKQLTMEAAQAEMARDLSNELYEIDLQLEKLRESVVQRCRK

LSTQEKKGLSAALGRLSPEDLSKALKMVSESNPSFPAGAPEVELDIDVQTDVTLWRLKVFVQEALKAA

NKSSGGTNAQNNNNTGTGEINKNNAKRRREISDAINKASIKRAKKA (SEQ ID NO:4)

TABLE 7

CAP/HDAC Gene and Polypeptide Sequences

MEA, GI:3089625

MEKENHEDDG EGLPPELNQI KEQIEKERFL HIKRKFELRY IPSVATHASH HQSFDLNQPA AEDDNGGDNK SLLSRMQNPL

RHFSASSDYN SYEDQGYVLD EDQDYALEED VPLFLDEDVP LLPSVKLPIV EKLPRSITWV FTKSSQLMAE SDSVIGKRQI

YYLNGEALEL SSEEDEEDEE EDEEEIKKEK CEFSEDVDRF IWTVGQDYGL DDLVVRRALA KYLEVDVSDI LERYNELKLK

NDGTAGEASD LTSKTITTAF QDFADRRHCR RCMIFDCHMH EKYEPESRSS EDKSSLFEDE DRQPCSEHGY LKVRSVTEAD

HVMDNDNSIS NKTVVSDPNN TMWTPVEKDL YLKGIEIFGR NSCDVALNIL RGLKTCLETY NYMREQDQCT MSLDLNKTTQ

RHNQVTKKVS RKSSRSVRKK SRLRKYARYP PALKKTTSGE AKFYKHYTPC TCKSKCGQQC PCLTHENGCE KYCGCSKDCN

NRFGGCNCAI GQCTNRQCPC FAANRECDPD LCRSCPLSCG DGTLGETPVQ IQCKNMQFLL QTNKKILIGK SDVHGWGAFT

WDSLKKNEYL GEYTGELITH DEANERORTE DRIGSSYLFT LNDQLEIDAR RRGNEFKFLN NSARPNCYAK LMIVRGDQRI

GLFAERAIEE GEELFFDYCY GPEHADWSRG REPRRTGASK RSKEARPAR (SEQ ID NO:5)

F152, GI:4185501

MTLKAEVVEN FSCPFCLIPC GGHEGLQLHL KSSHDAFKFE FYRAEKDHGP EVDVSVKSDT IKFGVLKDDV GNPQLSPLTF

CSRNRNQRRQ RDDSNNVKKL NVLLMELDLD DLPRGTENDS THVNDDNVSS PPRAHSSEKI SDILTTTQLA TAESSEPKVP

HVNDGNVSSP PRAHSSAEKN ESTHVNDDDD VSSPPRAHSL EKNESTHVNE DNISSPPRAN SSKKNESTHM NDEDVSFPPR

TABLE 7-continued

CAP/HDAC Gene and Polypeptide Sequences

TRSSKETSDI LTTTQRAIVE PSEPKVRRGS RRKQLYAKRY KARETQPAIA ESSEPKVLHV NDENVSSPPE ANSLERASOI

LTTTQPAIAE SSEPKVPHVN DENVSSTPRA HSSKKNKSTR RNVDNVPSPP KTRSSKKTSD ILTTTQPTIA ESSEPRVRHV

NDDNVSSTPR AHSSKRNKST RKNDDNIPSP PKTRSSRKTS NILTRTQPAI AESEPKVPHV NDDKVSSTFR AHSSKKNKST

HKKDDNASLP PKTRSSKKTS DILATTQPAK AEPSEPKVTR VSRRKELHAE RCEAKRLERL KGRQFYHSQT MQPMTFEQVM

SNEDSENETD DYALDISERL RLERLVGVSK EEKRYMYLWN IFVRKQRVIA DGHVPWACEE FAKLHKEEMK NSSSFDWWWR

MFRIKLWNNG LICAKTFHKC TTILLSNSDE AGQFTSGSAA NANNQQSMEV DE (SEQ ID NO:6)

FIE, GI:4567095

MSKITLGNES IVGSLTPSNK KSYKVTNRIQ EGKKPLYAVV FNFLDARFFD VFVTAGGNRI TLYNCLGDGA ISALQSYADE

DKEESFYTVS WACGVNGNPY VAAGGVKGII RVIDVNSETI HKSLVGHGDS VNEIRTQPLK PQLVITASKD ESVRLWNVET

GICILIFAGA GGHRYEVLSV DFHPSDIYRF ASCGMDTTIK IWSMKEFWTY VEKSFTWTDD PSKFPTKFVQ FPVFTASIHT

NYVDCNRWFG DFILSKSVDN EILLWEPQLK ENSPGEGASD VLLRYPVPMC DIWFIKFSCD LHLSSVAIGN QEGKVYVWDL

LSCPPVLITK LSHNQSKSVI RQTAMSVDGS TILACCEDGT IWRWDVITK (SEQ ID NO:7)

Multi sex combs (mxc), AT5g46250

MESPSISDAVPLHAPEDATADFSQPQSPLHEVDSFPVTESSDDVVVNVSEIPNLSPSDDDFDHERNSGEDRDQDHGENPVETDGVVVPIDELNQKII

RQVEYYFSDENLPTDKFLLNAMKRNKKGFVPISTIATFHKMKKLTRDHALIVSALKESSFLVVSADEKKVKRLSPLPEIRDPKIFTVLVENLPEDHS

NENIREIFGKAGSIKSVSICDPNAVEESEKGGKKENFIRTRLHAFVEYETVEAAEKAAATLNNEQDWRNGLRVKLLEQAAGKFAQRRPARREVDKEK

DTTGRVHDQTGGEKNKKTREHQNHRLHHSDNPADDDGGNHQKDKNGNKGRVVGQGRRQNHQGGNGIGHGTASSSSHPNYHPVEVSKRPPGPRMPDGT

RGFTMGRGKAIPPPTSTQTSHEV (SEQ ID NO:8)

Arabidposis TS01-like, GI:7767427

MDTPEKSETQ TGTPVSKLKV EDSPVFSYIC NLSPIKTIKP IPITCPLSSL NYASPPSVFT SPHAVSHKES RFRSQKDVSA

SKEVOEREAL VGSEPEQSYK NDCNTPRVLN DVKDNGCGKD LQVMMDNVKK KSDTFDWETL IAATTELIYG SPRESEAFSC

LLKKTSNSEA RLRGSITATS VAVTNTDVVN NESESYDALS ILNRGVRRRC LDFEVKGNNQ QTLGESSSSC VVPSTGLHLN

TIAMSSKDKN VANEYSFSGN IKVGVQSSLT PVLHSQNDIV RENESGKDSG QITEVVRKSL ASVDLTPISP KKKRRKSEQS

GEGDSSCKRC NCKKSKCLKL YCECFAAGFY CIEPCSCINC FNKPIHKDVV LATRKQIESR NPLAFAPKVI RNSDSIIEVG

EDASKTPASA RHKRGCNCKK SNCLKKYCEC YQGGVGCSTN CRCEGCKNAF GRKDGSLFEQ DEENETSGTP GTKKTQQNVE

LFKPAAPPST PIPFRQPLAQ LPISSNNRLL PPQSHFHHGA IGSSSSGIYN IRKPDMSLLS HSRIETITED IDDMSENLIH

SPITTLSPNS KRVSLSNLDS PESTPWRRNG EGRNLIRSFP TFPSLTFHH (SEQ ID NO:9)

Sin3, F3I6.12

MVGGGSAQKLTTNDALAYLKAVKDKFQDQRGKYDEFLEVMKNFKSQRVDTAGVITRVKELFKGNQELILGFNTFLPKGFEITLQPEDGQPPLKKRVE

FEEAISFVNKIKTRFQGDDRVYKSFLDTLNMYRRDSKSITEVYQEVAILFRDHSDLLVEFTHFLPDTSATASIPSVKTSVRERGVSLADKKDRIITP

HPDHDYGTEHIDQDRERPIKKENKEHMRGTNKENEHRDARDFEPHSKKEQFLNKQKLHIRGDDPAEISNQSKLSGAVPSSSTYDEKGAMKSYSQDL

AIVDRVKEKLNASEYQEFLRCLNLFSKEIISRPELQSLVGNLIGVYPDLMDSFIEFLVQCEKNEKRQICNLLNLLAEGLLSGILTKKSLWSEGKYPQ

PSLDNDRDQENKRDDGLRDRDHEKERLEKAAANLKWAKPISELDLSNCEQCTFSYRLLPKNYPISIASQKTEIGKLVLNDHWVSVTSGSEDYSFSHM

RKNQYEESLFKCEDDRFELDMLLESVNSTTKHVEELLTKINSNELKTNSPIRVEDHLTALNLRCIERLYGDHGLDVMDVLKKNVSLALPVILTRLKQ

KQEEWARCRSDFDKVWAEIYAKNYYKSLDHRSFYFKQQDSKKLSMKALLAEIKEITEKKREDDSLLAFAAGNRLSISPDLEFDYPDHDLHEDLYQLI

TABLE 7-continued

CAP/HDAC Gene and Polypeptide Sequences

KYSCAEMCSTEQLDKVMKIWTTFVEQIFGVPSRPQGAEDQEDVVKSMNQNVKSGSSSAGESEGSPHNYASVADSRRSKSSRKANEHSQLGQTSNSER

DGAAGRTSDALCETAQHEKMLKNVVTSDEKPESKQAVSIERAHDSTALAVDGLLDQSNGGSSIVHMTGHCNNNLKPVTCGTELELKMNDGNGPKLEV

GNKKLLTNGIAVEITSDQEMAGTSKVEREEGELSPNGDFEEDNFAVYAKTDFETFSKANDSTGNNISGDRSREGEPSCLETRAENDAEGDENAARSS

EDSRNEYENGDVSGTESGGGEDPEDDLDNNNKGESEGEACMADAHDAEENGSALPVSARFLLHVKPLVKYVPSAIALHDKDKDSLKNSQVFYGNDS

FYVLFRLHRILYERILSAKVNSSSPEGKWRTSNTKNPTDSYARFMTALNLLDGTSDNAKFEDDCRAIIGTQSYILFTLDKLIHKFIKHLQVVVADE

MDNKLLQLYFYEKSRRPETIFDAVYYDNTRVLLPDENIYRIECRLSTPAKLSIQLMCNGLDKPDVTSVSIDPTF[ ]YLENDFLSIQPNAREDRRIYL

NR (SEQ ID NO:10)

Sin3, GI:2829870

MVGGGSAQKL TTNDALAYLK AVKDKFQDQR GKYDEFLEVM KNFKSQRVDT AGVITRVKEL FKGHQELILG FNTFLPKGFE

ITLQPEDGQP PLKKRVEFEE AISFVNKIKT RFQGDDRVYK SFLDILNMYR RDSKSITEVY QEVAILFRDH SDLLVEFTHF

LPDTSATASI PSVKTSVRER GVSLADKKDR IITPHPDHDY GTEHIDQDRE RPIKKENKEH MRGTNKENEH RDARDFEPHS

KKEQFLNKKQ KLHIRCDDPA EISNQSKLSG AVPSSSTYDE KGAMKSYSQD LAIVDRVKEK LNASEYQEFL RGLNLFSKEI

ISRPELQSLV GNLTGVYPDL MDSFIEFLVQ CEKNEKRQIC NLLNLLAEGL LSGILTKKSL WSEGKYPQPS LDNDRDQEHK

RDDGLRDRDH EKERLEKAAA NLKWAKPISE LDLSNCEQCT PSYRLLPKNY PISIASQKTE IGKLVLNDHW VSVTSGSEDY

SFSHMRKNQY EESLFKCEDD RFELDMLLSS VNSTTKHVEE LLTKINSNEL KTNSPIRVED HLTALNLRGI ERLYCDHGLD

VMDVLKKNVS LALPVILTRL KQKQEEWARC RSDFDKVWAE IYAKNYYKSL DHRSFYFKQQ DSKKLSMKAL LAEIKEITEK

KREDDSLLAF AAGNRLSISP DLEFDYPDHD LHEDLYQLIK YSCAEMCSTE QLDKVMKIWT TFVEQTFGVP SRPQGAEDQE

DVVKSMNQNV KSGSSSAGES EGSPHNYASV ADSRRSKSSR KANEHSQLGQ TSNSERDGAA GRTSDALCET AQHEKMLKNV

VTSDEKPESK QAVSIERAHD STALAVDGLL DQSNGGSSIV HMTGHCNNNL KPVTCGTELE LKMNDGNGPK LEVGNKKLLT

NGTAVEITSD QEMAGTSKVE REEGELSPNG DFEEDNFAVY AKTDFETFSK ANDSTGNNIS GDRSREGEPS GLETRAENDA

EGDENAARSS EDSRNEYENG DVSGTESGGG EDPEDDLDNN NKGESEGEAE CMADAHDAEE NGSALPVSAR FLLHVKPLVK

YVPSAIALHD KDKDSLKNSQ VFYGNDSFYV LFRLHRILYE RILSAKVNSS SPEGKWRTSN TKNPTDSYAR KMTALYNLLD

GTSDNAKFED DCRATIGTQS YILFTLDKLI HKFIKHLQVV VADEMDNKLL QLYFYEKSRR PETTFDAVYY DNTRVLLPDE

NIYRIECRLS TPAKLSIQLM CNGLDKPDVT SVSTDPTFAA YLHNDFLSIQ PNARKDRRIY LNR (SEQ ID NO:11)

Arabidopsis MeCP2, GI:2827551

MNLKKSRSEN SSVASSGSKI EEQTEKSAEP TTIKVQKKAG TPGRSIDVFA VQCEKCMKWR KIDTQDEYED IRSRVQEDPF

FCKTKEGVSC EDVGDLNYDS SRTWVIDKPG LPRTPRGFKR SLILRKDYSK MDAYYITPTG KKLKSRNEIA AFIDANODYK

YALLGDFNFT VPKVMEETVP SGILSDRTPK PSRKFLSGKM QGGGGRDPFG GFGGPFGGF GGGSFGGFGR GSFGGFGGPN

GPPSLMSNFF GGRDPFDDPF FTQPFGGGMF QSNFFGPSMN PFAEMHRLPQ GFIENNQPPG PSRSRGPVTE EIDSDDEKEG

EGDKEKKGSL GKHGRSSSEA ETEDARVRER RNRQMQSMNV NAERRNRFMQ NMNVNAERRN PQMQNMNVNA MVNNGQWQPQ

TGSYSEQSST VTYGGQNGNY YTSSKTRRTG SDGGHTVARK LNSDGRVDTT QTLHNLNEGG LVNREQPMLL PSTDPSPSHA

RAESSRRPKA AMNLIPILAI AVASAAFLSE LVSMSLPESI WRMMTPKAKI SVFSVNFPVV TYSGAKYPIA ALVLSAEKTI SSARRL (SEQ ID NO:12)

Corn MBD1, GI:13936238

MTTGSTPGSAPSQRKRNSTKDSVALYAVQCYKCYKWSTVPKEEFETLRENFTKDPWFCSRRPDSSCEDDADIEYDSSRIWVLDKPNIPKPPPETERL

VVMRGDYSKMDTYYVMPNGKRARCAGDVDKFLEANPEYKDRISASDFSFAPPKVVEETVSHNPAWQAAKAKKQEKAEAQK

TABLE 7-continued

CAP/HDAC Gene and Polypeptide Sequences (SEQ ID NO:13)

Corn MBD1, GI:13936310

MPAPDGWTKKFTPQRGGRSEIVFVSPTGEEIKNKRQLSQYLKAHPGGPAASDFDWGTGDTPRRSARISEKVKVFDSPEGEKIPKRSRNSSGRKGRQG

KKEAPETEEAKDAETGQDAPSEDGTKETDVEMKPAEEEAKEAPTETDDAEKAADKADDTPAPAPMEEDEKETEKPAEAVVAPLAQSEEKKEDAKPDEP

EAVAPAPVSNPTENSAPAPAEPAAVPAPVPETESVAEPAAVLAPAPETKPDAKPAAVPAPAPENKPDAEPAAAAAPVPDTKSVAEPAAAPAPDTKSV

AEPAAAAPVPETKLVAESAADAVAAPAPETKSDAEPAAAPVPETKPVAESAADAVAAPAPETKSDAEPAAAADPAPEIKSDAAAADPAPGTKADAAA

TDAAPGAEPDAAPLENTAADKGGSEESSQPVNNVNNGHST (SEQ ID NO:14)

Rice MBD1

EITVEESKEAPTTTKEATHRISRGIHDKGHSLTRKLKSDGNVDTTQILHNLHEDELAGFEESWKGNARHHLAGLNQNAGTSNNNNQVTVAPVDVAGN

PLGVGLFLEESKAVIKDGTSEDRNHVSYQSPKGFLLYIYGSKSVNCXVVESSKIQVQRILI (SEQ ID NO:15)

Arabidopsis MBD1, GI:9392683 mddgdlgnnh hnflggagnr lsaeslplid trllsqselr alsqcsslsp sssaslaasa ggdddltpki drsvfnesag srkqtflrlr larhpqppee ppspqrqrdd ssreeqtqva sllrslfnvd snqskeeede geeeledneg qihynsyvyq rpnldsiqnv liggtsgnki krkrgrprki rnpseenevl dltgeastyv fvdktssnlg mvsrvgssgi sldsnsvkrk rgrppknkee imnlekrdsa ivnisafdke elvvnlenre gtivdlsala svsedpyeee lrritvglkt keeilgfleq lngewvnigk kkkvvnacdy ggylprgwrl mlyikrkgsn lllacrryis pdgqqfetck evstylrsll espsknqhyy lqsdnktlgq qpvianesll gnsdsmdset mqylesgrts sevfeeakav engneadrvk tslmqkddna dflngvednd ddmkkrdgnm enlatlsnse mtkslptttn elqqyfssqi nrvq (SEQ ID NO:16)

TABLE 8

Amino Acid Sequence of Gal4-VP16 Transcriptional Activator

```
aagctt ggatcc aaca atg aag ctc ctg tcc tcc atc gag cag gcc tgc gac atc tgc
                     M   K   L   L   S   S   I   E   Q   A   C   D   I   C cgc ctc aag aag ctc aag tgc tcc aag gag aag ccg aag tgc gcc aag tgt ctg aag aac
 R   L   K   K   L   K   C   S   K   E   K   P   K   C   A   K   C   L   K   N aac tgg gag tgt cgc tac tct ccc aaa acc aag cgc tcc ccg ctg acc cgc gcc cac ctc
 N   W   E   C   R   Y   S   P   K   T   K   R   S   P   L   T   R   A   H   L acc gaa gtg gag tcc cgc ctg gag cgc ctg gag cag ctc ttc ctc ctg atc ttc cct cga
 T   E   V   E   S   R   L   E   R   L   K   Q   L   F   L   L   I   F   P   R gag gac ctc gac atg atc ctg aaa atg gac tcc ctc cag gac atc aaa gcc ctg ctc acc
 E   D   L   D   M   I   L   K   M   D   S   L   Q   D   I   K   A   L   L   T ggc ctc ttc gtc cag gac aac gtg aac aaa gac gcc gtc acc gac cgc ctg gcc tcc gtg
 G   L   F   V   Q   D   N   V   N   K   D   A   V   T   D   R   L   A   S   V gag acc gac atg ccc ctc acc ctg cgc cag cac cgc atc agc gcg acc tcc tcc tcg gag
 E   T   D   M   P   L   T   L   R   Q   H   R   I   S   A   T   S   S   S   E gag agc agc aac aag ggc cag cgc cag ttg acc gtc tcg acg gcc ccc ccg acc gac gtc
 E   S   S   N   K   G   Q   R   Q   L   T   V   S   T   A   P   P   T   D   V agc ctg ggg gac gag ctc cac tta gac ggc gag gac gtg gcg atg gcg cat gcc gac gcg
 S   L   G   D   E   L   H   L   D   G   E   D   V   A   M   A   H   A   D   A cta gac gat ttc gat ctg gac atg ttg ggg gac ggg gat tcc ccg ggg ccg gga ttt acc
```

TABLE 8-continued

Amino Acid Sequence of Gal4-VP16 Transcriptional Activator

```
 L   D   D   F   D   L   D   M   L   G   D   G   D   S   P   G   P   G   F   T
ccc cac gac tcc gcc ccc tac ggc gct ctg gat atg gcc gac ttc gag ttt gag cag atg
 P   H   D   S   A   P   Y   G   A   L   D   M   A   D   F   E   F   E   Q   M ttt acc gat gcc ctt gga att gac gag    (SEQ ID NO:17)
tac ggt ggg tagatct
 F   T   D   A   L  -                  (SEQ ID NO:18)
   G   I   D   E   Y   G   G   *
```

TABLE 9

Amino Acid Sequence of FIE-15G-ESA1 Polypeptide

MSKITLGNESIVGSLTPSNKKSYKVTNRIQEGKKPLYAVVFNFLDARFFDVFVTAGGNRITLYNCLGDGAISALQSYADEDKEESFYTVSWACGVNGNPYVA

AGGVKGIIRVIDVNSETIHKSLVGHGDSVNEIRTQPLKPQLVITASKDESVRLWNVETGICILIFAGAGGHRYEVLSVDFHPSDIYRFASCGMDTTIKIWSM

KEFWTYVEKSFTWTDDPSKFPTKFVQFPVFTASIHTNYVDCNRWFGDFILSKSVDNEILLWEPQLKENSPGEGASDVLLRYPVPMCDIWFIKFSCDLHLSSV

AIGNQEGKVYVWDLKSCPPVLITKLSHNQSKSVIRQTAMSVDGSTILACCEDGTIWRWDVITKGSPGGGGGGGGGGGGGGGMRTHIEGHEELDAASLREHEE

FTKVKNISTIELGKYEIETWYFSPFPPEYNDCVKLFFCEFCLNFMKRKEQLQRHMRKCDLKHPPGDEIYRSGTLSMFEVDGKKNKVYAQNLCYLAKLFLDHK

TLYYDVDLFLFYVLCECDDRGCHMVGYFSKEKHSEEAYNLACILTLPSYQRKGYGKFLIAFSYELSKKEGKVGTPXKTLVGSRLTKLQRLLDSCSIRNLEKT (SEQ ID NO:19)

TABLE 10

Nucleotide Sequence of FIE-15 G-ESA1 cggagtactgtcctccgagcggagtactgtcctccgagcggagtactgtcctccgagcggagtactgtcctccgagcggagac tctagaacgattatttaggtgataagagtggacaatgatcgttgacacgtggacggtccacaaattctagttttgcctataagtatcaaagctgaatgtgta agttggatccaacaccagttgttgttgcatgagagacttgtgagcttagattagtgtgcgagagtcagacagagagagagatttcgaatatcgaatgtcgaa gataaccttagggaacgagtcaatagttgggtctttgactccatcgaataagaaatcgtacaaagtgacgaataggattcaggaagggaagaaacctttgta tgctgttgttttcaacttccttgatgctcgtttcttcgatgtcttcgttaccgctggtggaaatcggattactctgtacaattgtctcggagatggtgccat atcagcattgcaatcctatgctgatgaagataaggaagagtcgttttacacggtaagtttgggcgtgtggcgttaatgggaacccatatgttgcggctggagg agtaaaaggtataatccgagtcattgacgtcaacagtgaaacgattcataagagtcttgtgggtcatggagattcagtgaacgaaatcaggacacaaccttt aaaacctcaacttgtgattactgctagcaaggatgaatctgttcgtttgtggaatgttgaaactgggatatgtattttgatatttgctggagctggaggtca tcgctatgaagttctaagtgtggattttcatccgtctgatatttaccgctttgctagttgtggtatggacaccactattaaaatatggtcaatgaaagagtt ttggacgtacgtcgagaagtcattcacatggactgatgatccatcaaaattccccacaaaatttgtccaattccctgtatttacagcttccattcatacaaa ttatgtagattgtaaccgttggtttggtgattttatcctctcaaagagtgtggacaacgagatcctgttgtgggaaccacaactgaaagagaattctcctgg cgagggagcttcagatgttctattaagatacccggttccaatgtgtgatatttggtttatcaagttttcttgtgacctccatttaagttctgttgcgatagg taatcaggaaggaaaggtttatgtctgggatttgaaaagttgccctcctgttttgattacaaagttatcacacaatcaatcaaagtctgtaatcaggcaaac agccatgtctgtcgatggaagcacgattcttgcttgctgcgaggacgggactatatggcgctgggacgtgattaccaagggatccccggaggtggaggtgg aggtggaggtggaggtggaggtggaatgaggacacatatagagggtcatgaagagctggatgcagcaagtttgcgtgaacatgaagagttcacgaa agtgaagaacatatcaacaattgagcttggaaaatatgagattgagcttggtacttctcccttttccgccagaatacaatgactgtgtgaagctcttttt ttgtgagttttgcctgaacttcatgaaacgcaaagagcagcttcaaaggcatatgagraagtgtgacctgaagcacccacctggtgatgaaatttaccgaag tggtaccttgtcaatgtttgaggtagatggcaaaaagaacaaggtttatgcacagaatctctgctacctggcaaagttatttcttgaccacaaaactctta ctacgatgttgatttgtttctattctacgttcttttgcgaatgtgatgaccgaggatgccacatggtttgggtacttttcaaaggagaagcattcggaagaagc atacaacttagcttgcattctaaccctgccttcatatcaaagaaaggctatggaaagttcttaatagccttttcctatgaactgtcaaagaaagagggaaa

TABLE 10-continued

Nucleotide Sequence of FIE-15 G-ESA1 agttgggacaccggraaagacccttgtcggatctaggcttactaagctacagaggttattggactcgtgttctattagaaatcttgaaaaaacataactcga gggggggcccgctagagtcctgctttaatgagatatgcgagacgcctatgatcgcatgatatttgctttcaattctgttgtgcacgttgtaaaaaacctgag catgtgtagctcagatccttaccgccggtttcggttcattctaatgaatatatcacccgttactatcgtatttttatgaataatattctccgttcaatttac tgattgtaccctactacttatatgtacaatattaaaatgaaaacaatatattgtgctgaataggtttatagcgacatctatgatagagcgccacaataacaa acaattgcgttttattattacaaatccaattttaaaaaaagcggcagaaccggtcaaacctaaaagactgattacataaatcttattcaaatttcaaaaggc cccaggggctagtatctacgacacaccgagcggcgaactaataacgttcactgaagggaactccggttcccgccggcgcgcatgggtgagattccttgaag ttgagtattggccgtccgctctaccgaaagttacgggcaccattcaacccggtccagcacggcggccgggtaaccgacttgctgccccgagaattatgcagc attttttttggtgtatgtgggccccaaatgaagtgcaggtcaaaccttgacagtgacgcaaatcgttgggcggtccagggcgaattttgcgacaacatgtcga ggctcagcag (SEQ ID NO:20)

TABLE 11

Amino Acid Sequence of MEA-15G-ESA1 Polypeptide

MEKENHEDDGEGLPPELNQIKEQIEKERFLHIKRKFELRYIPSVATHASHHQSFDLNQPAAEDDNGGDNKSLLSRMQNPLRHFSASSDYNSYEDQGYVLDEDQ

DYALEEDVPLFLDEDVPLLPSVKLPIVEKLPRSITWVFTKSSQLMAESDSVIGKRQIYYLNGEALELSSEEDEEDEEEDEEEIKKEKCEFSEDVDRFIWTVGQ

DYGLDDLVVRRALAKYLEVDVSDILERYNELKLKNDGTAGEASDLTSKTITTAFQDFADRRHCRRCMIFDCHMHEKYEPESRSSEDKSSLFEDEDRQPCSEHC

YLKVRSVTEADHVMDNDNSISNKIVVSDPNNTMWTPVEKDLYLKGIEIFGRNSCDVALNILRGLKTCLEIYNYMREQDQCTMSLDLNKTTQRHNQVTKKVSRK

SSRSVRKKSRLRKYARYPPALKKTTSGEAKFYKHYTPCTCKSKCGQQCPCLTHENCCERYCGCSKDCNNRFGGCNCAIGQCTNRQCPCFAANRECDPDLCRSC

PLSCGDGTLGETPVQIQCKNMQFLLQTNKKILIGKSDVHGWGAFTWDSLKKNEYLGEYTGELITHDEANERGRIEDRIGSSYLFTLNDQLEIDARRKGNEFKF

LNHSARPNCYAKLMIVRGDQRIGLFAERAIEEGEELFFDYCYGPEHADWSRGREPRKTGASKRSKEARPARGSPGGGGGGGGGGGGGGGMRTHIEGHEELDAA

SLREHEEFTKVKNISTIELGKYEIETWYFSPFPPEYNDCVKLFFCEFCLNFMKRKEQKQRGNRJCDKJGOOGDEUTRSGTKSNFEVDGJJBJVTAQBKCTKAJ

KFKDGJTKTTDVDKFKFTVKCECDDRGCGNVGTFSJEJGSEEATBKACILTLPSYQRKGYGKFLIAFSYELSKKEGKVGTPXKTLVGSRLTKLQRLLDSCSIR

NLEKT (SEQ ID NO:21)

TABLE 12

Nucleotide Sequence of MEA-15G-ESA1 atggagaaggaaaaccatgaggacgatggtgagggtttgccacccgaactaaatcagataaaagagcaaatcgaaaaggagagatttctgcatatcaagagaa aattcgagctgagatacattccaagtgtggctactcatgcttcacaccatcaatcgtttgacttaaaccagcccgctgcagaggatgataatggaggagacaa caaatcacttttgtcgagaatgcaaaaccacttcgtcattcagtggcctcatctgattataattcttacgaagatcaaggttatgttcttgatgaggatcaa gattatgctcttgaagaagatgtaccattatttcttgatgaagatgtaccattattaccaagtgtcaagcttccaattgttgagaagctaccacgatccatta catgggtcttcaccaaaagtagccagctgatggctgaaagtgattctgtgattggtaagagacaaatctattagaagatgtagaccgatttatatggacggtt gggcaggactatggtttggatgatctggtcgtgcggcgtgctctcgccaagtacctcgaagtggatgtttgaatggtgaggcactagaattgagcagtgaaga agatgaggaagatgaagaagaagatgaggaagaaatcaagaaagaaaaatgcgaattttcttttccaggattttgctgatagacgtcattgccgtcgttgcat gatattcgattgtcatatgcatgagaagtatgagcccgagtctagatccagcgaagacaaatctagtttgtttgaggatgaagatagacaaccatgcagtgag cattgttacctcaaggtcaggagtgtgacagaagctgatcatgtgatggataatgataactctatatcaaacaagattgtggtctcagatccaaacaacacta tgtggacgcctgtagagaaggatctttacttgaaaggaattgagatatttgggagaaacagttgtgatgttgcattaaacatacttcggggcttaagacgtg cctagagatttacaattacatgcgcgaacaagatcaatgtactatgtcattagaccttaacaaaactacacaaagacacaatcaggttaccccccccgtatct

TABLE 12-continued

Nucleotide Sequence of MEA-15G-ESA1 cgaaaaagtagtaggtcggtccgcaaaaaatcgagactccgaaaatatgctcgttatccgcctgctttaaagaaaacaactagtggagaagctaagttttata agcactacacaccatgcacttgcaagtcaaaatgtggacagcaatgcccttgtttaactcacgaaaattgctgcgagaaatattgcgggtgctcaaaggattg caacaatcgctttggaggatgtaattgtgcaattggccaatgcacaaatcgacaatgtccttgttttgctgctaatcgtgaatgcgatccagatctttgtcgg agttgtcctcttagctgtggagatggcactcttggtgagacaccagtgcaaatccaatgcaagaacatgcaattcctccttcaaaccaataaaaagattctca ttggaaagtctgatgttcatggatggggtgcatttacatgggactctcttaaaaagaatgagtatctcggagaatatactggagaactgatcactcatgatga agctaatgagcgtgggagaatagaagatcggattggttcttcctacctctttaccttgaatgatcagctcgaaatcgatgctcgccgtaaaggaaacgagttc aaatttctcaatcactcagcaagacctaactgctacgccaagttgatgattgtgagaggagatcagaggattggtctatttgcggagagagcaatcgaagaag gtgaggagcttttcttcgactactgctatggaccagaacatgcggattggtcgcgtggtcgagaacctagaaagactggtgcttctaaaaggtctaaggaagc ccgtccagctcgtggatcccccggaggtggaggtggaggtggaggtggaggtggaggtggaggtggaatgaggacacatatagagggtcatgaagagctggat gcagcaagtttgcgtgaacatgaagagttcacgaaagtgaagaacatatcaacaattgagcttggaaaatatgagattgagacttggtacttctccccttttc cgccagaatacaatgactgtgtgaagctcttttttttgtgagttttgcctgaacttcatgaaacgcaaagagcagcttcaaaggcatatgagraagtgtgacct gaagcacccacctggtgatgaaatttaccgaagtggtaccttgtcaatgtttgaggtagatggcaaaaagaacaaggtttatgcacagaatctctgctacctg gcaaagttatttcttgaccacaaaactctttactacgatgttgatttgtttctattctacgttcttttgcgaatgtgatgaccgaggatgccacatggttgggt acttttcaaaggagaagcattcggaagaagcatacaacttagcttgcattctaaccctgccttcatatcaaagaaaaggctatggaaagttcttaatagcctt ttcctatgaactgtcaaagaaagagggaaaagttgggacaccggraaagacccttgtcggatctaggcttactaagctacagaggttattggactcgtgttct attagaaatcttgaaaaacataa (SEQ ID NO:22)

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid construct encoding a chimeric polypeptide comprising
the amino acid sequence set forth in SEQ ID NO:19.

2. An isolated nucleic acid construct encoding a chimeric polypeptide comprising
the amino acid sequence set forth in SEQ ID NO:21.

3. The isolated nucleic acid of claim 1 or claim 2, wherein said isolated nucleic acid construct further comprises a regulatory element to facilitate expression of said encoded chimeric polypeptide.

4. The isolated nucleic acid of claim 3, wherein said regulatory element is a cell type specific or tissue-specific promoter.

* * * * *

UNITED STATES PATENT AND TRADEMARK OFFICE
CERTIFICATE OF CORRECTION

PATENT NO. : 7,264,964 B2
APPLICATION NO. : 10/177478
DATED : September 4, 2007
INVENTOR(S) : David VanDinh Dang It is certified that error appears in the above-identified patent and that said Letters Patent is hereby corrected as shown below:

Title Page (Page 2), References Cited, Other Publications, GenBank A43 reference, please delete "A43" and insert --D50643-- therefor;

Title Page (Page 2), References Cited, Other Publications, http://www.plantsci.cam.ac.uk/ reference, please delete "Index/Catalogue" and insert --IndexCatalogue.html-- therefor;

Title Page (Page 2), References Cited, Other Publications, Chen and Foolad reference, please delete "nucellar" and insert --nuclear-- therefor;

Title Page (Page 3), References Cited, Other Publications, Granger et al. reference, please delete "homologuge" and insert --homologue-- therefor;

Title Page (Page 3), References Cited, Other Publications, Green et al. reference, please delete "fo" and insert --of-- therefor;

Title Page (Page 3), References Cited, Other Publications, Hager et al. reference, please delete "nulcear" and insert --nuclear-- therefor;

Title Page (Page 3), References Cited, Other Publications, Ingram et al. reference, please delete "Chromodormain" and insert --Chromodomain-- therefor;

Title Page (Page 3), References Cited, Other Publications, Josefsson et al. reference, please delete "Brassice" and insert --Brassica-- therefor;

Title Page (Page 3), References Cited, Other Publications, Kent et al. reference, please delete "Isw1p" and insert --IswLp-- therefor;

Title Page (Page 3), References Cited, Other Publications, Kerstetter et al. reference, please delete "Homebox" and insert --Homeobox-- therefor;

Title Page (Page 3), References Cited, Other Publications, Kumagai et al. reference, please delete "carotenid" and insert --carotenoid-- therefor;

UNITED STATES PATENT AND TRADEMARK OFFICE
CERTIFICATE OF CORRECTION

PATENT NO. : 7,264,964 B2
APPLICATION NO. : 10/177478
DATED : September 4, 2007
INVENTOR(S) : David VanDinh Dang It is certified that error appears in the above-identified patent and that said Letters Patent is hereby corrected as shown below:

Title Page (Page 4), References Cited, Other Publications, Tie et al. reference, please delete "313-321" and insert --3483-3496-- therefor;

Title Page (Page 4), References Cited, Other Publications, Vignalia et al. reference, please delete "Vignalia" and insert --Vignali-- therefor;

Title Page (Page 5), References Cited, Other Publications, Weterings et al. reference, please delete "Locailzation" and insert --Localization-- therefor.

Signed and Sealed this

Eighteenth Day of November, 2008

JON W. DUDAS
*Director of the United States Patent and Trademark Office*

SEQUENCE LISTING

```
<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tttttttttt tttttttv                                              19

<210> SEQ ID NO 2
<211> LENGTH: 371
<212> TYPE: PRT
<213> ORGANISM: Arabidopsis thaliana
<220> FEATURE:
<221> NAME/KEY: VARIANT
<222> LOCATION: 223 and 345
<223> OTHER INFORMATION: Xaa = Any Amino Acid

<400> SEQUENCE: 2

Met Gly Ser Ser Ala Asn Thr Glu Thr Asn Gly Asn Ala Pro Pro Pro
```

|   | 1 |   |   |   | 5 |   |   |   |   | 10 |   |   |   |   | 15 |
|---|---|---|---|---|---|---|---|---|---|----|---|---|---|---|----|

Ser Ser Asn Gln Lys Pro Pro Ala Thr Asn Gly Val Asp Gly Ser His
          20               25               30

Pro Pro Pro Pro Leu Thr Pro Asp Gln Ala Ile Ile Glu Ser Asp
        35              40              45

Pro Ser Lys Lys Arg Lys Met Gly Met Leu Pro Leu Glu Val Gly Thr
     50              55              60

Arg Val Met Cys Arg Trp Arg Asp Gly Lys His His Pro Val Lys Val
65               70              75             80

Ile Glu Arg Arg Arg Ile His Asn Gly Gly Gln Asn Asp Tyr Glu Tyr
             85              90             95

Tyr Val His Tyr Thr Glu Phe Asn Arg Arg Leu Asp Glu Trp Thr Gln
         100              105            110

Leu Asp Gln Leu Asp Leu Asp Ser Val Glu Cys Ala Val Asp Glu Lys
        115              120            125

Leu Glu Asp Lys Val Thr Ser Leu Lys Met Thr Arg His Gln Lys Arg
130              135            140

Lys Ile Asp Glu Thr His Ile Glu Gly His Glu Glu Leu Asp Ala Ala
145              150            155            160

Ser Leu Arg Glu His Glu Glu Phe Thr Lys Val Lys Asn Ile Ser Thr
         165              170            175

Ile Glu Leu Gly Lys Tyr Glu Ile Glu Thr Trp Tyr Phe Ser Pro Phe
         180              185            190

Pro Pro Glu Tyr Asn Asp Cys Val Lys Leu Phe Phe Cys Glu Phe Cys
         195              200            205

Leu Asn Phe Met Lys Arg Lys Glu Gln Leu Gln Arg His Met Xaa Lys
     210              215              220

Cys Asp Leu Lys His Pro Pro Gly Asp Glu Ile Tyr Arg Ser Gly Thr
225              230            235            240

Leu Ser Met Phe Glu Val Asp Gly Lys Lys Asn Lys Val Tyr Ala Gln
         245              250            255

Asn Leu Cys Tyr Leu Ala Lys Leu Phe Leu Asp His Lys Thr Leu Tyr
     260              265              270

Tyr Asp Val Asp Leu Phe Leu Phe Tyr Val Leu Cys Glu Cys Asp Asp
         275              280            285

Arg Gly Cys His Met Val Gly Tyr Phe Ser Lys Glu Lys His Ser Glu
         290              295            300

Glu Ala Tyr Asn Leu Ala Cys Ile Leu Thr Leu Pro Ser Tyr Gln Arg
305              310            315            320

Lys Gly Tyr Gly Lys Phe Leu Ile Ala Phe Ser Tyr Glu Leu Ser Lys
         325              330            335

Lys Glu Gly Lys Val Gly Thr Pro Xaa Lys Thr Leu Val Gly Ser Arg
         340              345            350

Leu Thr Lys Leu Gln Arg Leu Leu Asp Ser Cys Ser Ile Arg Asn Leu
         355              360            365

Glu Lys Thr
     370

<210> SEQ ID NO 3
<211> LENGTH: 586
<212> TYPE: PRT
<213> ORGANISM: Zea mays

<400> SEQUENCE: 3

-continued

```
Met Asp Ser His Ser His Leu Asn Ala Ala Asn Arg Ser Arg Ser
 1               5                  10                 15

Ser Gln Thr Pro Ser Pro Ser His Ser Ala Ser Ala Ser Val Thr Ser
             20                  25                  30

Ser Leu His Lys Arg Lys Leu Ala Ala Thr Thr Ala Ala Asn Ala Ala
         35                  40                  45

Ala Ser Glu Asp His Ala Pro Pro Ser Ser Phe Pro Pro Ser Ser
 50                  55                  60

Phe Ser Ala Asp Thr Arg Asp Gly Ala Leu Thr Ser Asn Asp Glu Leu
 65              70                  75                  80

Glu Ser Ile Ser Ala Arg Gly Ala Asp Thr Asp Ser Asp Pro Asp Glu
                 85                  90                  95

Ser Glu Asp Ile Val Val Asp Asp Glu Asp Glu Phe Ala Pro Glu
             100                 105                 110

Gln Asp Gln Asp Ser Ser Ile Arg Thr Phe Thr Ala Ala Arg Leu Asp
             115                 120                 125

Ser Ser Gly Val Asn Gly Ser Ser Arg Asn Thr Lys Leu Lys Thr
130                 135                 140

Glu Ser Ser Thr Val Lys Leu Glu Ser Ser Asp Gly Lys Asp Gly
145                 150                 155                 160

Gly Ser Ser Val Val Gly Thr Gly Val Ser Gly Thr Val Gly Gly Ser
                 165                 170                 175

Ser Ile Ser Gly Leu Val Pro Lys Asp Glu Ser Val Lys Val Leu Ala
             180                 185                 190

Glu Asn Phe Gln Thr Ser Gly Ala Tyr Ile Ala Arg Glu Glu Ala Leu
         195                 200                 205

Lys Arg Glu Glu Gln Ala Gly Arg Leu Lys Phe Val Cys Tyr Ser Asn
210                 215                 220

Asp Ser Ile Asp Glu His Met Met Cys Leu Ile Gly Leu Lys Asn Ile
225                 230                 235                 240

Phe Ala Arg Gln Leu Pro Asn Met Pro Lys Glu Tyr Ile Val Arg Leu
             245                 250                 255

Leu Met Asp Arg Lys His Lys Ser Val Met Val Leu Arg Gly Asn Leu
         260                 265                 270

Val Val Gly Gly Ile Thr Tyr Arg Pro Tyr His Ser Gln Lys Phe Gly
     275                 280                 285

Glu Ile Ala Phe Cys Ala Ile Thr Ala Asp Glu Gln Val Lys Gly Tyr
290                 295                 300

Gly Thr Arg Leu Met Asn His Leu Lys Gln His Ala Arg Asp Val Asp
305                 310                 315                 320

Gly Leu Thr His Phe Leu Thr Tyr Ala Asp Asn Asn Ala Val Gly Tyr
                 325                 330                 335

Phe Val Lys Gln Glu Ile Pro Gln Ser Phe Thr Ser Lys Ser Ser Val
             340                 345                 350

Ser Thr Leu Ser Tyr Gln Gly Phe Thr Lys Glu Ile Tyr Leu Glu Lys
         355                 360                 365

Asp Val Trp His Gly Phe Ile Lys Asp Tyr Asp Gly Gly Leu Leu Met
     370                 375                 380

Glu Cys Lys Ile Asp Pro Lys Leu Pro Tyr Thr Asp Leu Ser Ser Met
385                 390                 395                 400

Ile Arg Gln Gln Arg Lys Ala Ile Asp Glu Arg Ile Arg Glu Leu Ser
                 405                 410                 415

Asn Cys Gln Asn Val Tyr Pro Lys Ile Glu Phe Leu Lys Asn Glu Ala
```

```
                420                 425                 430
Gly Ile Pro Arg Lys Ile Ile Lys Val Glu Glu Ile Arg Gly Leu Arg
            435                 440                 445
Glu Ala Gly Trp Thr Pro Asp Gln Trp Gly His Thr Arg Phe Lys Leu
        450                 455                 460
Phe Asn Gly Ser Ala Asp Met Val Thr Asn Gln Lys Gln Leu Asn Ala
465                 470                 475                 480
Leu Met Arg Ala Leu Leu Lys Thr Met Gln Asp His Ala Asp Ala Trp
                485                 490                 495
Pro Phe Lys Glu Pro Val Asp Ser Arg Asp Val Pro Asp Tyr Tyr Asp
            500                 505                 510
Ile Ile Lys Asp Pro Ile Asp Leu Lys Val Ile Ala Lys Arg Val Glu
        515                 520                 525
Ser Glu Gln Tyr Tyr Val Thr Leu Asp Met Phe Val Ala Asp Ala Arg
    530                 535                 540
Arg Met Phe Asn Asn Cys Arg Thr Tyr Asn Ser Pro Asp Thr Ile Tyr
545                 550                 555                 560
Tyr Lys Cys Ala Thr Arg Leu Glu Thr His Phe His Ser Lys Val Gln
                565                 570                 575
Ala Gly Leu Gln Ser Gly Ala Lys Ser Gln
            580                 585

<210> SEQ ID NO 4
<211> LENGTH: 386
<212> TYPE: PRT
<213> ORGANISM: Arabidopsis thaliana

<400> SEQUENCE: 4

Met Ser Val His Val Lys Glu Glu Pro Val Leu Val Pro Asn Cys Asp
1               5                  10                  15
Val Glu Asn Thr Glu Leu Ala Val Phe Asn Gly Asn Gly Glu Ser Glu
            20                  25                  30
Leu Glu Asn Phe Gly Thr Cys Val Asp Glu Ile Thr Asp Arg Val Asn
        35                  40                  45
Gln Leu Glu Gln Lys Val Val Glu Val Glu His Phe Tyr Ser Thr Lys
    50                  55                  60
Asp Gly Ala Ala Gln Thr Asn Thr Ser Lys Ser Asn Ser Gly Gly Lys
65                  70                  75                  80
Lys Ile Ala Ile Ser Gln Pro Asn Asn Ser Lys Gly Asn Ser Ala Gly
                85                  90                  95
Lys Glu Lys Ser Lys Gly Lys His Val Ser Ser Pro Asp Leu Met Arg
            100                 105                 110
Gln Phe Ala Thr Met Phe Arg Gln Ile Ala Gln His Lys Trp Ala Trp
        115                 120                 125
Pro Phe Leu Glu Pro Val Asp Val Lys Gly Leu Gly Leu His Asp Tyr
    130                 135                 140
Tyr Lys Val Ile Glu Lys Pro Met Asp Leu Gly Thr Ile Lys Lys Lys
145                 150                 155                 160
Met Glu Ser Ser Glu Tyr Ser Asn Val Arg Glu Ile Tyr Ala Asp Val
                165                 170                 175
Arg Leu Val Phe Lys Asn Ala Met Arg Tyr Asn Glu Glu Lys Glu Asp
            180                 185                 190
Val Tyr Val Met Ala Glu Ser Leu Leu Glu Lys Phe Glu Glu Lys Trp
        195                 200                 205
```

-continued

```
Leu Leu Ile Met Pro Lys Leu Glu Glu Lys Gln Val Asp
    210                 215                 220

Glu Glu Ala Glu Lys His Ala Asn Lys Gln Leu Thr Met Glu Ala Ala
225                 230                 235                 240

Gln Ala Glu Met Ala Arg Asp Leu Ser Asn Glu Leu Tyr Glu Ile Asp
                245                 250                 255

Leu Gln Leu Glu Lys Leu Arg Glu Ser Val Val Gln Arg Cys Arg Lys
            260                 265                 270

Leu Ser Thr Gln Glu Lys Lys Gly Leu Ser Ala Ala Leu Gly Arg Leu
        275                 280                 285

Ser Pro Glu Asp Leu Ser Lys Ala Leu Lys Met Val Ser Glu Ser Asn
290                 295                 300

Pro Ser Phe Pro Ala Gly Ala Pro Glu Val Glu Leu Asp Ile Asp Val
305                 310                 315                 320

Gln Thr Asp Val Thr Leu Trp Arg Leu Lys Val Phe Val Gln Glu Ala
                325                 330                 335

Leu Lys Ala Ala Asn Lys Ser Ser Gly Gly Thr Asn Ala Gln Asn Asn
            340                 345                 350

Asn Asn Thr Gly Thr Gly Glu Ile Asn Lys Asn Asn Ala Lys Arg Arg
        355                 360                 365

Arg Glu Ile Ser Asp Ala Ile Asn Lys Ala Ser Ile Lys Arg Ala Lys
370                 375                 380

Lys Ala
385
```

<210> SEQ ID NO 5
<211> LENGTH: 689
<212> TYPE: PRT
<213> ORGANISM: Arabidopsis thaliana

<400> SEQUENCE: 5

```
Met Glu Lys Glu Asn His Glu Asp Asp Gly Glu Gly Leu Pro Pro Glu
1               5                   10                  15

Leu Asn Gln Ile Lys Glu Gln Ile Glu Lys Glu Arg Phe Leu His Ile
            20                  25                  30

Lys Arg Lys Phe Glu Leu Arg Tyr Ile Pro Ser Val Ala Thr His Ala
        35                  40                  45

Ser His His Gln Ser Phe Asp Leu Asn Gln Pro Ala Ala Glu Asp Asp
    50                  55                  60

Asn Gly Gly Asp Asn Lys Ser Leu Leu Ser Arg Met Gln Asn Pro Leu
65                  70                  75                  80

Arg His Phe Ser Ala Ser Ser Asp Tyr Asn Ser Tyr Glu Asp Gln Gly
                85                  90                  95

Tyr Val Leu Asp Glu Asp Gln Asp Tyr Ala Leu Glu Glu Asp Val Pro
            100                 105                 110

Leu Phe Leu Asp Glu Asp Val Pro Leu Leu Pro Ser Val Lys Leu Pro
        115                 120                 125

Ile Val Glu Lys Leu Pro Arg Ser Ile Thr Trp Val Phe Thr Lys Ser
    130                 135                 140

Ser Gln Leu Met Ala Glu Ser Asp Ser Val Ile Gly Lys Arg Gln Ile
145                 150                 155                 160

Tyr Tyr Leu Asn Gly Glu Ala Leu Glu Leu Ser Ser Glu Glu Asp Glu
                165                 170                 175

Glu Asp Glu Glu Glu Asp Glu Glu Glu Ile Lys Lys Glu Lys Cys Glu
            180                 185                 190
```

```
Phe Ser Glu Asp Val Asp Arg Phe Ile Trp Thr Val Gly Gln Asp Tyr
        195                 200                 205

Gly Leu Asp Asp Leu Val Val Arg Arg Ala Leu Ala Lys Tyr Leu Glu
        210                 215                 220

Val Asp Val Ser Asp Ile Leu Glu Arg Tyr Asn Glu Leu Lys Leu Lys
225                 230                 235                 240

Asn Asp Gly Thr Ala Gly Glu Ala Ser Asp Leu Thr Ser Lys Thr Ile
            245                 250                 255

Thr Thr Ala Phe Gln Asp Phe Ala Asp Arg Arg His Cys Arg Arg Cys
            260                 265                 270

Met Ile Phe Asp Cys His Met His Glu Lys Tyr Glu Pro Glu Ser Arg
        275                 280                 285

Ser Ser Glu Asp Lys Ser Ser Leu Phe Glu Asp Glu Asp Arg Gln Pro
        290                 295                 300

Cys Ser Glu His Cys Tyr Leu Lys Val Arg Ser Val Thr Glu Ala Asp
305                 310                 315                 320

His Val Met Asp Asn Asp Asn Ser Ile Ser Asn Lys Ile Val Val Ser
            325                 330                 335

Asp Pro Asn Asn Thr Met Trp Thr Pro Val Glu Lys Asp Leu Tyr Leu
            340                 345                 350

Lys Gly Ile Glu Ile Phe Gly Arg Asn Ser Cys Asp Val Ala Leu Asn
            355                 360                 365

Ile Leu Arg Gly Leu Lys Thr Cys Leu Glu Ile Tyr Asn Tyr Met Arg
        370                 375                 380

Glu Gln Asp Gln Cys Thr Met Ser Leu Asp Leu Asn Lys Thr Thr Gln
385                 390                 395                 400

Arg His Asn Gln Val Thr Lys Lys Val Ser Arg Lys Ser Ser Arg Ser
            405                 410                 415

Val Arg Lys Lys Ser Arg Leu Arg Lys Tyr Ala Arg Tyr Pro Pro Ala
            420                 425                 430

Leu Lys Lys Thr Thr Ser Gly Glu Ala Lys Phe Tyr Lys His Tyr Thr
        435                 440                 445

Pro Cys Thr Cys Lys Ser Lys Cys Gly Gln Gln Cys Pro Cys Leu Thr
        450                 455                 460

His Glu Asn Cys Cys Glu Lys Tyr Cys Gly Cys Ser Lys Asp Cys Asn
465                 470                 475                 480

Asn Arg Phe Gly Gly Cys Asn Cys Ala Ile Gly Gln Cys Thr Asn Arg
            485                 490                 495

Gln Cys Pro Cys Phe Ala Ala Asn Arg Glu Cys Asp Pro Asp Leu Cys
            500                 505                 510

Arg Ser Cys Pro Leu Ser Cys Gly Asp Gly Thr Leu Gly Glu Thr Pro
        515                 520                 525

Val Gln Ile Gln Cys Lys Asn Met Gln Phe Leu Leu Gln Thr Asn Lys
        530                 535                 540

Lys Ile Leu Ile Gly Lys Ser Asp Val His Gly Trp Gly Ala Phe Thr
545                 550                 555                 560

Trp Asp Ser Leu Lys Lys Asn Glu Tyr Leu Gly Glu Tyr Thr Gly Glu
            565                 570                 575

Leu Ile Thr His Asp Glu Ala Asn Glu Arg Gly Arg Ile Glu Asp Arg
            580                 585                 590

Ile Gly Ser Ser Tyr Leu Phe Thr Leu Asn Asp Gln Leu Glu Ile Asp
            595                 600                 605
```

```
Ala Arg Arg Lys Gly Asn Glu Phe Lys Phe Leu Asn His Ser Ala Arg
    610                 615                 620

Pro Asn Cys Tyr Ala Lys Leu Met Ile Val Arg Gly Asp Gln Arg Ile
625                 630                 635                 640

Gly Leu Phe Ala Glu Arg Ala Ile Glu Glu Gly Glu Glu Leu Phe Phe
                645                 650                 655

Asp Tyr Cys Tyr Gly Pro Glu His Ala Asp Trp Ser Arg Gly Arg Glu
            660                 665                 670

Pro Arg Lys Thr Gly Ala Ser Lys Arg Ser Lys Glu Ala Arg Pro Ala
        675                 680                 685

Arg

<210> SEQ ID NO 6
<211> LENGTH: 692
<212> TYPE: PRT
<213> ORGANISM: Arabidopsis thaliana

<400> SEQUENCE: 6

Met Thr Leu Lys Ala Glu Val Val Glu Asn Phe Ser Cys Pro Phe Cys
1               5                   10                  15

Leu Ile Pro Cys Gly Gly His Glu Gly Leu Gln Leu His Leu Lys Ser
                20                  25                  30

Ser His Asp Ala Phe Lys Phe Glu Phe Tyr Arg Ala Glu Lys Asp His
            35                  40                  45

Gly Pro Glu Val Asp Val Ser Val Lys Ser Asp Thr Ile Lys Phe Gly
        50                  55                  60

Val Leu Lys Asp Asp Val Gly Asn Pro Gln Leu Ser Pro Leu Thr Phe
65                  70                  75                  80

Cys Ser Lys Asn Arg Asn Gln Arg Arg Gln Arg Asp Asp Ser Asn Asn
                85                  90                  95

Val Lys Lys Leu Asn Val Leu Leu Met Glu Leu Asp Leu Asp Asp Leu
                100                 105                 110

Pro Arg Gly Thr Glu Asn Asp Ser Thr His Val Asn Asp Asp Asn Val
            115                 120                 125

Ser Ser Pro Pro Arg Ala His Ser Ser Glu Lys Ile Ser Asp Ile Leu
130                 135                 140

Thr Thr Thr Gln Leu Ala Ile Ala Glu Ser Ser Glu Pro Lys Val Pro
145                 150                 155                 160

His Val Asn Asp Gly Asn Val Ser Ser Pro Arg Ala His Ser Ser
                165                 170                 175

Ala Glu Lys Asn Glu Ser Thr His Val Asn Asp Asp Asp Val Ser
            180                 185                 190

Ser Pro Pro Arg Ala His Ser Leu Glu Lys Asn Glu Ser Thr His Val
        195                 200                 205

Asn Glu Asp Asn Ile Ser Ser Pro Lys Ala His Ser Ser Lys Lys
210                 215                 220

Asn Glu Ser Thr His Met Asn Asp Glu Asp Val Ser Phe Pro Pro Arg
225                 230                 235                 240

Thr Arg Ser Ser Lys Glu Thr Ser Asp Ile Leu Thr Thr Thr Gln Pro
                245                 250                 255

Ala Ile Val Glu Pro Ser Glu Pro Lys Val Arg Arg Gly Ser Arg Arg
            260                 265                 270

Lys Gln Leu Tyr Ala Lys Arg Tyr Lys Ala Arg Glu Thr Gln Pro Ala
        275                 280                 285
```

```
Ile Ala Glu Ser Ser Glu Pro Lys Val His Val Asn Asp Glu Asn
    290                 295                 300

Val Ser Ser Pro Pro Glu Ala His Ser Leu Glu Lys Ala Ser Asp Ile
305                 310                 315                 320

Leu Thr Thr Thr Gln Pro Ala Ile Ala Glu Ser Ser Glu Pro Lys Val
                    325                 330                 335

Pro His Val Asn Asp Glu Asn Val Ser Ser Thr Pro Arg Ala His Ser
                340                 345                 350

Ser Lys Lys Asn Lys Ser Thr Arg Lys Asn Val Asp Asn Val Pro Ser
            355                 360                 365

Pro Pro Lys Thr Arg Ser Ser Lys Lys Thr Ser Asp Ile Leu Thr Thr
        370                 375                 380

Thr Gln Pro Thr Ile Ala Glu Ser Ser Glu Pro Lys Val Arg His Val
385                 390                 395                 400

Asn Asp Asp Asn Val Ser Ser Thr Pro Arg Ala His Ser Ser Lys Lys
                405                 410                 415

Asn Lys Ser Thr Arg Lys Asn Asp Asn Ile Pro Ser Pro Pro Lys
            420                 425                 430

Thr Arg Ser Ser Lys Lys Thr Ser Asn Ile Leu Thr Arg Thr Gln Pro
                435                 440                 445

Ala Ile Ala Glu Ser Glu Pro Lys Val Pro His Val Asn Asp Asp Lys
450                 455                 460

Val Ser Ser Thr Pro Arg Ala His Ser Lys Lys Asn Lys Ser Thr
465                 470                 475                 480

His Lys Lys Asp Asp Asn Ala Ser Leu Pro Pro Lys Thr Arg Ser Ser
                485                 490                 495

Lys Lys Thr Ser Asp Ile Leu Ala Thr Thr Gln Pro Ala Lys Ala Glu
            500                 505                 510

Pro Ser Glu Pro Lys Val Thr Arg Val Ser Arg Arg Lys Glu Leu His
        515                 520                 525

Ala Glu Arg Cys Glu Ala Lys Arg Leu Glu Arg Leu Lys Gly Arg Gln
530                 535                 540

Phe Tyr His Ser Gln Thr Met Gln Pro Met Thr Phe Glu Gln Val Met
545                 550                 555                 560

Ser Asn Glu Asp Ser Glu Asn Glu Thr Asp Asp Tyr Ala Leu Asp Ile
                565                 570                 575

Ser Glu Arg Leu Arg Leu Glu Arg Leu Val Gly Val Ser Lys Glu Glu
            580                 585                 590

Lys Arg Tyr Met Tyr Leu Trp Asn Ile Phe Val Arg Lys Gln Arg Val
        595                 600                 605

Ile Ala Asp Gly His Val Pro Trp Ala Cys Glu Glu Phe Ala Lys Leu
610                 615                 620

His Lys Glu Glu Met Lys Asn Ser Ser Phe Asp Trp Trp Arg
625                 630                 635                 640

Met Phe Arg Ile Lys Leu Trp Asn Asn Gly Leu Ile Cys Ala Lys Thr
                645                 650                 655

Phe His Lys Cys Thr Thr Ile Leu Leu Ser Asn Ser Asp Glu Ala Gly
            660                 665                 670

Gln Phe Thr Ser Gly Ser Ala Ala Asn Ala Asn Asn Gln Gln Ser Met
        675                 680                 685

Glu Val Asp Glu
690
```

<210> SEQ ID NO 7
<211> LENGTH: 369
<212> TYPE: PRT
<213> ORGANISM: Arabidopsis thaliana

<400> SEQUENCE: 7

```
Met Ser Lys Ile Thr Leu Gly Asn Glu Ser Ile Val Gly Ser Leu Thr
 1               5                  10                  15
Pro Ser Asn Lys Lys Ser Tyr Lys Val Thr Asn Arg Ile Gln Glu Gly
            20                  25                  30
Lys Lys Pro Leu Tyr Ala Val Val Phe Asn Phe Leu Asp Ala Arg Phe
        35                  40                  45
Phe Asp Val Phe Val Thr Ala Gly Gly Asn Arg Ile Thr Leu Tyr Asn
 50                  55                  60
Cys Leu Gly Asp Gly Ala Ile Ser Ala Leu Gln Ser Tyr Ala Asp Glu
 65                  70                  75                  80
Asp Lys Glu Glu Ser Phe Tyr Thr Val Ser Trp Ala Cys Gly Val Asn
                85                  90                  95
Gly Asn Pro Tyr Val Ala Ala Gly Val Lys Gly Ile Ile Arg Val
            100                 105                 110
Ile Asp Val Asn Ser Glu Thr Ile His Lys Ser Leu Val Gly His Gly
        115                 120                 125
Asp Ser Val Asn Glu Ile Arg Thr Gln Pro Leu Lys Pro Gln Leu Val
    130                 135                 140
Ile Thr Ala Ser Lys Asp Glu Ser Val Arg Leu Trp Asn Val Glu Thr
145                 150                 155                 160
Gly Ile Cys Ile Leu Ile Phe Ala Gly Ala Gly His Arg Tyr Glu
                165                 170                 175
Val Leu Ser Val Asp Phe His Pro Ser Asp Ile Tyr Arg Phe Ala Ser
            180                 185                 190
Cys Gly Met Asp Thr Thr Ile Lys Ile Trp Ser Met Lys Glu Phe Trp
        195                 200                 205
Thr Tyr Val Glu Lys Ser Phe Thr Trp Thr Asp Asp Pro Ser Lys Phe
210                 215                 220
Pro Thr Lys Phe Val Gln Phe Pro Val Phe Thr Ala Ser Ile His Thr
225                 230                 235                 240
Asn Tyr Val Asp Cys Asn Arg Trp Phe Gly Asp Phe Ile Leu Ser Lys
                245                 250                 255
Ser Val Asp Asn Glu Ile Leu Leu Trp Glu Pro Gln Leu Lys Glu Asn
            260                 265                 270
Ser Pro Gly Glu Gly Ala Ser Asp Val Leu Leu Arg Tyr Pro Val Pro
        275                 280                 285
Met Cys Asp Ile Trp Phe Ile Lys Phe Ser Cys Asp Leu His Leu Ser
    290                 295                 300
Ser Val Ala Ile Gly Asn Gln Glu Gly Lys Val Tyr Val Trp Asp Leu
305                 310                 315                 320
Lys Ser Cys Pro Pro Val Leu Ile Thr Lys Leu Ser His Asn Gln Ser
                325                 330                 335
Lys Ser Val Ile Arg Gln Thr Ala Met Ser Val Asp Gly Ser Thr Ile
            340                 345                 350
Leu Ala Cys Cys Glu Asp Gly Thr Ile Trp Arg Trp Asp Val Ile Thr
        355                 360                 365
Lys
```

```
<210> SEQ ID NO 8
<211> LENGTH: 411
<212> TYPE: PRT
<213> ORGANISM: Arabidopsis thaliana

<400> SEQUENCE: 8

Met Glu Ser Pro Ser Ile Ser Asp Ala Val Pro Leu His Ala Pro Glu
  1               5                  10                  15

Asp Ala Thr Ala Asp Phe Ser Gln Pro Gln Ser Pro Leu His Glu Val
             20                  25                  30

Asp Ser Phe Pro Val Thr Glu Ser Ser Asp Val Val Val Asn Val
         35                  40                  45

Ser Glu Ile Pro Asn Leu Ser Pro Ser Asp Asp Phe Asp His Glu
 50                  55                  60

Arg Asn Ser Gly Glu Asp Arg Asp Gln Asp His Gly Asn Pro Val
 65                  70                  75                  80

Glu Thr Asp Gly Val Val Pro Ile Asp Glu Leu Asn Gln Lys Ile
                 85                  90                  95

Ile Arg Gln Val Glu Tyr Tyr Phe Ser Asp Glu Asn Leu Pro Thr Asp
                100                 105                 110

Lys Phe Leu Leu Asn Ala Met Lys Arg Asn Lys Lys Gly Phe Val Pro
            115                 120                 125

Ile Ser Thr Ile Ala Thr Phe His Lys Met Lys Lys Leu Thr Arg Asp
        130                 135                 140

His Ala Leu Ile Val Ser Ala Leu Lys Glu Ser Ser Phe Leu Val Val
145                 150                 155                 160

Ser Ala Asp Glu Lys Lys Val Lys Arg Leu Ser Pro Leu Pro Glu Ile
                165                 170                 175

Arg Asp Pro Lys Ile Phe Thr Val Leu Val Glu Asn Leu Pro Glu Asp
            180                 185                 190

His Ser Asn Glu Asn Ile Arg Glu Ile Phe Gly Lys Ala Gly Ser Ile
        195                 200                 205

Lys Ser Val Ser Ile Cys Asp Pro Asn Ala Val Glu Glu Ser Glu Lys
    210                 215                 220

Gly Gly Lys Lys Glu Asn Phe Ile Arg Thr Arg Leu His Ala Phe Val
225                 230                 235                 240

Glu Tyr Glu Thr Val Glu Ala Ala Glu Lys Ala Ala Thr Leu Asn
                245                 250                 255

Asn Glu Gln Asp Trp Arg Asn Gly Leu Arg Val Lys Leu Leu Glu Gln
            260                 265                 270

Ala Ala Gly Lys Phe Ala Gln Arg Arg Pro Ala Arg Arg Glu Val Asp
        275                 280                 285

Lys Glu Lys Asp Thr Thr Gly Arg Val His Asp Gln Thr Gly Gly Glu
    290                 295                 300

Lys Asn Lys Lys Thr Arg Glu His Gln Asn His Arg Leu His His Ser
305                 310                 315                 320

Asp Asn Pro Ala Asp Asp Gly Gly Asn His Gln Lys Asp Lys Asn
                325                 330                 335

Gly Asn Lys Gly Arg Val Val Gly Gln Gly Arg Arg Gln Asn His Gln
            340                 345                 350

Gly Gly Asn Gly Ile Gly His Gly Thr Ala Ser Ser Ser Ser His Pro
        355                 360                 365

Asn Tyr His Pro Val Glu Val Ser Lys Arg Pro Pro Gly Pro Arg Met
    370                 375                 380
```

Pro Asp Gly Thr Arg Gly Phe Thr Met Gly Arg Gly Lys Ala Ile Pro
385                 390                 395                 400

Pro Pro Thr Ser Thr Gln Thr Ser His Glu Val
                405                 410

<210> SEQ ID NO 9
<211> LENGTH: 609
<212> TYPE: PRT
<213> ORGANISM: Arabidopsis thaliana

<400> SEQUENCE: 9

Met Asp Thr Pro Glu Lys Ser Glu Thr Gln Ile Gly Thr Pro Val Ser
1               5                   10                  15

Lys Leu Lys Val Glu Asp Ser Pro Val Phe Ser Tyr Ile Cys Asn Leu
                20                  25                  30

Ser Pro Ile Lys Thr Ile Lys Pro Ile Pro Ile Thr Cys Pro Leu Ser
            35                  40                  45

Ser Leu Asn Tyr Ala Ser Pro Pro Ser Val Phe Thr Ser Pro His Ala
        50                  55                  60

Val Ser His Lys Glu Ser Arg Phe Arg Ser Gln Lys Asp Val Ser Ala
65                  70                  75                  80

Ser Lys Glu Val Gly Glu Glu Ala Leu Val Gly Ser Glu Pro Glu
                85                  90                  95

Gln Ser Tyr Lys Asn Asp Cys Asn Thr Pro Arg Val Leu Asn Asp Val
                100                 105                 110

Lys Asp Asn Gly Cys Gly Lys Asp Leu Gln Val Met Met Asp Asn Val
            115                 120                 125

Lys Lys Lys Ser Asp Thr Pro Asp Trp Glu Thr Leu Ile Ala Ala Thr
130                 135                 140

Thr Glu Leu Ile Tyr Gly Ser Pro Arg Glu Ser Glu Ala Phe Ser Cys
145                 150                 155                 160

Leu Leu Lys Lys Thr Ser Asn Ser Glu Ala Arg Leu Arg Gly Ser Ile
                165                 170                 175

Thr Ala Thr Ser Val Ala Val Thr Asn Thr Asp Val Val Asn Asn Glu
            180                 185                 190

Ser Glu Ser Val Asp Ala Leu Ser Ile Leu His Arg Gly Val Arg Arg
        195                 200                 205

Arg Cys Leu Asp Phe Glu Val Lys Gly Asn Asn Gln Gln Thr Leu Gly
210                 215                 220

Glu Ser Ser Ser Cys Val Val Pro Ser Ile Gly Leu His Leu Asn
225                 230                 235                 240

Thr Ile Ala Met Ser Ser Lys Asp Lys Asn Val Ala Asn Glu Tyr Ser
                245                 250                 255

Phe Ser Gly Asn Ile Lys Val Gly Val Gln Ser Ser Leu Thr Pro Val
            260                 265                 270

Leu His Ser Gln His Asp Ile Val Arg Glu Asn Glu Ser Gly Lys Asp
        275                 280                 285

Ser Gly Gln Ile Ile Glu Val Val Pro Lys Ser Leu Ala Ser Val Asp
    290                 295                 300

Leu Thr Pro Ile Ser Pro Lys Lys Arg Arg Lys Ser Glu Gln Ser
305                 310                 315                 320

Gly Glu Gly Asp Ser Ser Cys Lys Arg Cys Asn Cys Lys Lys Ser Lys
                325                 330                 335

Cys Leu Lys Leu Tyr Cys Glu Cys Phe Ala Ala Gly Phe Tyr Cys Ile
            340                 345                 350

Glu Pro Cys Ser Cys Ile Asn Cys Phe Asn Lys Pro Ile His Lys Asp
            355                 360                 365

Val Val Leu Ala Thr Arg Lys Gln Ile Glu Ser Arg Asn Pro Leu Ala
    370                 375                 380

Phe Ala Pro Lys Val Ile Arg Asn Ser Asp Ser Ile Ile Glu Val Gly
385                 390                 395                 400

Glu Asp Ala Ser Lys Thr Pro Ala Ser Ala Arg His Lys Arg Gly Cys
                405                 410                 415

Asn Cys Lys Lys Ser Asn Cys Leu Lys Lys Tyr Cys Glu Cys Tyr Gln
            420                 425                 430

Gly Gly Val Gly Cys Ser Ile Asn Cys Arg Cys Glu Gly Cys Lys Asn
        435                 440                 445

Ala Phe Gly Arg Lys Asp Gly Ser Leu Phe Glu Gln Asp Glu Glu Asn
    450                 455                 460

Glu Thr Ser Gly Thr Pro Gly Thr Lys Lys Thr Gln Gln Asn Val Glu
465                 470                 475                 480

Leu Phe Lys Pro Ala Ala Pro Pro Ser Thr Pro Ile Pro Phe Arg Gln
                485                 490                 495

Pro Leu Ala Gln Leu Pro Ile Ser Ser Asn Asn Arg Leu Leu Pro Pro
            500                 505                 510

Gln Ser His Phe His His Gly Ala Ile Gly Ser Ser Ser Ser Gly Ile
        515                 520                 525

Tyr Asn Ile Arg Lys Pro Asp Met Ser Leu Leu Ser His Ser Arg Ile
    530                 535                 540

Glu Thr Ile Thr Glu Asp Ile Asp Asp Met Ser Glu Asn Leu Ile His
545                 550                 555                 560

Ser Pro Ile Thr Thr Leu Ser Pro Asn Ser Lys Arg Val Ser Leu Ser
                565                 570                 575

His Leu Asp Ser Pro Glu Ser Thr Pro Trp Arg Arg Asn Gly Glu Gly
            580                 585                 590

Arg Asn Leu Ile Arg Ser Phe Pro Thr Phe Pro Ser Leu Thr Pro His
        595                 600                 605

His

<210> SEQ ID NO 10
<211> LENGTH: 1263
<212> TYPE: PRT
<213> ORGANISM: Arabidopsis thaliana

<400> SEQUENCE: 10

Met Val Gly Gly Gly Ser Ala Gln Lys Leu Thr Thr Asn Asp Ala Leu
1               5                   10                  15

Ala Tyr Leu Lys Ala Val Lys Asp Lys Phe Gln Asp Gln Arg Gly Lys
            20                  25                  30

Tyr Asp Glu Phe Leu Glu Val Met Lys Asn Phe Lys Ser Gln Arg Val
        35                  40                  45

Asp Thr Ala Gly Val Ile Thr Arg Val Lys Glu Leu Phe Lys Gly His
    50                  55                  60

Gln Glu Leu Ile Leu Gly Phe Asn Thr Phe Leu Pro Lys Gly Phe Glu
65                  70                  75                  80

Ile Thr Leu Gln Pro Glu Asp Gly Gln Pro Pro Leu Lys Lys Arg Val
                85                  90                  95

Glu Phe Glu Glu Ala Ile Ser Phe Val Asn Lys Ile Lys Thr Arg Phe
            100                 105                 110

```
Gln Gly Asp Asp Arg Val Tyr Lys Ser Phe Leu Asp Ile Leu Asn Met
        115                 120                 125
Tyr Arg Arg Asp Ser Lys Ser Ile Thr Glu Val Tyr Gln Glu Val Ala
130                 135                 140
Ile Leu Phe Arg Asp His Ser Asp Leu Leu Val Glu Phe Thr His Phe
145                 150                 155                 160
Leu Pro Asp Thr Ser Ala Thr Ala Ser Ile Pro Ser Val Lys Thr Ser
                165                 170                 175
Val Arg Glu Arg Gly Val Ser Leu Ala Asp Lys Lys Asp Arg Ile Ile
            180                 185                 190
Thr Pro His Pro Asp His Asp Tyr Gly Thr Glu His Ile Asp Gln Asp
        195                 200                 205
Arg Glu Arg Pro Ile Lys Lys Glu Asn Lys Glu His Met Arg Gly Thr
    210                 215                 220
Asn Lys Glu Asn Glu His Arg Asp Ala Arg Asp Phe Glu Pro His Ser
225                 230                 235                 240
Lys Lys Glu Gln Phe Leu Asn Lys Lys Gln Lys Leu His Ile Arg Gly
                245                 250                 255
Asp Asp Pro Ala Glu Ile Ser Asn Gln Ser Lys Leu Ser Gly Ala Val
            260                 265                 270
Pro Ser Ser Ser Thr Tyr Asp Glu Lys Gly Ala Met Lys Ser Tyr Ser
        275                 280                 285
Gln Asp Leu Ala Ile Val Asp Arg Val Lys Glu Lys Leu Asn Ala Ser
    290                 295                 300
Glu Tyr Gln Glu Phe Leu Arg Cys Leu Asn Leu Phe Ser Lys Glu Ile
305                 310                 315                 320
Ile Ser Arg Pro Glu Leu Gln Ser Leu Val Gly Asn Leu Ile Gly Val
                325                 330                 335
Tyr Pro Asp Leu Met Asp Ser Phe Ile Glu Phe Leu Val Gln Cys Glu
            340                 345                 350
Lys Asn Glu Lys Arg Gln Ile Cys Asn Leu Leu Asn Leu Leu Ala Glu
        355                 360                 365
Gly Leu Leu Ser Gly Ile Leu Thr Lys Lys Ser Leu Trp Ser Glu Gly
    370                 375                 380
Lys Tyr Pro Gln Pro Ser Leu Asp Asn Asp Arg Asp Gln Glu His Lys
385                 390                 395                 400
Arg Asp Asp Gly Leu Arg Asp Arg Asp His Glu Lys Glu Arg Leu Glu
                405                 410                 415
Lys Ala Ala Asn Leu Lys Trp Ala Lys Pro Ile Ser Glu Leu Asp
            420                 425                 430
Leu Ser Asn Cys Glu Gln Cys Thr Pro Ser Tyr Arg Leu Leu Pro Lys
        435                 440                 445
Asn Tyr Pro Ile Ser Ile Ala Ser Gln Lys Thr Glu Ile Gly Lys Leu
    450                 455                 460
Val Leu Asn Asp His Trp Val Ser Val Thr Ser Gly Ser Glu Asp Tyr
465                 470                 475                 480
Ser Phe Ser His Met Arg Lys Asn Gln Tyr Glu Glu Ser Leu Phe Lys
                485                 490                 495
Cys Glu Asp Asp Arg Phe Glu Leu Asp Met Leu Leu Glu Ser Val Asn
            500                 505                 510
Ser Thr Thr Lys His Val Glu Glu Leu Leu Thr Lys Ile Asn Ser Asn
        515                 520                 525
```

-continued

Glu Leu Lys Thr Asn Ser Pro Ile Arg Val Glu Asp His Leu Thr Ala
    530                 535                 540

Leu Asn Leu Arg Cys Ile Glu Arg Leu Tyr Gly Asp His Gly Leu Asp
545                 550                 555                 560

Val Met Asp Val Leu Lys Lys Asn Val Ser Leu Ala Leu Pro Val Ile
                565                 570                 575

Leu Thr Arg Leu Lys Gln Lys Gln Glu Glu Trp Ala Arg Cys Arg Ser
            580                 585                 590

Asp Phe Asp Lys Val Trp Ala Glu Ile Tyr Ala Lys Asn Tyr Tyr Lys
        595                 600                 605

Ser Leu Asp His Arg Ser Phe Tyr Phe Lys Gln Gln Asp Ser Lys Lys
    610                 615                 620

Leu Ser Met Lys Ala Leu Leu Ala Glu Ile Lys Glu Ile Thr Glu Lys
625                 630                 635                 640

Lys Arg Glu Asp Asp Ser Leu Leu Ala Phe Ala Ala Gly Asn Arg Leu
                645                 650                 655

Ser Ile Ser Pro Asp Leu Glu Phe Asp Tyr Pro Asp His Asp Leu His
            660                 665                 670

Glu Asp Leu Tyr Gln Leu Ile Lys Tyr Ser Cys Ala Glu Met Cys Ser
        675                 680                 685

Thr Glu Gln Leu Asp Lys Val Met Lys Ile Trp Thr Thr Phe Val Glu
    690                 695                 700

Gln Ile Phe Gly Val Pro Ser Arg Pro Gln Gly Ala Glu Asp Gln Glu
705                 710                 715                 720

Asp Val Val Lys Ser Met Asn Gln Asn Val Lys Ser Gly Ser Ser Ser
                725                 730                 735

Ala Gly Glu Ser Glu Gly Ser Pro His Asn Tyr Ala Ser Val Ala Asp
            740                 745                 750

Ser Arg Arg Ser Lys Ser Ser Arg Lys Ala Asn Glu His Ser Gln Leu
        755                 760                 765

Gly Gln Thr Ser Asn Ser Glu Arg Asp Gly Ala Ala Gly Arg Thr Ser
    770                 775                 780

Asp Ala Leu Cys Glu Thr Ala Gln His Glu Lys Met Leu Lys Asn Val
785                 790                 795                 800

Val Thr Ser Asp Glu Lys Pro Glu Ser Lys Gln Ala Val Ser Ile Glu
                805                 810                 815

Arg Ala His Asp Ser Thr Ala Leu Ala Val Asp Gly Leu Leu Asp Gln
            820                 825                 830

Ser Asn Gly Gly Ser Ser Ile Val His Met Thr Gly His Cys Asn Asn
        835                 840                 845

Asn Leu Lys Pro Val Thr Cys Gly Thr Glu Leu Glu Leu Lys Met Asn
    850                 855                 860

Asp Gly Asn Gly Pro Lys Leu Glu Val Gly Asn Lys Lys Leu Leu Thr
865                 870                 875                 880

Asn Gly Ile Ala Val Glu Ile Thr Ser Asp Gln Glu Met Ala Gly Thr
                885                 890                 895

Ser Lys Val Glu Arg Glu Glu Gly Leu Ser Pro Asn Gly Asp Phe
            900                 905                 910

Glu Glu Asp Asn Phe Ala Val Tyr Ala Lys Thr Asp Phe Glu Thr Phe
        915                 920                 925

Ser Lys Ala Asn Asp Ser Thr Gly Asn Asn Ile Ser Gly Asp Arg Ser
    930                 935                 940

Arg Glu Gly Glu Pro Ser Cys Leu Glu Thr Arg Ala Glu Asn Asp Ala

```
                945                 950                 955                 960
Glu Gly Asp Glu Asn Ala Ala Arg Ser Ser Glu Asp Ser Arg Asn Glu
                    965                 970                 975
Tyr Glu Asn Gly Asp Val Ser Gly Thr Glu Ser Gly Gly Glu Asp
                980                 985                 990
Pro Glu Asp Asp Leu Asp Asn Asn Lys Gly Glu Ser Glu Gly Glu
        995                 1000                1005
Ala Glu Cys Met Ala Asp Ala His Asp Ala Glu Asn Gly Ser Ala
    1010                1015                1020
Leu Pro Val Ser Ala Arg Phe Leu Leu His Val Lys Pro Leu Val Lys
1025                1030                1035                1040
Tyr Val Pro Ser Ala Ile Ala Leu His Asp Lys Asp Lys Asp Ser Leu
                1045                1050                1055
Lys Asn Ser Gln Val Phe Tyr Gly Asn Asp Ser Phe Tyr Val Leu Phe
                1060                1065                1070
Arg Leu His Arg Ile Leu Tyr Glu Arg Ile Leu Ser Ala Lys Val Asn
                1075                1080                1085
Ser Ser Ser Pro Glu Gly Lys Trp Arg Thr Ser Asn Thr Lys Asn Pro
    1090                1095                1100
Thr Asp Ser Tyr Ala Arg Phe Met Thr Ala Leu Tyr Asn Leu Leu Asp
1105                1110                1115                1120
Gly Thr Ser Asp Asn Ala Lys Phe Glu Asp Asp Cys Arg Ala Ile Ile
                1125                1130                1135
Gly Thr Gln Ser Tyr Ile Leu Phe Thr Leu Asp Lys Leu Ile His Lys
                1140                1145                1150
Phe Ile Lys His Leu Gln Val Val Ala Asp Glu Met Asp Asn Lys
                1155                1160                1165
Leu Leu Gln Leu Tyr Phe Tyr Glu Lys Ser Arg Arg Pro Glu Thr Ile
    1170                1175                1180
Phe Asp Ala Val Tyr Tyr Asp Asn Thr Arg Val Leu Leu Pro Asp Glu
1185                1190                1195                1200
Asn Ile Tyr Arg Ile Glu Cys Arg Leu Ser Thr Pro Ala Lys Leu Ser
                1205                1210                1215
Ile Gln Leu Met Cys Asn Gly Leu Asp Lys Pro Asp Val Thr Ser Val
                1220                1225                1230
Ser Ile Asp Pro Thr Phe Ala Ala Tyr Leu His Asn Asp Phe Leu Ser
        1235                1240                1245
Ile Gln Pro Asn Ala Arg Glu Asp Arg Arg Ile Tyr Leu Asn Arg
    1250                1255                1260

<210> SEQ ID NO 11
<211> LENGTH: 1263
<212> TYPE: PRT
<213> ORGANISM: Arabidopsis thaliana

<400> SEQUENCE: 11

Met Val Gly Gly Gly Ser Ala Gln Lys Leu Thr Thr Asn Asp Ala Leu
1               5                   10                  15
Ala Tyr Leu Lys Ala Val Lys Asp Lys Phe Gln Asp Gln Arg Gly Lys
            20                  25                  30
Tyr Asp Glu Phe Leu Glu Val Met Lys Asn Phe Lys Ser Gln Arg Val
        35                  40                  45
Asp Thr Ala Gly Val Ile Thr Arg Val Lys Glu Leu Phe Lys Gly His
    50                  55                  60
```

-continued

```
Gln Glu Leu Ile Leu Gly Phe Asn Thr Phe Leu Pro Lys Gly Phe Glu
 65                  70                  75                  80

Ile Thr Leu Gln Pro Glu Asp Gly Gln Pro Leu Lys Lys Arg Val
                 85                  90                  95

Glu Phe Glu Glu Ala Ile Ser Phe Val Asn Lys Ile Lys Thr Arg Phe
                100                 105                 110

Gln Gly Asp Asp Arg Val Tyr Lys Ser Phe Leu Asp Ile Leu Asn Met
                115                 120                 125

Tyr Arg Arg Asp Ser Lys Ser Ile Thr Glu Val Tyr Gln Glu Val Ala
    130                 135                 140

Ile Leu Phe Arg Asp His Ser Asp Leu Leu Val Glu Phe Thr His Phe
145                 150                 155                 160

Leu Pro Asp Thr Ser Ala Thr Ala Ser Ile Pro Ser Val Lys Thr Ser
                165                 170                 175

Val Arg Glu Arg Gly Val Ser Leu Ala Asp Lys Lys Asp Arg Ile Ile
                180                 185                 190

Thr Pro His Pro Asp His Asp Tyr Gly Thr Glu His Ile Asp Gln Asp
                195                 200                 205

Arg Glu Arg Pro Ile Lys Lys Glu Asn Lys Glu His Met Arg Gly Thr
    210                 215                 220

Asn Lys Glu Asn Glu His Arg Asp Ala Arg Asp Phe Glu Pro His Ser
225                 230                 235                 240

Lys Lys Glu Gln Phe Leu Asn Lys Lys Gln Lys Leu His Ile Arg Gly
                245                 250                 255

Asp Asp Pro Ala Glu Ile Ser Asn Gln Ser Lys Leu Ser Gly Ala Val
                260                 265                 270

Pro Ser Ser Ser Thr Tyr Asp Glu Lys Gly Ala Met Lys Ser Tyr Ser
                275                 280                 285

Gln Asp Leu Ala Ile Val Asp Arg Val Lys Glu Lys Leu Asn Ala Ser
    290                 295                 300

Glu Tyr Gln Glu Phe Leu Arg Cys Leu Asn Leu Phe Ser Lys Glu Ile
305                 310                 315                 320

Ile Ser Arg Pro Glu Leu Gln Ser Leu Val Gly Asn Leu Ile Gly Val
                325                 330                 335

Tyr Pro Asp Leu Met Asp Ser Phe Ile Glu Phe Leu Val Gln Cys Glu
                340                 345                 350

Lys Asn Glu Lys Arg Gln Ile Cys Asn Leu Leu Asn Leu Leu Ala Glu
                355                 360                 365

Gly Leu Leu Ser Gly Ile Leu Thr Lys Lys Ser Leu Trp Ser Glu Gly
    370                 375                 380

Lys Tyr Pro Gln Pro Ser Leu Asp Asn Asp Arg Asp Gln Glu His Lys
385                 390                 395                 400

Arg Asp Asp Gly Leu Arg Asp Arg Asp His Glu Lys Glu Arg Leu Glu
                405                 410                 415

Lys Ala Ala Ala Asn Leu Lys Trp Ala Lys Pro Ile Ser Glu Leu Asp
                420                 425                 430

Leu Ser Asn Cys Glu Gln Cys Thr Pro Ser Tyr Arg Leu Leu Pro Lys
                435                 440                 445

Asn Tyr Pro Ile Ser Ile Ala Ser Gln Lys Thr Glu Ile Gly Lys Leu
                450                 455                 460

Val Leu Asn Asp His Trp Val Ser Val Thr Ser Gly Ser Glu Asp Tyr
465                 470                 475                 480

Ser Phe Ser His Met Arg Lys Asn Gln Tyr Glu Glu Ser Leu Phe Lys
```

-continued

```
                485                 490                 495
Cys Glu Asp Asp Arg Phe Glu Leu Asp Met Leu Leu Glu Ser Val Asn
                500                 505                 510

Ser Thr Thr Lys His Val Glu Glu Leu Leu Thr Lys Ile Asn Ser Asn
                515                 520                 525

Glu Leu Lys Thr Asn Ser Pro Ile Arg Val Glu Asp His Leu Thr Ala
                530                 535                 540

Leu Asn Leu Arg Cys Ile Glu Arg Leu Tyr Gly Asp His Gly Leu Asp
545                 550                 555                 560

Val Met Asp Val Leu Lys Lys Asn Val Ser Leu Ala Leu Pro Val Ile
                565                 570                 575

Leu Thr Arg Leu Lys Gln Lys Gln Glu Glu Trp Ala Arg Cys Arg Ser
                580                 585                 590

Asp Phe Asp Lys Val Trp Ala Glu Ile Tyr Ala Lys Asn Tyr Tyr Lys
                595                 600                 605

Ser Leu Asp His Arg Ser Phe Tyr Phe Lys Gln Gln Asp Ser Lys Lys
                610                 615                 620

Leu Ser Met Lys Ala Leu Leu Ala Glu Ile Lys Glu Ile Thr Glu Lys
625                 630                 635                 640

Lys Arg Glu Asp Asp Ser Leu Leu Ala Phe Ala Ala Gly Asn Arg Leu
                645                 650                 655

Ser Ile Ser Pro Asp Leu Glu Phe Asp Tyr Pro Asp His Asp Leu His
                660                 665                 670

Glu Asp Leu Tyr Gln Leu Ile Lys Tyr Ser Cys Ala Glu Met Cys Ser
                675                 680                 685

Thr Glu Gln Leu Asp Lys Val Met Lys Ile Trp Thr Thr Phe Val Glu
                690                 695                 700

Gln Ile Phe Gly Val Pro Ser Arg Pro Gln Gly Ala Glu Asp Gln Glu
705                 710                 715                 720

Asp Val Val Lys Ser Met Asn Gln Asn Val Lys Ser Gly Ser Ser Ser
                725                 730                 735

Ala Gly Glu Ser Glu Gly Ser Pro His Asn Tyr Ala Ser Val Ala Asp
                740                 745                 750

Ser Arg Arg Ser Lys Ser Ser Arg Lys Ala Asn Glu His Ser Gln Leu
                755                 760                 765

Gly Gln Thr Ser Asn Ser Glu Arg Asp Gly Ala Ala Gly Arg Thr Ser
                770                 775                 780

Asp Ala Leu Cys Glu Thr Ala Gln His Glu Lys Met Leu Lys Asn Val
785                 790                 795                 800

Val Thr Ser Asp Glu Lys Pro Glu Ser Lys Gln Ala Val Ser Ile Glu
                805                 810                 815

Arg Ala His Asp Ser Thr Ala Leu Ala Val Asp Gly Leu Leu Asp Gln
                820                 825                 830

Ser Asn Gly Gly Ser Ser Ile Val His Met Thr Gly His Cys Asn Asn
                835                 840                 845

Asn Leu Lys Pro Val Thr Cys Gly Thr Glu Leu Glu Leu Lys Met Asn
850                 855                 860

Asp Gly Asn Gly Pro Lys Leu Glu Val Gly Asn Lys Lys Leu Leu Thr
865                 870                 875                 880

Asn Gly Ile Ala Val Glu Ile Thr Ser Asp Gln Glu Met Ala Gly Thr
                885                 890                 895

Ser Lys Val Glu Arg Glu Glu Gly Glu Leu Ser Pro Asn Gly Asp Phe
                900                 905                 910
```

```
Glu Glu Asp Asn Phe Ala Val Tyr Ala Lys Thr Asp Phe Glu Thr Phe
            915                 920                 925

Ser Lys Ala Asn Asp Ser Thr Gly Asn Asn Ile Ser Gly Asp Arg Ser
        930                 935                 940

Arg Glu Gly Glu Pro Ser Cys Leu Glu Thr Arg Ala Glu Asn Asp Ala
945                 950                 955                 960

Glu Gly Asp Glu Asn Ala Ala Arg Ser Ser Glu Asp Ser Arg Asn Glu
                965                 970                 975

Tyr Glu Asn Gly Asp Val Ser Gly Thr Glu Ser Gly Gly Glu Asp
            980                 985                 990

Pro Glu Asp Asp Leu Asp Asn Asn Lys Gly Glu Ser Glu Gly Glu
        995                 1000                1005

Ala Glu Cys Met Ala Asp Ala His Asp Ala Glu Asn Gly Ser Ala
    1010                1015                1020

Leu Pro Val Ser Ala Arg Phe Leu Leu His Val Lys Pro Leu Val Lys
1025                1030                1035                1040

Tyr Val Pro Ser Ala Ile Ala Leu His Asp Lys Asp Lys Asp Ser Leu
            1045                1050                1055

Lys Asn Ser Gln Val Phe Tyr Gly Asn Asp Ser Phe Tyr Val Leu Phe
        1060                1065                1070

Arg Leu His Arg Ile Leu Tyr Glu Arg Ile Leu Ser Ala Lys Val Asn
    1075                1080                1085

Ser Ser Ser Pro Glu Gly Lys Trp Arg Thr Ser Asn Thr Lys Asn Pro
    1090                1095                1100

Thr Asp Ser Tyr Ala Arg Phe Met Thr Ala Leu Tyr Asn Leu Leu Asp
1105                1110                1115                1120

Gly Thr Ser Asp Asn Ala Lys Phe Glu Asp Asp Cys Arg Ala Ile Ile
            1125                1130                1135

Gly Thr Gln Ser Tyr Ile Leu Phe Thr Leu Asp Lys Leu Ile His Lys
        1140                1145                1150

Phe Ile Lys His Leu Gln Val Val Ala Asp Glu Met Asp Asn Lys
    1155                1160                1165

Leu Leu Gln Leu Tyr Phe Tyr Glu Lys Ser Arg Arg Pro Glu Thr Ile
1170                1175                1180

Phe Asp Ala Val Tyr Tyr Asp Asn Thr Arg Val Leu Leu Pro Asp Glu
1185                1190                1195                1200

Asn Ile Tyr Arg Ile Glu Cys Arg Leu Ser Thr Pro Ala Lys Leu Ser
            1205                1210                1215

Ile Gln Leu Met Cys Asn Gly Leu Asp Lys Pro Asp Val Thr Ser Val
        1220                1225                1230

Ser Ile Asp Pro Thr Phe Ala Ala Tyr Leu His Asn Asp Phe Leu Ser
    1235                1240                1245

Ile Gln Pro Asn Ala Arg Glu Asp Arg Arg Ile Tyr Leu Asn Arg
    1250                1255                1260

<210> SEQ ID NO 12
<211> LENGTH: 566
<212> TYPE: PRT
<213> ORGANISM: Arabidopsis thaliana

<400> SEQUENCE: 12

Met Asn Leu Lys Lys Ser Arg Ser Glu Asn Ser Ser Val Ala Ser Ser
1               5                   10                  15

Gly Ser Lys Ile Glu Glu Gln Thr Glu Lys Ser Ala Glu Pro Thr Thr
```

```
                    20                  25                  30
Ile Lys Val Gln Lys Lys Ala Gly Thr Pro Gly Arg Ser Ile Asp Val
                35                  40                  45

Phe Ala Val Gln Cys Glu Lys Cys Met Lys Trp Arg Lys Ile Asp Thr
        50                  55                  60

Gln Asp Glu Tyr Glu Asp Ile Arg Ser Arg Val Gln Glu Asp Pro Phe
65                  70                  75                  80

Phe Cys Lys Thr Lys Glu Gly Val Ser Cys Glu Asp Val Gly Asp Leu
                85                  90                  95

Asn Tyr Asp Ser Ser Arg Thr Trp Val Ile Asp Lys Pro Gly Leu Pro
            100                 105                 110

Arg Thr Pro Arg Gly Phe Lys Arg Ser Leu Ile Leu Arg Lys Asp Tyr
        115                 120                 125

Ser Lys Met Asp Ala Tyr Tyr Ile Thr Pro Thr Gly Lys Lys Leu Lys
    130                 135                 140

Ser Arg Asn Glu Ile Ala Ala Phe Ile Asp Ala Asn Gln Asp Tyr Lys
145                 150                 155                 160

Tyr Ala Leu Leu Gly Asp Phe Asn Phe Thr Val Pro Lys Val Met Glu
                165                 170                 175

Glu Thr Val Pro Ser Gly Ile Leu Ser Asp Arg Thr Pro Lys Pro Ser
            180                 185                 190

Arg Lys Phe Leu Ser Gly Lys Met Gln Gly Gly Gly Arg Asp Pro
        195                 200                 205

Phe Gly Gly Gly Phe Gly Pro Phe Gly Phe Gly Gly Ser
    210                 215                 220

Phe Gly Gly Phe Gly Arg Gly Ser Phe Gly Phe Gly Gly Pro Asn
225                 230                 235                 240

Gly Pro Pro Ser Leu Met Ser Asn Phe Phe Gly Gly Arg Asp Pro Phe
                245                 250                 255

Asp Asp Pro Phe Phe Thr Gln Pro Phe Gly Gly Met Phe Gln Ser
            260                 265                 270

Asn Phe Phe Gly Pro Ser Met Asn Pro Phe Ala Glu Met His Arg Leu
        275                 280                 285

Pro Gln Gly Phe Ile Glu Asn Asn Gln Pro Pro Gly Pro Ser Arg Ser
    290                 295                 300

Arg Gly Pro Val Ile Glu Glu Ile Asp Ser Asp Glu Lys Glu Gly
305                 310                 315                 320

Glu Gly Asp Lys Glu Lys Lys Gly Ser Leu Gly Lys His Gly Arg Ser
                325                 330                 335

Ser Ser Glu Ala Glu Thr Glu Asp Ala Arg Val Arg Glu Arg Arg Asn
            340                 345                 350

Arg Gln Met Gln Ser Met Asn Val Asn Ala Glu Arg Arg Asn Arg Glu
        355                 360                 365

Met Gln Asn Met Asn Val Asn Ala Glu Arg Arg Asn Pro Gln Met Gln
    370                 375                 380

Asn Met Asn Val Asn Ala Met Val Asn Asn Gly Gln Trp Gln Pro Gln
385                 390                 395                 400

Thr Gly Ser Tyr Ser Phe Gln Ser Ser Thr Val Thr Tyr Gly Gly Gln
                405                 410                 415

Asn Gly Asn Tyr Tyr Thr Ser Ser Lys Thr Arg Arg Thr Gly Ser Asp
            420                 425                 430

Gly Gly His Thr Val Ala Arg Lys Leu Asn Ser Asp Gly Arg Val Asp
        435                 440                 445
```

Thr Thr Gln Thr Leu His Asn Leu Asn Glu Gly Gly Leu Val Asn Arg
            450                 455                 460

Glu Gln Pro Met Leu Leu Pro Ser Thr Asp Pro Ser Pro Ser His Ala
465                 470                 475                 480

Arg Ala Glu Ser Ser Arg Arg Pro Lys Ala Ala Met Asn Leu Ile Pro
                485                 490                 495

Ile Leu Ala Ile Ala Val Ala Ser Ala Ala Phe Leu Ser Glu Leu Val
                500                 505                 510

Ser Met Ser Leu Pro Glu Ser Ile Trp Arg Met Met Thr Pro Lys Ala
            515                 520                 525

Lys Ile Ser Val Phe Ser Val Asn Phe Pro Val Val Thr Tyr Ser Gly
            530                 535                 540

Ala Lys Tyr Pro Ile Ala Ala Leu Val Leu Ser Ala Glu Lys Thr Ile
545                 550                 555                 560

Ser Ser Ala Arg Arg Leu
                565

<210> SEQ ID NO 13
<211> LENGTH: 177
<212> TYPE: PRT
<213> ORGANISM: Zea mays

<400> SEQUENCE: 13

Met Thr Thr Gly Ser Thr Pro Gly Ser Ala Pro Ser Gln Arg Lys Arg
1               5                   10                  15

Asn Ser Thr Lys Asp Ser Val Ala Leu Tyr Ala Val Gln Cys Tyr Lys
                20                  25                  30

Cys Tyr Lys Trp Ser Thr Val Pro Lys Glu Glu Phe Glu Thr Leu Arg
            35                  40                  45

Glu Asn Phe Thr Lys Asp Pro Trp Phe Cys Ser Arg Arg Pro Asp Ser
50                  55                  60

Ser Cys Glu Asp Asp Ala Asp Ile Glu Tyr Asp Ser Ser Arg Ile Trp
65                  70                  75                  80

Val Leu Asp Lys Pro Asn Ile Pro Lys Pro Pro Glu Thr Glu Arg
                85                  90                  95

Leu Val Val Met Arg Gly Asp Tyr Ser Lys Met Asp Thr Tyr Tyr Val
                100                 105                 110

Met Pro Asn Gly Lys Arg Ala Arg Cys Ala Gly Asp Val Asp Lys Phe
            115                 120                 125

Leu Glu Ala Asn Pro Glu Tyr Lys Asp Arg Ile Ser Ala Ser Asp Phe
130                 135                 140

Ser Phe Ala Pro Pro Lys Val Val Glu Glu Thr Val Ser His Asn Pro
145                 150                 155                 160

Ala Trp Gln Ala Ala Lys Ala Lys Lys Gln Glu Lys Ala Glu Ala Gln
                165                 170                 175

Lys

<210> SEQ ID NO 14
<211> LENGTH: 428
<212> TYPE: PRT
<213> ORGANISM: Zea mays

<400> SEQUENCE: 14

Met Pro Ala Pro Asp Gly Trp Thr Lys Lys Phe Thr Pro Gln Arg Gly
1               5                   10                  15

-continued

```
Gly Arg Ser Glu Ile Val Phe Val Ser Pro Thr Gly Glu Glu Ile Lys
             20                  25                  30

Asn Lys Arg Gln Leu Ser Gln Tyr Leu Lys Ala His Pro Gly Gly Pro
         35                  40                  45

Ala Ala Ser Asp Phe Asp Trp Gly Thr Gly Asp Thr Pro Arg Arg Ser
 50                  55                  60

Ala Arg Ile Ser Glu Lys Val Lys Val Phe Asp Ser Pro Glu Gly Glu
 65                  70                  75                  80

Lys Ile Pro Lys Arg Ser Arg Asn Ser Ser Gly Arg Lys Gly Arg Gln
                 85                  90                  95

Gly Lys Lys Glu Ala Pro Glu Thr Glu Ala Lys Asp Ala Glu Thr
            100                 105                 110

Gly Gln Asp Ala Pro Ser Glu Asp Gly Thr Lys Glu Thr Asp Val Glu
            115                 120                 125

Met Lys Pro Ala Glu Glu Ala Lys Glu Ala Pro Thr Glu Thr Asp Asp
130                 135                 140

Ala Glu Lys Ala Ala Asp Lys Ala Asp Asp Thr Pro Ala Pro Ala Pro
145                 150                 155                 160

Met Glu Glu Asp Glu Lys Glu Thr Glu Lys Pro Ala Glu Ala Val Val
                165                 170                 175

Ala Pro Leu Ala Gln Ser Glu Glu Lys Lys Glu Asp Ala Lys Pro Asp
            180                 185                 190

Glu Pro Glu Ala Val Ala Pro Ala Pro Val Ser Asn Pro Thr Glu Asn
            195                 200                 205

Ser Ala Pro Ala Pro Ala Glu Pro Ala Ala Val Pro Ala Pro Val Pro
210                 215                 220

Glu Thr Glu Ser Val Ala Glu Pro Ala Ala Val Leu Ala Pro Ala Pro
225                 230                 235                 240

Glu Thr Lys Pro Asp Ala Lys Pro Ala Ala Val Pro Ala Pro Ala Pro
                245                 250                 255

Glu Asn Lys Pro Asp Ala Glu Pro Ala Ala Ala Ala Pro Val Pro
            260                 265                 270

Asp Thr Lys Ser Val Ala Glu Pro Ala Ala Ala Pro Ala Pro Asp Thr
            275                 280                 285

Lys Ser Val Ala Glu Pro Ala Ala Ala Pro Val Pro Glu Thr Lys
290                 295                 300

Leu Val Ala Glu Ser Ala Ala Asp Ala Val Ala Ala Pro Ala Pro Glu
305                 310                 315                 320

Thr Lys Ser Asp Ala Glu Pro Ala Ala Ala Pro Val Pro Glu Thr Lys
                325                 330                 335

Pro Val Ala Glu Ser Ala Ala Asp Ala Val Ala Ala Pro Ala Pro Glu
            340                 345                 350

Thr Lys Ser Asp Ala Glu Pro Ala Ala Ala Asp Pro Ala Pro Glu
            355                 360                 365

Ile Lys Ser Asp Ala Ala Ala Asp Pro Ala Pro Gly Thr Lys Ala
370                 375                 380

Asp Ala Ala Thr Asp Ala Ala Pro Gly Ala Glu Pro Asp Ala Ala
385                 390                 395                 400

Pro Leu Glu Asn Thr Ala Ala Asp Lys Gly Gly Ser Glu Glu Ser Ser
                405                 410                 415

Gln Pro Val Asn Asn Val Asn Asn Gly His Ser Thr
            420                 425
```

-continued

```
<210> SEQ ID NO 15
<211> LENGTH: 158
<212> TYPE: PRT
<213> ORGANISM: Oryza sativa
<220> FEATURE:
<221> NAME/KEY: VARIANT
<222> LOCATION: 144
<223> OTHER INFORMATION: Xaa = Any Amino Acid

<400> SEQUENCE: 15

Glu Ile Thr Val Glu Glu Ser Lys Glu Ala Pro Thr Thr Thr Lys Glu
 1               5                  10                  15

Ala Thr His Arg Ile Ser Arg Gly Ile His Asp Lys Gly His Ser Leu
            20                  25                  30

Thr Arg Lys Leu Lys Ser Asp Gly Asn Val Asp Thr Thr Gln Ile Leu
        35                  40                  45

His Asn Leu His Glu Asp Glu Leu Ala Gly Phe Glu Glu Ser Trp Lys
    50                  55                  60

Gly Asn Ala Arg His His Leu Ala Gly Leu Asn Gln Asn Ala Gly Thr
65                  70                  75                  80

Ser Asn Asn Asn Gln Val Thr Val Ala Pro Val Asp Val Ala Gly
                85                  90                  95

Asn Pro Leu Gly Val Gly Leu Phe Leu Glu Glu Ser Lys Ala Val Ile
            100                 105                 110

Lys Asp Gly Thr Ser Glu Asp Arg Asn His Val Ser Tyr Gln Ser Pro
        115                 120                 125

Lys Gly Phe Leu Leu Tyr Ile Tyr Gly Ser Lys Ser Val Asn Cys Xaa
    130                 135                 140

Val Val Glu Ser Ser Lys Ile Gln Val Gln Arg Ile Leu Ile
145                 150                 155

<210> SEQ ID NO 16
<211> LENGTH: 524
<212> TYPE: PRT
<213> ORGANISM: Arabidopsis thaliana

<400> SEQUENCE: 16

Met Asp Asp Gly Asp Leu Gly Asn Asn His His Asn Phe Leu Gly Gly
 1               5                  10                  15

Ala Gly Asn Arg Leu Ser Ala Glu Ser Leu Pro Leu Ile Asp Thr Arg
            20                  25                  30

Leu Leu Ser Gln Ser Glu Leu Arg Ala Leu Ser Gln Cys Ser Ser Leu
        35                  40                  45

Ser Pro Ser Ser Ser Ala Ser Leu Ala Ala Ser Ala Gly Gly Asp Asp
    50                  55                  60

Asp Leu Thr Pro Lys Ile Asp Arg Ser Val Phe Asn Glu Ser Ala Gly
65                  70                  75                  80

Ser Arg Lys Gln Thr Phe Leu Arg Leu Arg Leu Ala Arg His Pro Gln
                85                  90                  95

Pro Pro Glu Glu Pro Pro Ser Pro Gln Arg Gln Arg Asp Asp Ser Ser
            100                 105                 110

Arg Glu Glu Gln Thr Gln Val Ala Ser Leu Leu Arg Ser Leu Phe Asn
        115                 120                 125

Val Asp Ser Asn Gln Ser Lys Glu Glu Glu Asp Glu Gly Glu Glu
    130                 135                 140

Leu Glu Asp Asn Glu Gly Gln Ile His Tyr Asn Ser Tyr Val Tyr Gln
145                 150                 155                 160
```

```
Arg Pro Asn Leu Asp Ser Ile Gln Asn Val Leu Ile Gln Gly Thr Ser
                165                 170                 175
Gly Asn Lys Ile Lys Arg Lys Arg Gly Arg Pro Arg Lys Ile Arg Asn
            180                 185                 190
Pro Ser Glu Glu Asn Glu Val Leu Asp Leu Thr Gly Glu Ala Ser Thr
        195                 200                 205
Tyr Val Phe Val Asp Lys Thr Ser Ser Asn Leu Gly Met Val Ser Arg
    210                 215                 220
Val Gly Ser Ser Gly Ile Ser Leu Asp Ser Asn Ser Val Lys Arg Lys
225                 230                 235                 240
Arg Gly Arg Pro Pro Lys Asn Lys Glu Glu Ile Met Asn Leu Glu Lys
                245                 250                 255
Arg Asp Ser Ala Ile Val Asn Ile Ser Ala Phe Asp Lys Glu Glu Leu
            260                 265                 270
Val Val Asn Leu Glu Asn Arg Glu Gly Thr Ile Val Asp Leu Ser Ala
        275                 280                 285
Leu Ala Ser Val Ser Glu Asp Pro Tyr Glu Glu Leu Arg Arg Ile
    290                 295                 300
Thr Val Gly Leu Lys Thr Lys Glu Glu Ile Leu Gly Phe Leu Glu Gln
305                 310                 315                 320
Leu Asn Gly Glu Trp Val Asn Ile Gly Lys Lys Lys Val Val Asn
                325                 330                 335
Ala Cys Asp Tyr Gly Gly Tyr Leu Pro Arg Gly Trp Arg Leu Met Leu
            340                 345                 350
Tyr Ile Lys Arg Lys Gly Ser Asn Leu Leu Ala Cys Arg Arg Tyr
        355                 360                 365
Ile Ser Pro Asp Gly Gln Gln Phe Glu Thr Cys Lys Glu Val Ser Thr
    370                 375                 380
Tyr Leu Arg Ser Leu Leu Glu Ser Pro Ser Lys Asn Gln His Tyr Tyr
385                 390                 395                 400
Leu Gln Ser Asp Asn Lys Thr Leu Gly Gln Gln Pro Val Ile Ala Asn
                405                 410                 415
Glu Ser Leu Leu Gly Asn Ser Asp Met Asp Ser Glu Thr Met Gln
            420                 425                 430
Tyr Leu Glu Ser Gly Arg Thr Ser Ser Glu Val Phe Glu Glu Ala Lys
        435                 440                 445
Ala Val Glu Asn Gly Asn Glu Ala Asp Arg Val Lys Thr Ser Leu Met
    450                 455                 460
Gln Lys Asp Asp Asn Ala Asp Phe Leu Asn Gly Val Glu Asp Asn Asp
465                 470                 475                 480
Asp Asp Met Lys Lys Arg Asp Gly Asn Met Glu Asn Leu Ala Thr Leu
                485                 490                 495
Ser Asn Ser Glu Met Thr Lys Ser Leu Pro Thr Thr Thr Asn Glu Leu
            500                 505                 510
Gln Gln Tyr Phe Ser Ser Gln Ile Asn Arg Val Gln
        515                 520

<210> SEQ ID NO 17
<211> LENGTH: 701
<212> TYPE: DNA
<213> ORGANISM: Artificial Sequence
<220> FEATURE:
<223> OTHER INFORMATION: Synthetically generated transcriptional
      activator
<220> FEATURE:
<221> NAME/KEY: CDS
```

<222> LOCATION: (17)...(694)

<400> SEQUENCE: 17

```
aagcttggat ccaaca atg aag ctc ctg tcc tcc atc gag cag gcc tgc gac        52
                  Met Lys Leu Leu Ser Ser Ile Glu Gln Ala Cys Asp
                   1               5                  10 atc tgc cgc ctc aag aag ctc aag tgc tcc aag gag aag ccg aag tgc         100
Ile Cys Arg Leu Lys Lys Leu Lys Cys Ser Lys Glu Lys Pro Lys Cys
         15                  20                  25 gcc aag tgt ctg aag aac aac tgg gag tgt cgc tac tct ccc aaa acc         148
Ala Lys Cys Leu Lys Asn Asn Trp Glu Cys Arg Tyr Ser Pro Lys Thr
 30                  35                  40 aag cgc tcc ccg ctg acc cgc gcc cac ctc acc gaa gtg gag tcc cgc         196
Lys Arg Ser Pro Leu Thr Arg Ala His Leu Thr Glu Val Glu Ser Arg
 45                  50                  55                  60 ctg gag cgc ctg gag cag ctc ttc ctc ctg atc ttc cct cga gag gac         244
Leu Glu Arg Leu Glu Gln Leu Phe Leu Leu Ile Phe Pro Arg Glu Asp
                 65                  70                  75 ctc gac atg atc ctg aaa atg gac tcc ctc cag gac atc aaa gcc ctg         292
Leu Asp Met Ile Leu Lys Met Asp Ser Leu Gln Asp Ile Lys Ala Leu
                     80                  85                  90 ctc acc ggc ctc ttc gtc cag gac aac gtg aac aaa gac gcc gtc acc         340
Leu Thr Gly Leu Phe Val Gln Asp Asn Val Asn Lys Asp Ala Val Thr
                         95                 100                 105 gac cgc ctg gcc tcc gtg gag acc gac atg ccc ctc acc ctg cgc cag         388
Asp Arg Leu Ala Ser Val Glu Thr Asp Met Pro Leu Thr Leu Arg Gln
            110                 115                 120 cac cgc atc agc gcg acc tcc tcc tcg gag gag agc agc aac aag ggc         436
His Arg Ile Ser Ala Thr Ser Ser Ser Glu Glu Ser Ser Asn Lys Gly
125                 130                 135                 140 cag cgc cag ttg acc gtc tcg acg gcc ccc ccg acc gac gtc agc ctg         484
Gln Arg Gln Leu Thr Val Ser Thr Ala Pro Pro Thr Asp Val Ser Leu
                145                 150                 155 ggg gac gag ctc cac tta gac ggc gag gac gtg gcg atg gcg cat gcc         532
Gly Asp Glu Leu His Leu Asp Gly Glu Asp Val Ala Met Ala His Ala
                    160                 165                 170 gac gcg cta gac gat ttc gat ctg gac atg ttg ggg gac ggg gat tcc         580
Asp Ala Leu Asp Asp Phe Asp Leu Asp Met Leu Gly Asp Gly Asp Ser
                        175                 180                 185 ccg ggg ccg gga ttt acc ccc cac gac tcc gcc ccc tac ggc gct ctg         628
Pro Gly Pro Gly Phe Thr Pro His Asp Ser Ala Pro Tyr Gly Ala Leu
            190                 195                 200 gat atg gcc gac ttc gag ttt gag cag atg ttt acc gat gcc ctt gga         676
Asp Met Ala Asp Phe Glu Phe Glu Gln Met Phe Thr Asp Ala Leu Gly
205                 210                 215                 220 att gac gag tac ggt ggg tagatct                                         701
Ile Asp Glu Tyr Gly Gly
                225
```

<210> SEQ ID NO 18
<211> LENGTH: 226
<212> TYPE: PRT
<213> ORGANISM: Artificial Sequence
<220> FEATURE:
<223> OTHER INFORMATION: Synthetically generated transcriptional activator

<400> SEQUENCE: 18

```
Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
```

```
                20                  25                  30
Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
50                      55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Thr Ala Pro Pro Thr Asp Val Ser Leu Gly Asp Glu Leu
145                 150                 155                 160

His Leu Asp Gly Glu Asp Val Ala Met Ala His Ala Asp Ala Leu Asp
                165                 170                 175

Asp Phe Asp Leu Asp Met Leu Gly Asp Gly Asp Ser Pro Gly Pro Gly
            180                 185                 190

Phe Thr Pro His Asp Ser Ala Pro Tyr Gly Ala Leu Asp Met Ala Asp
        195                 200                 205

Phe Glu Phe Glu Gln Met Phe Thr Asp Ala Leu Gly Ile Asp Glu Tyr
    210                 215                 220

Gly Gly
225

<210> SEQ ID NO 19
<211> LENGTH: 612
<212> TYPE: PRT
<213> ORGANISM: Artificial Sequence
<220> FEATURE:
<223> OTHER INFORMATION: Synthetically generated construct
<220> FEATURE:
<221> NAME/KEY: VARIANT
<222> LOCATION: 586
<223> OTHER INFORMATION: Xaa = Any Amino Acid

<400> SEQUENCE: 19

Met Ser Lys Ile Thr Leu Gly Asn Glu Ser Ile Val Gly Ser Leu Thr
1               5                   10                  15

Pro Ser Asn Lys Lys Ser Tyr Lys Val Thr Asn Arg Ile Gln Glu Gly
            20                  25                  30

Lys Lys Pro Leu Tyr Ala Val Phe Asn Phe Leu Asp Ala Arg Phe
        35                  40                  45

Phe Asp Val Phe Val Thr Ala Gly Gly Asn Arg Ile Thr Leu Tyr Asn
    50                  55                  60

Cys Leu Gly Asp Gly Ala Ile Ser Ala Leu Gln Ser Tyr Ala Asp Glu
65                  70                  75                  80

Asp Lys Glu Glu Ser Phe Tyr Thr Val Ser Trp Ala Cys Gly Val Asn
                85                  90                  95

Gly Asn Pro Tyr Val Ala Ala Gly Gly Val Lys Gly Ile Ile Arg Val
            100                 105                 110

Ile Asp Val Asn Ser Glu Thr Ile His Lys Ser Leu Val Gly His Gly
        115                 120                 125
```

```
Asp Ser Val Asn Glu Ile Arg Thr Gln Pro Leu Lys Pro Gln Leu Val
        130                 135                 140

Ile Thr Ala Ser Lys Asp Glu Ser Val Arg Leu Trp Asn Val Glu Thr
145                 150                 155                 160

Gly Ile Cys Ile Leu Ile Phe Ala Gly Ala Gly His Arg Tyr Glu
                165                 170                 175

Val Leu Ser Val Asp Phe His Pro Ser Asp Ile Tyr Arg Phe Ala Ser
        180                 185                 190

Cys Gly Met Asp Thr Thr Ile Lys Ile Trp Ser Met Lys Glu Phe Trp
        195                 200                 205

Thr Tyr Val Glu Lys Ser Phe Thr Trp Thr Asp Asp Pro Ser Lys Phe
    210                 215                 220

Pro Thr Lys Phe Val Gln Phe Pro Val Phe Thr Ala Ser Ile His Thr
225                 230                 235                 240

Asn Tyr Val Asp Cys Asn Arg Trp Phe Gly Asp Phe Ile Leu Ser Lys
                245                 250                 255

Ser Val Asp Asn Glu Ile Leu Leu Trp Glu Pro Gln Leu Lys Glu Asn
                260                 265                 270

Ser Pro Gly Glu Gly Ala Ser Asp Val Leu Leu Arg Tyr Pro Val Pro
            275                 280                 285

Met Cys Asp Ile Trp Phe Ile Lys Phe Ser Cys Asp Leu His Leu Ser
    290                 295                 300

Ser Val Ala Ile Gly Asn Gln Glu Gly Lys Val Tyr Val Trp Asp Leu
305                 310                 315                 320

Lys Ser Cys Pro Pro Val Leu Ile Thr Lys Leu Ser His Asn Gln Ser
                325                 330                 335

Lys Ser Val Ile Arg Gln Thr Ala Met Ser Val Asp Gly Ser Thr Ile
            340                 345                 350

Leu Ala Cys Cys Glu Asp Gly Thr Ile Trp Arg Trp Asp Val Ile Thr
        355                 360                 365

Lys Gly Ser Pro Gly Gly Gly Gly Gly Gly Gly Gly Gly Gly Gly
    370                 375                 380

Gly Gly Gly Met Arg Thr His Ile Glu Gly His Glu Glu Leu Asp Ala
385                 390                 395                 400

Ala Ser Leu Arg Glu His Glu Glu Phe Thr Lys Val Lys Asn Ile Ser
                405                 410                 415

Thr Ile Glu Leu Gly Lys Tyr Glu Ile Glu Thr Trp Tyr Phe Ser Pro
            420                 425                 430

Phe Pro Pro Glu Tyr Asn Asp Cys Val Lys Leu Phe Cys Glu Phe
            435                 440                 445

Cys Leu Asn Phe Met Lys Arg Lys Glu Gln Leu Gln Arg His Met Arg
    450                 455                 460

Lys Cys Asp Leu Lys His Pro Pro Gly Asp Glu Ile Tyr Arg Ser Gly
465                 470                 475                 480

Thr Leu Ser Met Phe Glu Val Asp Gly Lys Lys Asn Lys Val Tyr Ala
                485                 490                 495

Gln Asn Leu Cys Tyr Leu Ala Lys Leu Phe Leu Asp His Lys Thr Leu
            500                 505                 510

Tyr Tyr Asp Val Asp Leu Phe Leu Phe Tyr Val Leu Cys Glu Cys Asp
        515                 520                 525

Asp Arg Gly Cys His Met Val Gly Tyr Phe Ser Lys Glu Lys His Ser
    530                 535                 540

Glu Glu Ala Tyr Asn Leu Ala Cys Ile Leu Thr Leu Pro Ser Tyr Gln
```

```
545                 550                 555                 560
Arg Lys Gly Tyr Gly Lys Phe Leu Ile Ala Phe Ser Tyr Glu Leu Ser
                565                 570                 575
Lys Lys Glu Gly Lys Val Gly Thr Pro Xaa Lys Thr Leu Val Gly Ser
            580                 585                 590
Arg Leu Thr Lys Leu Gln Arg Leu Leu Asp Ser Cys Ser Ile Arg Asn
        595                 600                 605
Leu Glu Lys Thr
        610

<210> SEQ ID NO 20
<211> LENGTH: 2867
<212> TYPE: DNA
<213> ORGANISM: Artificial Sequence
<220> FEATURE:
<223> OTHER INFORMATION: Synthetically generated construct

<400> SEQUENCE: 20
cggagtactg tcctccgagc ggagtactgt cctccgagcg gagtactgtc ctccgagcgg      60
agtactgtcc tccgagcgga gtactgtcct ccgagcggag actctagaac gattatttag     120
gtgataagag tggacaatga tcgttgacac gtggacggtc cacaaattct agttttgcct     180
ataagtatca aagctgaatg tgtaagttgg atccaacacc agttgttgtt gcatgagaga     240
cttgtgagct tagattagtg tgcgagagtc agacagagag agagatttcg aatatcgaat     300
gtcgaagata accttaggga acgagtcaat agttgggtct ttgactccat cgaataagaa     360
atcgtacaaa gtgacgaata ggattcagga agggaagaaa cctttgtatg ctgttgtttt     420
caacttcctt gatgctcgtt tcttcgatgt cttcgttacc gctggtggaa atcggattac     480
tctgtacaat tgtctcggag atggtgccat atcagcattg caatcctatg ctgatgaaga     540
taaggaagag tcgttttaca cggtaagttg ggcgtgtggc gttaatggga acccatatgt     600
tgcggctgga ggagtaaaag gtataatccg agtcattgac gtcaacagtg aaacgattca     660
taagagtctt gtgggtcatg gagattcagt gaacgaaatc aggacacaac ctttaaaacc     720
tcaacttgtg attactgcta gcaaggatga atctgttcgt ttgtggaatg ttgaaactgg     780
gatatgtatt ttgatatttg ctggagctgg aggtcatcgc tatgaagttc taagtgtgga     840
ttttcatccg tctgatattt accgctttgc tagttgtggt atggacacca ctattaaaat     900
atggtcaatg aaagagtttt ggacgtacgt cgagaagtca ttcacatgga ctgatgatcc     960
atcaaaattc cccacaaaat ttgtccaatt ccctgtattt acagcttcca ttcatacaaa    1020
ttatgtagat tgtaaccgtt ggtttggtga tttatcctc tcaaagagtg tggacaacga    1080
gatcctgttg tgggaaccac aactgaaaga gaattctcct ggcgagggag cttcagatgt    1140
tctattaaga tacccggttc caatgtgtga tatttggttt atcaagtttt cttgtgacct    1200
ccatttaagt tctgttgcga taggtaatca ggaaggaaag gtttatgtct gggatttgaa    1260
aagttgccct cctgttttga ttacaaagtt atcacacaat caatcaaagt ctgtaatcag    1320
gcaaacagcc atgtctgtcg atggaagcac gattcttgct tgctgcgagg acgggactat    1380
atggcgctgg gacgtgatta ccaagggatc ccccggaggt ggaggtggag gtggaggtgg    1440
aggtggaggt ggaggtggaa tgaggacaca tatagagggt catgaagagc tggatgcagc    1500
aagtttgcgt gaacatgaag agttcacgaa agtgaagaac atatcaacaa ttgagcttgg    1560
aaaatatgag attgagactt ggtacttctc cccttttccg ccagaataca atgactgtgt    1620
gaagctcttt ttttgtgagt tttgcctgaa cttcatgaaa cgcaaagagc agcttcaaag    1680
```

```
gcatatgagr aagtgtgacc tgaagcaccc acctggtgat gaaatttacc gaagtggtac    1740
cttgtcaatg tttgaggtag atggcaaaaa gaacaaggtt tatgcacaga atctctgcta    1800
cctggcaaag ttatttcttg accacaaaac tctttactac gatgttgatt tgtttctatt    1860
ctacgttctt tgcgaatgtg atgaccgagg atgccacatg gttgggtact tttcaaagga    1920
gaagcattcg gaagaagcat acaacttagc ttgcattcta accctgcctt catatcaaag    1980
aaaaggctat ggaaagttct taatagcctt ttcctatgaa ctgtcaaaga agagggaaa    2040 agttgggaca ccggraaaga cccttgtcgg atctaggctt actaagctac agaggttatt    2100
ggactcgtgt tctattagaa atcttgaaaa aacataactc gagggggggc ccgctagagt    2160
cctgctttaa tgagatatgc gagacgccta tgatcgcatg atatttgctt tcaattctgt    2220
tgtgcacgtt gtaaaaaacc tgagcatgtg tagctcagat ccttaccgcc ggtttcggtt    2280
cattctaatg aatatatcac ccgttactat cgtattttta tgaataatat tctccgttca    2340
atttactgat tgtaccctac tacttatatg tacaatatta aaatgaaaac aatatattgt    2400
gctgaatagg tttatagcga catctatgat agagcgccac aataacaaac aattgcgttt    2460
tattattaca aatccaattt taaaaaaagc ggcagaaccg gtcaaaccta aaagactgat    2520
tacataaatc ttattcaaat ttcaaaaggc cccaggggct agtatctacg acacaccgag    2580
cggcgaacta ataacgttca ctgaagggaa ctccggttcc ccgccggcgc gcatgggtga    2640
gattccttga agttgagtat tggccgtccg ctctaccgaa agttacgggc accattcaac    2700
ccggtccagc acggcggccg ggtaaccgac ttgctgcccc gagaattatg cagcattttt    2760
ttggtgtatg tgggccccaa atgaagtgca ggtcaaacct tgacagtgac gcaaatcgtt    2820
gggcgggtcc aggcgaatt ttgcgacaac atgtcgaggc tcagcag    2867
```

<210> SEQ ID NO 21
<211> LENGTH: 932
<212> TYPE: PRT
<213> ORGANISM: Artificial Sequence
<220> FEATURE:
<223> OTHER INFORMATION: Synthetically generated construct
<220> FEATURE:
<221> NAME/KEY: VARIANT
<222> LOCATION: 906
<223> OTHER INFORMATION: Xaa = Any Amino Acid

<400> SEQUENCE: 21

```
Met Glu Lys Glu Asn His Glu Asp Asp Gly Glu Gly Leu Pro Pro Glu
 1               5                  10                  15

Leu Asn Gln Ile Lys Glu Gln Ile Glu Lys Glu Arg Phe Leu His Ile
            20                  25                  30

Lys Arg Lys Phe Glu Leu Arg Tyr Ile Pro Ser Val Ala Thr His Ala
        35                  40                  45

Ser His His Gln Ser Phe Asp Leu Asn Gln Pro Ala Ala Glu Asp Asp
    50                  55                  60

Asn Gly Gly Asp Asn Lys Ser Leu Leu Ser Arg Met Gln Asn Pro Leu
65                  70                  75                  80

Arg His Phe Ser Ala Ser Ser Asp Tyr Asn Ser Tyr Glu Asp Gln Gly
                85                  90                  95

Tyr Val Leu Asp Glu Asp Gln Asp Tyr Ala Leu Glu Glu Asp Val Pro
            100                 105                 110

Leu Phe Leu Asp Glu Asp Val Pro Leu Leu Pro Ser Val Lys Leu Pro
        115                 120                 125
```

-continued

```
Ile Val Glu Lys Leu Pro Arg Ser Ile Thr Trp Val Phe Thr Lys Ser
130                 135                 140

Ser Gln Leu Met Ala Glu Ser Asp Ser Val Ile Gly Lys Arg Gln Ile
145                 150                 155                 160

Tyr Tyr Leu Asn Gly Glu Ala Leu Glu Leu Ser Ser Glu Glu Asp Glu
                165                 170                 175

Glu Asp Glu Glu Glu Asp Glu Glu Ile Lys Lys Glu Lys Cys Glu
            180                 185                 190

Phe Ser Glu Asp Val Asp Arg Phe Ile Trp Thr Val Gly Gln Asp Tyr
            195                 200                 205

Gly Leu Asp Asp Leu Val Val Arg Arg Ala Leu Ala Lys Tyr Leu Glu
210                 215                 220

Val Asp Val Ser Asp Ile Leu Glu Arg Tyr Asn Glu Leu Lys Leu Lys
225                 230                 235                 240

Asn Asp Gly Thr Ala Gly Glu Ala Ser Asp Leu Thr Ser Lys Thr Ile
                245                 250                 255

Thr Thr Ala Phe Gln Asp Phe Ala Asp Arg Arg His Cys Arg Arg Cys
                260                 265                 270

Met Ile Phe Asp Cys His Met His Glu Lys Tyr Glu Pro Glu Ser Arg
            275                 280                 285

Ser Ser Glu Asp Lys Ser Ser Leu Phe Glu Asp Glu Asp Arg Gln Pro
290                 295                 300

Cys Ser Glu His Cys Tyr Leu Lys Val Arg Ser Val Thr Glu Ala Asp
305                 310                 315                 320

His Val Met Asp Asn Asp Asn Ser Ile Ser Asn Lys Ile Val Val Ser
                325                 330                 335

Asp Pro Asn Asn Thr Met Trp Thr Pro Val Glu Lys Asp Leu Tyr Leu
            340                 345                 350

Lys Gly Ile Glu Ile Phe Gly Arg Asn Ser Cys Asp Val Ala Leu Asn
            355                 360                 365

Ile Leu Arg Gly Leu Lys Thr Cys Leu Glu Ile Tyr Asn Tyr Met Arg
370                 375                 380

Glu Gln Asp Gln Cys Thr Met Ser Leu Asp Leu Asn Lys Thr Thr Gln
385                 390                 395                 400

Arg His Asn Gln Val Thr Lys Lys Val Ser Arg Lys Ser Ser Arg Ser
                405                 410                 415

Val Arg Lys Lys Ser Arg Leu Arg Lys Tyr Ala Arg Tyr Pro Pro Ala
            420                 425                 430

Leu Lys Lys Thr Thr Ser Gly Glu Ala Lys Phe Tyr Lys His Tyr Thr
            435                 440                 445

Pro Cys Thr Cys Lys Ser Lys Cys Gly Gln Gln Cys Pro Cys Leu Thr
450                 455                 460

His Glu Asn Cys Cys Glu Lys Tyr Cys Gly Cys Ser Lys Asp Cys Asn
465                 470                 475                 480

Asn Arg Phe Gly Gly Cys Asn Cys Ala Ile Gly Gln Cys Thr Asn Arg
                485                 490                 495

Gln Cys Pro Cys Phe Ala Ala Asn Arg Glu Cys Asp Pro Asp Leu Cys
            500                 505                 510

Arg Ser Cys Pro Leu Ser Cys Gly Asp Gly Thr Leu Gly Glu Thr Pro
            515                 520                 525

Val Gln Ile Gln Cys Lys Asn Met Gln Phe Leu Leu Gln Thr Asn Lys
530                 535                 540

Lys Ile Leu Ile Gly Lys Ser Asp Val His Gly Trp Gly Ala Phe Thr
```

-continued

```
                545                 550                 555                 560
Trp Asp Ser Leu Lys Lys Asn Glu Tyr Leu Gly Glu Tyr Thr Gly Glu
                565                 570                 575
Leu Ile Thr His Asp Glu Ala Asn Glu Arg Gly Arg Ile Glu Asp Arg
                580                 585                 590
Ile Gly Ser Ser Tyr Leu Phe Thr Leu Asn Asp Gln Leu Glu Ile Asp
                595                 600                 605
Ala Arg Arg Lys Gly Asn Glu Phe Lys Phe Leu Asn His Ser Ala Arg
            610                 615                 620
Pro Asn Cys Tyr Ala Lys Leu Met Ile Val Arg Gly Asp Gln Arg Ile
625                 630                 635                 640
Gly Leu Phe Ala Glu Arg Ala Ile Glu Glu Gly Glu Leu Phe Phe
                645                 650                 655
Asp Tyr Cys Tyr Gly Pro Glu His Ala Asp Trp Ser Arg Gly Arg Glu
                660                 665                 670
Pro Arg Lys Thr Gly Ala Ser Lys Arg Ser Lys Glu Ala Arg Pro Ala
                675                 680                 685
Arg Gly Ser Pro Gly Gly Gly Gly Gly Gly Gly Gly Gly Gly
                690                 695                 700
Gly Gly Gly Met Arg Thr His Ile Glu Gly His Glu Glu Leu Asp Ala
705                 710                 715                 720
Ala Ser Leu Arg Glu His Glu Glu Phe Thr Lys Val Lys Asn Ile Ser
                725                 730                 735
Thr Ile Glu Leu Gly Lys Tyr Glu Ile Glu Thr Trp Tyr Phe Ser Pro
                740                 745                 750
Phe Pro Pro Glu Tyr Asn Asp Cys Val Lys Leu Phe Phe Cys Glu Phe
                755                 760                 765
Cys Leu Asn Phe Met Lys Arg Lys Glu Gln Leu Gln Arg His Met Arg
                770                 775                 780
Lys Cys Asp Leu Lys His Pro Pro Gly Asp Glu Ile Tyr Arg Ser Gly
785                 790                 795                 800
Thr Leu Ser Met Phe Glu Val Asp Gly Lys Lys Asn Lys Val Tyr Ala
                805                 810                 815
Gln Asn Leu Cys Tyr Leu Ala Lys Leu Phe Leu Asp His Lys Thr Leu
                820                 825                 830
Tyr Tyr Asp Val Asp Leu Phe Leu Phe Tyr Val Leu Cys Glu Cys Asp
                835                 840                 845
Asp Arg Gly Cys His Met Val Gly Tyr Phe Ser Lys Glu Lys His Ser
            850                 855                 860
Glu Glu Ala Tyr Asn Leu Ala Cys Ile Leu Thr Leu Pro Ser Tyr Gln
865                 870                 875                 880
Arg Lys Gly Tyr Gly Lys Phe Leu Ile Ala Phe Ser Tyr Glu Leu Ser
                885                 890                 895
Lys Lys Glu Gly Lys Val Gly Thr Pro Xaa Lys Thr Leu Val Gly Ser
                900                 905                 910
Arg Leu Thr Lys Leu Gln Arg Leu Leu Asp Ser Cys Ser Ile Arg Asn
                915                 920                 925
Leu Glu Lys Thr
            930

<210> SEQ ID NO 22
<211> LENGTH: 2799
<212> TYPE: DNA
<213> ORGANISM: Artificial Sequence
```

<220> FEATURE:
<223> OTHER INFORMATION: Synthetically generated construct

<400> SEQUENCE: 22

| | | | | | |
|---|---|---|---|---|---|
| atggagaagg | aaaaccatga | ggacgatggt | gagggtttgc | cacccgaact | aaatcagata | 60 |
| aaagagcaaa | tcgaaaagga | gagatttctg | catatcaaga | gaaaattcga | gctgagatac | 120 |
| attccaagtg | tggctactca | tgcttcacac | catcaatcgt | ttgacttaaa | ccagcccgct | 180 |
| gcagaggatg | ataatggagg | agacaacaaa | tcactttgt | cgagaatgca | aaacccactt | 240 |
| cgtcatttca | gtgcctcatc | tgattataat | tcttacgaag | atcaaggtta | tgttcttgat | 300 |
| gaggatcaag | attatgctct | tgaagaagat | gtaccattat | ttcttgatga | agatgtacca | 360 |
| ttattaccaa | gtgtcaagct | tccaattgtt | gagaagctac | cacgatccat | tacatgggtc | 420 |
| ttcaccaaaa | gtagccagct | gatggctgaa | agtgattctg | tgattggtaa | gagacaaatc | 480 |
| tattatttga | tggtgaggc | actagaattg | agcagtgaag | aagatgagga | agatgaagaa | 540 |
| gaagatgagg | aagaaatcaa | gaaagaaaaa | tgcgaatttt | ctgaagatgt | agaccgattt | 600 |
| atatggacgg | ttgggcagga | ctatggtttg | atgatctgg | tcgtgcggcg | tgctctcgcc | 660 |
| aagtacctcg | aagtggatgt | ttcggacata | ttggaaagat | acaatgaact | caagcttaag | 720 |
| aatgatggaa | ctgctggtga | ggcttctgat | ttgacatcca | agacaataac | tactgctttc | 780 |
| caggattttg | ctgatagacg | tcattgccgt | cgttgcatga | tattcgattg | tcatatgcat | 840 |
| gagaagtatg | agcccgagtc | tagatccagc | gaagacaaat | ctagtttgtt | tgaggatgaa | 900 |
| gatagacaac | catgcagtga | gcattgttac | ctcaaggtca | ggagtgtgac | agaagctgat | 960 |
| catgtgatgg | ataatgataa | ctctatatca | aacaagattg | tggtctcaga | tccaaacaac | 1020 |
| actatgtgga | cgcctgtaga | gaaggatctt | tacttgaaag | gaattgagat | atttgggaga | 1080 |
| aacagttgtg | atgttgcatt | aaacatactt | cgggggctta | agacgtgcct | agagatttac | 1140 |
| aattacatgc | gcgaacaaga | tcaatgtact | atgtcattag | accttaacaa | aactacacaa | 1200 |
| agacacaatc | aggttaccaa | aaagtatct | cgaaaaagta | gtaggtcggt | ccgcaaaaaa | 1260 |
| tcgagactcc | gaaaatatgc | tcgttatccg | cctgctttaa | agaaaacaac | tagtggagaa | 1320 |
| gctaagtttt | ataagcacta | cacaccatgc | acttgcaagt | caaaatgtgg | acagcaatgc | 1380 |
| ccttgtttaa | ctcacgaaaa | ttgctgcgag | aaatattgcg | ggtgctcaaa | ggattgcaac | 1440 |
| aatcgctttg | gaggatgtaa | ttgtgcaatt | ggccaatgca | caaatcgaca | atgtccttgt | 1500 |
| tttgctgcta | atcgtgaatg | cgatccagat | ctttgtcgga | gttgtcctct | tagctgtgga | 1560 |
| gatggcactc | ttggtgagac | accagtgcaa | atccaatgca | agaacatgca | attcctcctt | 1620 |
| caaaccaata | aaaagattct | cattggaaag | tctgatgttc | atggatgggg | tgcatttaca | 1680 |
| tgggactctc | ttaaaaagaa | tgagtatctc | ggagaatata | ctggagaact | gatcactcat | 1740 |
| gatgaagcta | atgagcgtgg | gagaatagaa | gatcggattg | gttcttccta | cctctttacc | 1800 |
| ttgaatgatc | agctcgaaat | cgatgctcgc | cgtaaaggaa | acgagttcaa | atttctcaat | 1860 |
| cactcagcaa | gacctaactg | ctacgccaag | ttgatgattg | tgagaggaga | tcagaggatt | 1920 |
| ggtctatttg | cggagagagc | aatcgaagaa | ggtgaggagc | ttttcttcga | ctactgctat | 1980 |
| ggaccagaac | atgcggattg | gtcgcgtggt | cgagaaccta | aaagactgg | tgcttctaaa | 2040 |
| aggtctaagg | aagcccgtcc | agctcgtgga | tcccccggag | gtggaggtgg | aggtggaggt | 2100 |
| ggaggtggag | gtggaggtgg | aatgaggaca | catatagagg | gtcatgaaga | gctggatgca | 2160 |
| gcaagtttgc | gtgaacatga | agagttcacg | aaagtgaaga | acatatcaac | aattgagctt | 2220 |

```
ggaaaatatg agattgagac ttggtacttc tcccctttc cgccagaata caatgactgt    2280
gtgaagctct ttttttgtga gttttgcctg aacttcatga aacgcaaaga gcagcttcaa    2340
aggcatatga graagtgtga cctgaagcac ccacctggtg atgaaattta ccgaagtggt    2400
accttgtcaa tgtttgaggt agatggcaaa aagaacaagg tttatgcaca gaatctctgc    2460
tacctggcaa agttatttct tgaccacaaa actctttact acgatgttga tttgttttcta   2520 ttctacgttc tttgcgaatg tgatgaccga ggatgccaca tggttgggta cttttcaaag    2580
gagaagcatt cggaagaagc atacaactta gcttgcattc taaccctgcc ttcatatcaa    2640
agaaaaggct atggaaagtt cttaatagcc ttttcctatg aactgtcaaa gaaagaggga    2700
aaagttggga caccggraaa gaccttgtc ggatctaggc ttactaagct acagaggtta    2760
ttggactcgt gttctattag aaatcttgaa aaaacataa                          2799
```

<210> SEQ ID NO 23
<211> LENGTH: 81
<212> TYPE: PRT
<213> ORGANISM: Homo sapiens

<400> SEQUENCE: 23

```
Leu Ala Leu Ile Lys Asp Gly Arg Val Ile Gly Gly Ile Cys Phe Arg
  1               5                  10                  15

Met Phe Pro Thr Gln Gly Phe Thr Glu Ile Val Phe Cys Ala Val Thr
             20                  25                  30

Ser Asn Glu Gln Val Lys Gly Tyr Gly Thr His Leu Met Asn His Leu
         35                  40                  45

Lys Glu Tyr His Ile Lys His Asp Ile Leu Tyr Phe Leu Thr Tyr Ala
     50                  55                  60

Asp Glu Tyr Ala Ile Gly Tyr Phe Lys Lys Gln Gly Phe Ser Lys Glu
 65                  70                  75                  80

Ile
```

<210> SEQ ID NO 24
<211> LENGTH: 82
<212> TYPE: PRT
<213> ORGANISM: Homo sapiens

<400> SEQUENCE: 24

```
Leu Ala Leu Ile Lys Asp Gly Arg Val Ile Gly Gly Ile Cys Phe Arg
  1               5                  10                  15

Met Phe Pro Thr Gln Gly Phe Thr Glu Ile Val Phe Cys Ala Val Thr
             20                  25                  30

Ser Asn Glu Gln Val Lys Gly Tyr Gly Thr His Leu Met Asn His Leu
         35                  40                  45

Lys Glu Tyr His Ile Lys His Asn Ile Leu Tyr Phe Leu Thr Tyr Ala
     50                  55                  60

Asp Glu Tyr Ala Ile Gly Tyr Phe Ile Lys Lys Gln Gly Phe Ser Lys
 65                  70                  75                  80

Asp Ile
```

<210> SEQ ID NO 25
<211> LENGTH: 82
<212> TYPE: PRT
<213> ORGANISM: Saccharomyces cerevisiae

<400> SEQUENCE: 25

```
Ala Val Ile Arg Lys Pro Leu Thr Val Val Gly Gly Ile Thr Tyr Arg
```

```
                 1               5                  10                 15
Pro Phe Asp Lys Arg Glu Phe Ala Glu Ile Val Phe Cys Ala Ile Ser
                20                  25                  30

Ser Thr Glu Gln Val Arg Gly Tyr Gly Ala His Leu Met Asn His Leu
        35                  40                  45

Lys Asp Tyr Val Arg Asn Thr Ser Asn Ile Lys Tyr Phe Leu Thr Tyr
    50                  55                  60

Ala Asp Asn Tyr Ala Ile Gly Tyr Phe Lys Lys Gln Gly Phe Thr Lys
65                  70                  75                  80

Glu Ile

<210> SEQ ID NO 26
<211> LENGTH: 71
<212> TYPE: PRT
<213> ORGANISM: Tetrahymena thermophila

<400> SEQUENCE: 26

Val Ile Leu Lys Asn Lys Gln Lys Val Ile Gly Gly Ile Cys Phe Arg
1               5                   10                  15

Phe Ala Glu Val Ala Phe Leu Ala Val Thr Ala Asn Glu Gln Val Arg
                20                  25                  30

Gly Tyr Gly Thr Arg Leu Met Asn Lys Phe Lys Asp His Met Gln Lys
            35                  40                  45

Gln Asn Leu Thr Tyr Ala Asp Asn Phe Ala Ile Gly Tyr Phe Lys Lys
        50                  55                  60

Gln Gly Phe Thr Lys Glu His
65                  70

<210> SEQ ID NO 27
<211> LENGTH: 69
<212> TYPE: PRT
<213> ORGANISM: Artificial Sequence
<220> FEATURE:
<223> OTHER INFORMATION: consensus sequence

<400> SEQUENCE: 27

Leu Ala Leu Ile Lys Asp Gly Arg Val Ile Gly Gly Ile Cys Phe Gly
1               5                   10                  15

Phe Glu Ile Val Phe Cys Ala Val Thr Ser Asn Glu Gln Val Lys Gly
                20                  25                  30

Tyr Gly Thr His Leu Met Asn His Leu Lys Glu Tyr His Ile Lys His
            35                  40                  45

Asn Leu Thr Tyr Ala Asp Tyr Ala Ile Gly Tyr Phe Lys Lys Gln Gly
        50                  55                  60

Phe Ser Lys Glu Ile
65

<210> SEQ ID NO 28
<211> LENGTH: 69
<212> TYPE: PRT
<213> ORGANISM: Saccharomyces cerevisiae

<400> SEQUENCE: 28

Ser Thr Lys Pro Met Gly Phe Phe Ser Lys Asp Leu Val Ser Tyr Gln
1               5                   10                  15

Gln Asn Asn Leu Ala Cys Ile Leu Ile Phe Pro Pro Tyr Gln Arg Arg
                20                  25                  30

Gly Leu Gly Leu Leu Leu Ile Glu Phe Ser Tyr Lys Leu Ser Gln Leu
```

```
                35                  40                  45
Glu Gly Val Ile Ser Gly Pro Glu Val Pro Leu Ser Pro Phe Gly Leu
    50                  55                  60

Ile Gly Tyr Leu Lys
65
```

<210> SEQ ID NO 29
<211> LENGTH: 71
<212> TYPE: PRT
<213> ORGANISM: Homo sapiens

<400> SEQUENCE: 29

```
Cys Lys Gly Phe His Ile Val Gly Tyr Phe Ser Lys Glu Lys Glu Ser
 1                5                  10                  15

Thr Glu Asp Tyr Asn Val Ala Cys Ile Leu Thr Leu Pro Pro Tyr Gln
                20                  25                  30

Arg Arg Gly Tyr Gly Lys Leu Leu Ile Glu Phe Ser Tyr Glu Leu Ser
            35                  40                  45

Lys Val Glu Gly Lys Thr Gly Thr Pro Glu Lys Pro Leu Ser Asp Leu
    50                  55                  60

Gly Leu Leu Ser Tyr Arg Ser
65                  70
```

<210> SEQ ID NO 30
<211> LENGTH: 70
<212> TYPE: PRT
<213> ORGANISM: Drosophila melanogaster

<400> SEQUENCE: 30

```
Glu Gly Ser His Ile Val Gly Tyr Phe Ser Lys Glu Lys Lys Ser Leu
 1                5                  10                  15

Glu Asn Tyr Asn Val Ala Cys Ile Leu Val Leu Pro Pro His Gln Arg
                20                  25                  30

Lys Gly Phe Gly Lys Leu Leu Ile Ala Phe Ser Tyr Glu Leu Ser Arg
            35                  40                  45

Lys Glu Gly Val Ile Gly Ser Pro Glu Lys Pro Leu Ser Asp Leu Gly
    50                  55                  60

Arg Leu Ser Tyr Arg Ser
65                  70
```

<210> SEQ ID NO 31
<211> LENGTH: 71
<212> TYPE: PRT
<213> ORGANISM: Saccharomyces cerevisiae

<400> SEQUENCE: 31

```
Glu Leu Gly His His Leu Val Gly Tyr Phe Ser Lys Glu Lys Glu Ser
 1                5                  10                  15

Ala Asp Gly Tyr Asn Val Ala Cys Ile Leu Thr Leu Pro Gln Tyr Gln
                20                  25                  30

Arg Met Gly Tyr Gly Lys Leu Leu Ile Glu Phe Ser Tyr Glu Leu Ser
            35                  40                  45

Lys Lys Glu Asn Lys Val Gly Ser Pro Glu Lys Pro Leu Ser Asp Leu
    50                  55                  60

Gly Leu Leu Ser Tyr Arg Ala
65                  70
```

<210> SEQ ID NO 32

```
<211> LENGTH: 71
<212> TYPE: PRT
<213> ORGANISM: Schizosaccharomyces pombe

<400> SEQUENCE: 32

Gly Gln Glu Cys Lys Val Ile Gly Tyr Phe Ser Lys Glu Lys Arg Ser
 1               5                  10                  15

Ala Ser Asp Tyr Asn Val Ser Cys Ile Leu Thr Leu Pro Ile Tyr Gln
             20                  25                  30

Arg Arg Gly Tyr Gly Val Phe Leu Ile Asp Phe Ser Tyr Leu Leu Thr
         35                  40                  45

Gln Val Glu Gly Lys Leu Gly Ser Pro Glu Lys Pro Leu Ser Asp Leu
     50                  55                  60

Gly Leu Val Thr Tyr Arg Ser
 65                  70

<210> SEQ ID NO 33
<211> LENGTH: 71
<212> TYPE: PRT
<213> ORGANISM: Homo sapiens

<400> SEQUENCE: 33

Val Lys Gly Cys His Leu Val Gly Tyr Phe Ser Lys Glu Lys His Cys
 1               5                  10                  15

Gln Gln Lys Tyr Asn Val Ser Cys Ile Met Ile Leu Pro Gln Tyr Gln
             20                  25                  30

Arg Lys Gly Tyr Gly Arg Phe Leu Ile Asp Phe Ser Tyr Leu Leu Ser
         35                  40                  45

Lys Arg Glu Gly Gln Ala Gly Ser Pro Glu Lys Pro Leu Ser Asp Leu
     50                  55                  60

Gly Arg Leu Ser Tyr Met Ala
 65                  70

<210> SEQ ID NO 34
<211> LENGTH: 71
<212> TYPE: PRT
<213> ORGANISM: Saccharomyces cerevisiae

<400> SEQUENCE: 34

Ala Ala Lys Phe His Phe Val Gly Tyr Phe Ser Lys Glu Lys Phe Asn
 1               5                  10                  15

Ser Asn Asp Tyr Asn Leu Ser Cys Ile Leu Thr Leu Pro Ile Tyr Gln
             20                  25                  30

Arg Lys Gly Tyr Gly Gln Phe Leu Met Glu Phe Ser Tyr Leu Leu Ser
         35                  40                  45

Arg Lys Glu Ser Lys Phe Gly Thr Pro Glu Lys Pro Leu Ser Asp Leu
     50                  55                  60

Gly Leu Leu Thr Tyr Arg Thr
 65                  70

<210> SEQ ID NO 35
<211> LENGTH: 71
<212> TYPE: PRT
<213> ORGANISM: Caenorhabditis elegans

<400> SEQUENCE: 35

Asp Ile Gly Cys His Phe Ala Gly Tyr Phe Ser Lys Glu Lys Tyr Glu
 1               5                  10                  15

Pro Asp Val Asn Asn Leu Ser Cys Ile Met Thr Leu Pro Cys Tyr Gln
```

-continued

```
                20                  25                  30
Glu Met Gly Leu Gly Arg Phe Leu Ile Asp Ile Ser Tyr Ala Leu Ser
             35                  40                  45
Arg Lys Glu Lys Trp Phe Gly Gly Pro Glu Gln Pro Leu Ser Glu Leu
 50                  55                  60
Gly Arg Lys Ala Tyr Gly Gly
 65                  70

<210> SEQ ID NO 36
<211> LENGTH: 57
<212> TYPE: PRT
<213> ORGANISM: Artificial Sequence
<220> FEATURE:
<223> OTHER INFORMATION: consensus sequence

<400> SEQUENCE: 36

Gly His Ile Val Gly Tyr Phe Ser Lys Glu Lys Ser Tyr Asn Val Cys
  1               5                  10                  15

Ile Leu Thr Leu Pro Tyr Gln Arg Arg Gly Tyr Gly Lys Leu Ile Glu
             20                  25                  30

Phe Ser Tyr Leu Ser Lys Lys Glu Gly Gly Thr Pro Glu Lys Pro Leu
             35                  40                  45

Ser Asp Leu Gly Leu Leu Ser Tyr Arg
 50                  55

<210> SEQ ID NO 37
<211> LENGTH: 71
<212> TYPE: PRT
<213> ORGANISM: Saccharomyces cerevisiae

<400> SEQUENCE: 37

Tyr Glu Pro Asp Lys Lys Asp Ile Leu Ile Gly Leu Leu Arg Leu Gly
  1               5                  10                  15

Ser Val Val Pro Leu His Ser Arg Asp Pro Arg Lys Phe Gln His Gln
             20                  25                  30

Gly Phe Gly Thr Leu Leu Met Glu Glu Ala Glu Arg Ile Ala Lys Glu
             35                  40                  45

Glu His Ser Val Ile Ser Gly Val Gly Val Arg Asn Tyr Tyr Gly Lys
 50                  55                  60

Leu Gly Tyr Glu Leu Asp Gly
 65                  70

<210> SEQ ID NO 38
<211> LENGTH: 104
<212> TYPE: PRT
<213> ORGANISM: Saccharomyces cerevisiae

<400> SEQUENCE: 38

Leu Leu Asn Lys Lys Thr Lys Glu Leu Ile Gly Phe Val Thr Thr Tyr
  1               5                  10                  15

Lys Tyr Trp His Tyr Leu Gly Ala Lys Ser Phe Asp Glu Asp Ile Asp
             20                  25                  30

Lys Lys Phe Arg Ala Lys Ile Ser Gln Phe Leu Ile Phe Pro Pro Tyr
             35                  40                  45

Gln Asn Lys Gly His Gly Ser Cys Leu Tyr Glu Ala Ile Ile Gln Ser
 50                  55                  60

Trp Leu Glu Asp Lys Ser Ile Thr Glu Ile Thr Val Glu Asp Pro Asn
 65                  70                  75                  80
```

-continued

Glu Ala Phe Asp Asp Leu Arg Asp Arg Asn Asp Ile Gln Arg Leu Arg
                85                  90                  95

Lys Leu Gly Tyr Asp Ala Val Phe
            100

<210> SEQ ID NO 39
<211> LENGTH: 45
<212> TYPE: PRT
<213> ORGANISM: Saccharomyces cerevisiae

<400> SEQUENCE: 39

His Pro Cys Tyr Glu Leu Lys Lys Leu Leu Ser Asn Gly Ser Phe Tyr
1               5                   10                  15

Ser Ser Asp Ser Asp Leu Thr Ser Thr Leu Gln His Arg Gly Tyr Gly
            20                  25                  30

Gln His Ser Leu Ser Thr Asp Thr Tyr Glu Glu Glu Tyr
        35                  40                  45

<210> SEQ ID NO 40
<211> LENGTH: 34
<212> TYPE: PRT
<213> ORGANISM: Saccharomyces cerevisiae

<400> SEQUENCE: 40

Ile Tyr Ile Asn Asp Leu Tyr Val Asp Glu Asn Ser Arg Val Lys Gly
1               5                   10                  15

Ala Gly Gly Lys Leu Ile Gln Phe Val Tyr Asp Glu Ala Asp Lys Leu
            20                  25                  30

Gly Thr

<210> SEQ ID NO 41
<211> LENGTH: 71
<212> TYPE: PRT
<213> ORGANISM: Saccharomyces cerevisiae

<400> SEQUENCE: 41

Ala Phe Asp Thr Glu Thr Gly Asp Ala Ile Gly Phe Ala His Tyr Glu
1               5                   10                  15

Val Val Tyr Met Asn Asp Leu Tyr Val Thr Glu Arg Ala Arg Val Lys
            20                  25                  30

Gly Val Gly Arg Lys Leu Ile Glu Phe Val Tyr Ser Arg Ala Asp Glu
        35                  40                  45

Leu Gly Thr Asp His Tyr Asn His Arg Ala Gln Leu Leu Tyr Thr Lys
    50                  55                  60

Val Ala Tyr Lys Thr Asp Lys
65                  70

<210> SEQ ID NO 42
<211> LENGTH: 50
<212> TYPE: PRT
<213> ORGANISM: Saccharomyces cerevisiae

<400> SEQUENCE: 42

Met Leu Thr Glu Glu Thr Gly Leu Val Glu Gly Asp Ala Leu His Glu
1               5                   10                  15

Val Ser Val Pro Val Ile Tyr Leu Tyr Glu Val His Val Ala Ser Ala
            20                  25                  30

His Arg Gly His Gly Ile Gly Arg Arg Leu Leu Glu His Ala Leu Cys
        35                  40                  45

-continued

```
Asp Gly
    50

<210> SEQ ID NO 43
<211> LENGTH: 33
<212> TYPE: PRT
<213> ORGANISM: Saccharomyces cerevisiae

<400> SEQUENCE: 43

Val Val Thr Gly Thr Phe Leu Val Asn Ala Gly Ile Arg Gly Lys Gly
 1               5                  10                  15

Ile Gly Lys Thr Leu Met Glu Thr Phe Ile Glu Trp Ser Lys Lys Leu
            20                  25                  30

Gly

<210> SEQ ID NO 44
<211> LENGTH: 34
<212> TYPE: PRT
<213> ORGANISM: Schizosaccharomyces pombe

<400> SEQUENCE: 44

Val Gly Ile Tyr Leu Glu Asp Leu Tyr Val Arg Pro Gln Phe Arg Gly
 1               5                  10                  15

Lys Gly Tyr Gly Ser Tyr Leu Leu Ser Tyr Leu Ala Arg Glu Ser Leu
            20                  25                  30

Arg Ile

<210> SEQ ID NO 45
<211> LENGTH: 26
<212> TYPE: PRT
<213> ORGANISM: Artificial Sequence
<220> FEATURE:
<223> OTHER INFORMATION: consensus sequence

<400> SEQUENCE: 45

Val Ile Tyr Ile Asp Leu Tyr Val Arg Gly Lys Gly Val Gly Arg Lys
 1               5                  10                  15

Leu Ile Glu Phe Val Glu Ala Lys Leu Gly
            20                  25
```